United States Patent
Huang et al.

(10) Patent No.: US 10,537,644 B2
(45) Date of Patent: Jan. 21, 2020

(54) COVALENT LINKERS IN ANTIBODY-DRUG CONJUGATES AND METHODS OF MAKING AND USING THE SAME

(71) Applicant: RC Biotechnologies, Inc., Fremont, CA (US)

(72) Inventors: Chang Jiang Huang, Los Angeles, CA (US); Jianmin Fang, Palo Alto, CA (US); Hui Ye, Shandong (CN); Lezhi Zhang, Shandong (CN)

(73) Assignee: RC BIOTECHNOLOGIES, INC., Fremont, CA (US)

( * ) Notice: Subject to any disclaimer, the term of this patent is extended or adjusted under 35 U.S.C. 154(b) by 0 days.

(21) Appl. No.: 15/524,487

(22) PCT Filed: Aug. 15, 2016

(86) PCT No.: PCT/US2016/046987
§ 371 (c)(1),
(2) Date: May 4, 2017

(87) PCT Pub. No.: WO2017/031034
PCT Pub. Date: Feb. 23, 2017

(65) Prior Publication Data
US 2018/0055948 A1    Mar. 1, 2018

Related U.S. Application Data

(60) Provisional application No. 62/205,121, filed on Aug. 14, 2015.

(51) Int. Cl.
| | | |
|---|---|---|
| A61K 47/68 | (2017.01) | |
| A61K 31/44 | (2006.01) | |
| C07D 257/08 | (2006.01) | |
| A61K 47/54 | (2017.01) | |
| C07K 16/28 | (2006.01) | |
| A61P 35/00 | (2006.01) | |
| C07K 16/32 | (2006.01) | |

(52) U.S. Cl.
CPC ........... *A61K 47/545* (2017.08); *A61K 47/54* (2017.08); *A61K 47/6803* (2017.08); *A61K 47/6811* (2017.08); *A61K 47/6855* (2017.08); *A61K 47/6869* (2017.08); *A61K 47/6889* (2017.08); *A61P 35/00* (2018.01); *C07K 16/2896* (2013.01); *C07K 16/32* (2013.01)

(58) Field of Classification Search
None
See application file for complete search history.

(56) References Cited

U.S. PATENT DOCUMENTS

| | | | |
|---|---|---|---|
| 2003/0215395 A1 | 11/2003 | Yu et al. | |
| 2005/0232928 A1* | 10/2005 | Ojima | ............... C07C 323/62 424/178.1 |
| 2016/0015832 A1* | 1/2016 | An | .................. C07D 207/452 530/391.9 |

FOREIGN PATENT DOCUMENTS

| | | | | |
|---|---|---|---|---|
| CN | 103933575 A | 7/2014 | | |
| WO | WO 2013/085925 A1 | 6/2013 | | |
| WO | WO-2013185117 A1 * | 12/2013 | ............. | C07K 16/40 |

OTHER PUBLICATIONS

Qin, Min et al., "Click Conjugation of Peptide to Hydrogel Nanoparticles for Tumor-Targeted Drug Delivery." *Biomacromolecules*, 2014, 15(10): 3728-3734.
Yao, Xuejing, et al., "A novel humanized anti-HER2 antibody conjugated with MMAE exerts potent anti-tumor activity." *Breast Cancer Research and Treatment*, 2015, 153(1): 123-133.

* cited by examiner

*Primary Examiner* — Mark Halvorson
*Assistant Examiner* — Kauser M Akhoon
(74) *Attorney, Agent, or Firm* — Saliwanchik, Lloyd & Eisenschenk

(57) ABSTRACT

The present invention provides novel and advantageous compositions having a linker capable of covalently coupling one or more free thiols of an antibody. Specifically, provided herein are the molecular structures, synthetic pathways, coupling mechanisms, and applications thereof as used in an antibody-drug conjugate (ADC).

7 Claims, 4 Drawing Sheets

COVALENT LINKERS IN ANTIBODY-DRUG CONJUGATES AND METHODS OF MAKING AND USING THE SAME

CROSS REFERENCE TO A RELATED APPLICATION

This application is a National Stage Application of International Application No. PCT/US2016/046987, filed Aug. 15, 2016; which claims the benefit of U.S. Provisional Application Ser. No. 62/205,121, filed Aug. 14, 2015, both of which are incorporated by reference herein in their entirety, including any figures, tables, and drawings.

BACKGROUND OF THE INVENTION

Antibody drug conjugates (ADCs), a rapidly growing class of targeted therapeutics, represent a promising new approach toward improving both the selectivity and the cytotoxic activity of cancer drugs. An example of ADC drug having been approved for therapeutic use in the U.S. is brentuximab vedotin (ADCETRIS®), a chimeric anti-CD30 antibody conjugated to monomethyl auristatin E used in treating anaplastic large cell lymphoma and Hodgkin lymphoma.

One conventional method employed in the design of antibody-drug conjugates (ADC) involves the coupling of drug molecules to thiol groups of antibody chains via a linking moiety. Free thiol groups are obtained as a result of breaking the cysteine interchain disulfide bonds of an antibody via a reduction reaction. A typical antibody contains 4 interchain disulfide bonds (2 between the heavy chains and 2 between the heavy and light chains). These interchain disulfides can be selectively reduced with dithiothreitol, tris(2-carboxyethyl)phosphine, or other mild reducing agents, to result in 8 reactive sulfhydryl groups for conjugation. This method can link up to eight drug molecules to a given antibody.

Due to the fact that at least two disulfide bonds are broken, ADCs designed using this principle are unstable once entered into circulation, and thus the half life of ADCs will be shortened. As a result, recent development in ADC design and synthesis adopts a different approach, namely, one that relies on covalently connecting two thiol groups by a coupling agent, thereby establishing thiol bridges between the two heavy chains and between the heavy and the light chains of a given antibody. Current research efforts exploring such an approach mainly focus on designing the structure of a coupling agent that not only has the functionalities to bridge two thiol groups covalently, but also encompasses the necessary components to facilitate specific biological activities.

Earlier studies in the field have utilized bis-maleimides to react with the two thiol groups resulted from a broken disulfide bond. The covalent coupling between maleimides and thiols is a classic alkene conversion reaction. More recently studied thiol-bridging reactions are also based upon this principle, with exemplary reactions involving maleimides, bis-maleimides, and maleimides with halogen substituents. To date, however, thiol-bridging linker compositions are limited to maleimides-based compounds only, and oftentimes not specified for applications in tumor-targeting ADCs. For example, previously disclosed methods of covalent thiol-coupling involving the use of similar maleimides-based compounds did not specify their applications in coupling with active agents such as tumor-targeting drug molecules, proteins, or polypeptides (see, for example, PCT Patent Application Publication No. WO 2013132268). Other methods that specifically disclosed applications in tumor-targeting ADCs utilizing maleimides-based compounds did not employ the covalent thiol-bridging mechanism in which one linker simultaneously reacts with two thiol groups, as provided by the present invention (see, for example, Chinese Patent Application Publication No. CN 103933575).

BRIEF SUMMARY OF THE INVENTION

The present invention provides novel and advantageous linkers for coupling an antibody to another compound. In addition to the linkers which the structural synthesis and the use thereof described herein, the subject invention also provides antibody/active-agent conjugates, and applications thereof as used in, for example, antibody-drug conjugate applications.

Some embodiments provide a linker-active agent having the structure of Formula I:

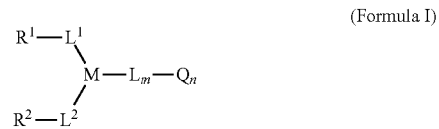

or a pharmaceutically acceptable salt thereof,
wherein:
$R^1$ and $R^2$ are functional groups that can react with thiols;
$L^1$, $L^2$, L represent linker or can be null;
M represents a linking group;
Q represents an active agent or can be null;
m represents an integer from 0 to 6;
n represents an integer from 0 to 8.
In some embodiments, $R^1$ and $R^2$ are independently selected from

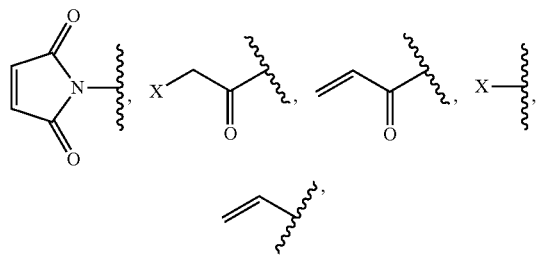

and derivatives thereof;
Some embodiments provide a targeting moiety and a linker-active agent conjugate having the structure of Formula II:

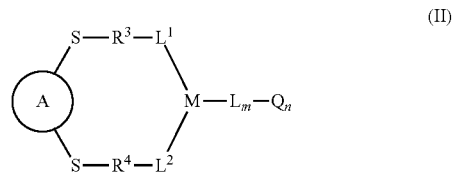

or a pharmaceutically acceptable salt thereof,
A is a targeting moiety;
$L^1$, $L^2$, L represent linker or null;

M is a linking group;
Q is an active agent or null;
m is an integer selected from 0 to 6;
n is an integer selected from 0 to 8;
Each of $R^3$ and $R^4$ is independently selected from:

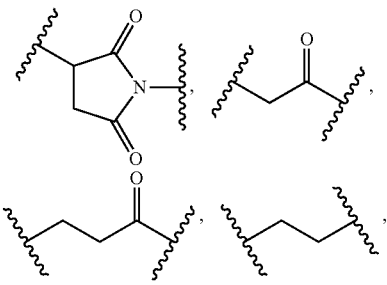

derivatives thereof, or is null.

As used herein, reference to "null" means that the entity is not present.

DETAILED DESCRIPTION OF THE INVENTION

Figure 1:
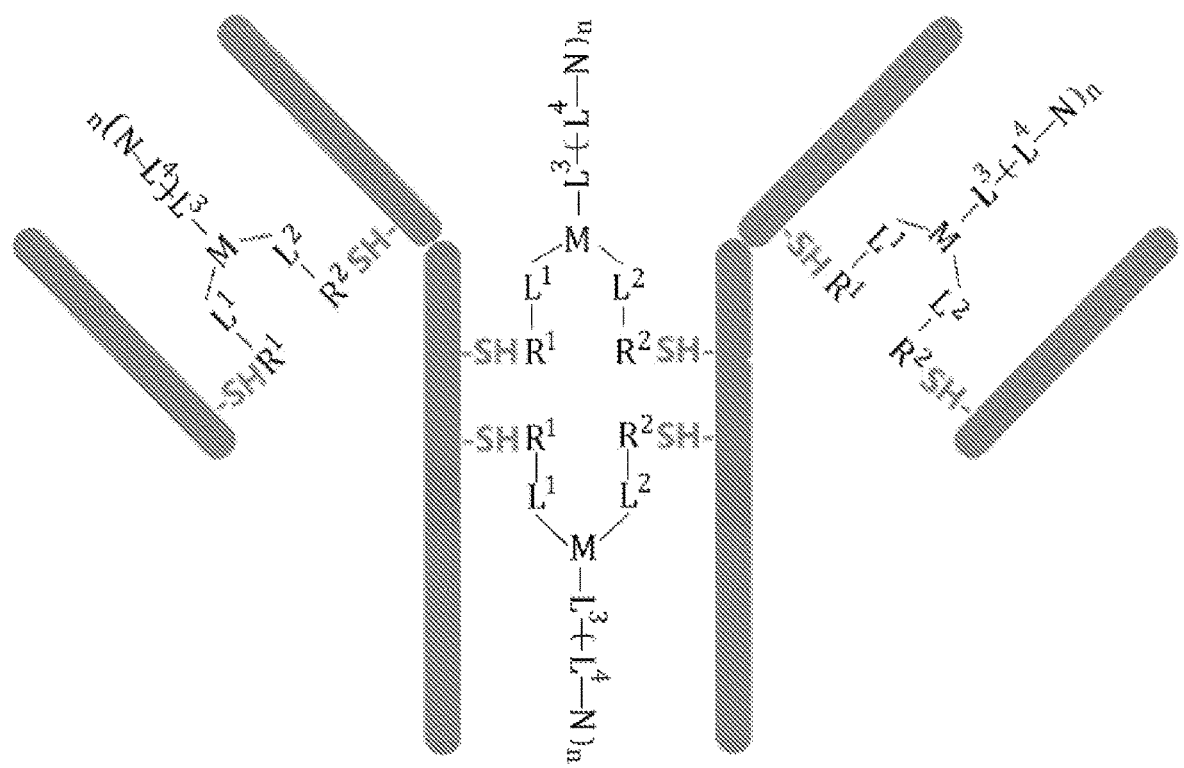
FIG. 1 shows a schematic of covalent thiol-bridge established by a linker reacting with two neighboring thiol groups of a broken or reduced disulfide bond of antibody.

In the following detailed description, reference is made to the accompanying drawings, depicting exemplary, non-limiting and non-exhaustive embodiments of the invention. These embodiments are described in sufficient detail to enable those having skill in the art to practice the invention, and it is understood that other embodiments may be used, and other changes may be made, without departing from the spirit or scope of the invention. The following detailed description is, therefore, not to be taken in a limiting sense, and the scope of the invention is defined only by the appended claims. All patents, patent applications, provisional applications, and publications referred to or cited herein are incorporated by reference in their entirety, including all figures and tables, to the extent that they are not inconsistent with the explicit teachings of this specification.

The present invention provides novel and advantageous Linker molecules capable of covalently coupling to two free thiols of an antibody via one terminus of the Linker, and attaching to an active agent at another terminus of the Linker. Antibody/active-agent conjugates herein are also provided, including, for example, antibody-drug conjugates (ADCs). In some embodiments, ADCs provided herein incorporate an anti-cancer drug as the active agent.

Definitions

As used herein, abbreviations of common organic compounds are defined below:
BOC tert-Butoxycarbonyl
Fmoc 9-Fluorenylmethoxycarbonyl
° C. Temperature in degrees Centigrade
DIPEA Diisopropylethylamine
DMF N,N'-Dimethyl formamide
R.T. Room temperature
EtOH Ethanol
h Hour
$Et_3N$ Triethylamine
HOBt N-Hydroxybenzotriazole
Prep-HPLC Preparative high performance liquid chromatography
$NaHCO_3$ Sodium Bicarbonate
DCC Dicyclohexyl carbodiimide
MeCN Acetonitrile
EDC 1-Ethyl-3-(3-dimethylaminopropyl) carbodiimide
DIC N,N'-diisopropyl carbodiimide
DEA Diethylamine
$K_2CO_3$ Potassium carbonate
M Mole/liter
mL Milliliter
$MgSO_4$ Magnesium sulphate
THF Tetrahydrofuran
$CH_2Cl_2$ Dichloromethane
NaCl Sodium chloride
$NaSO_4$ Sodium sulfate
HCl Hydrochloric Acid
LC-MS Liquid chromatography-mass spectrometry
$CHCl_3$ Trichloromethane
NaAc Sodium acetate
$Ac_2O$ Acetic anhydride
TFA Trifluoroacetic acid
NaOH Sodium hydroxide The term "active agent" as used according to the present invention includes any natural or synthetic substance that has a physiological effect when administered to an animal. The active agent can be utilized in accordance with the invention to treat, for example, warm blooded animals, particularly mammals including humans, veterinarian animals and farm animals. The active agent may act on, or be visualized at, a desired target within, or on, the animal body, including tumor tissue.

Non-limiting examples of "active agents" are drugs acting at synaptic sites and neuroeffector junctional sites; general and local analgesics; hypnotics and sedatives; drugs for the treatment of psychiatric disorders such as depression and schizophrenia; anti-epileptics and anticonvulsants; drugs for the treatment of Parkinson's and Huntington's disease, aging and Alzheimer's disease; excitatory amino acid antagonists, neurotrophic factors and neuroregenerative agents; trophic factors; drugs aimed at the treatment of central nervous system (CNS) trauma or stroke; drugs for the treatment of addiction and drug abuse; drugs for the treatment of bacterial, viral and/or microbial infections, such as influenza, HIV, herpes, chicken pox, and the like; antacoids and anti-inflammatory drugs; chemotherapeutic agents for parasitic infections and diseases caused by microbes; immunosuppressive agents; anti-cancer drugs; hormones and hormone antagonists; heavy metals and heavy metal antagonists; antagonists for non-metallic toxic agents; cytostatic agents; visualization agents and other diagnostic substances; immunoactive and immunoreactive agents; transmitters and their respective receptor agonists and receptor antagonists, their respective precursors and metabolites; transporter inhibitors; antibiotics; antispasmodics; antihistamines; antinauseants; relaxants; stimulants; sense and antisense oligonucleotides; cerebral dilators; psychotropics; antimanics; vascular dilators and constrictors; anti-hypertensives; drugs for migraine treatment; hyperglycemic and hypoglycemic agents; minerals and nutritional agents; anti-obesity drugs; anabolics; anti-asthmatics; and mixtures thereof.

An "antibody," also known as an immunoglobulin, is a large Y-shaped protein used by the immune system to identify and neutralize foreign entities such as bacteria and viruses. An antibody has four polypeptide chains, two identical heavy chains and two identical light chains connected by cysteine disulfide bonds.

A "monoclonal antibody" is a monospecific antibody where all the antibody molecules are identical because they are made by identical immune cells that are all clones of a unique parent cell. Monoclonal antibodies can be prepared by fusing myeloma cells with the spleen cells from a mouse (or B-cells from a rabbit) that has been immunized with the desired antigen, then purifying the resulting hybridomas by such techniques as affinity purification. Recombinant monoclonal antibodies can be prepared in viruses or yeast cells rather than in mice, through technologies including repertoire cloning or phage display/yeast display, the cloning of immunoglobulin gene segments to create libraries of antibodies with slightly different amino acid sequences from which antibodies with desired specificities may be obtained. The resulting antibodies may be prepared on a large scale by fermentation.

"Chimeric" or "humanized" antibodies are antibodies containing a combination of the original (usually mouse) and human DNA sequences used in the recombinant process, such as those in which mouse DNA encoding the binding portion of a monoclonal antibody is merged with human antibody-producing DNA to yield a partially-mouse, partially-human monoclonal antibody. Full-humanized antibodies are produced using transgenic mice (engineered to produce human antibodies) or phage display libraries.

A "linker" is a moiety with two reactive termini, one for binding, or otherwise associating with, a biological moiety or a fragment thereof, such as an antibody (or fragment thereof), and the other for conjugation to an active agent such as a cytotoxin.

A "cytotoxin" is an entity that, when in the presence of a cell, such as a cancer cell, is toxic or induces key functional changes to that cell.

As used herein, "alkyl" refers to a straight or branched hydrocarbon chain that is fully saturated (i.e., contains no double or triple bonds). The alkyl group may have 1 to 9 carbon atoms (whenever it appears herein, a numerical range such as "1 to 9" refers to each integer in the given range; e.g., "1 to 9 carbon atoms" means that the alkyl group may comprise 1 carbon atom, 2 carbon atoms, 3 carbon atoms, etc., up to and including 9 carbon atoms, although the present definition also covers the occurrence of the term "alkyl" where no numerical range is designated). The alkyl group may also be a medium size alkyl having 1 to 9 carbon atoms. Typical alkyl groups include, but are in no way limited to, methyl, ethyl, propyl, isopropyl, butyl, isobutyl, tertiary butyl, pentyl, hexyl, and the like.

As used herein, "alkenyl" refers to a straight or branched hydrocarbon chain containing one or more double bonds. The alkenyl group may have 2 to 9 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, I-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain comprising one or more triple bonds. The alkynyl group may have 2 to 9 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

The term "aromatic" refers to a ring or ring system having a conjugated z electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "cycloalkyl" means a fully saturated carbocyclyl ring or ring system. Examples include, but are not limited to, cyclopropyl, cyclobutyl, cyclopentyl, and cyclohexyl.

As used herein, "heteroaryl" refers to an aromatic ring or ring system (i.e., two or more fused rings that share two adjacent atoms) that comprise(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

Linker/Active-Agent

In one aspect, the present invention provides a linker-active agent that can be represented as Formula I:

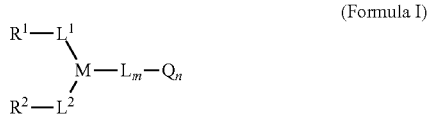

(Formula I)

or a pharmaceutically acceptable salt thereof,
wherein:
$L^1$, $L^2$, L represent a linker or null;
M is a linking group;
Q is an active agent or null;
m is an integer selected from 0 to 6;
n is an integer selected from 0 to 8;
each of $R^1$ and $R^2$ is a functional group that can react with a thiol.

In some embodiments, each of the two thiol-reactive functional groups may, independently, comprise a maleimide, halogen, halogen-substituted functional groups, alkanal, alkanone, sulfonyl-alkene, silane, isocyanate, or norbornene, but both cannot be maleimide and both cannot be halogen.

In specific embodiments, each of $R^1$ and $R^2$ is independently selected from:

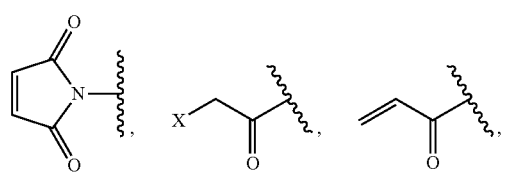

and derivatives thereof;
wherein, in this embodiment, $R^5$, $R^6$, and $R^7$ are independently selected from H, halogen, $C_1$-$C_6$ alkyls, $C_2$-$C_6$ alkenyls, $C_2$-$C_6$ alkynyls, aromatics, heteroaryls, $C_3$-$C_9$ cycloalkyls, $C_3$-$C_9$ heterocyclyl, polyethylene glycol, $NO_2$, CN, SCN, $OR^8$, $SR^9$, $NR^{10}R^{11}$, $C(=O)R^{12}$, $C(=O)OR^8$, $C(=O)NR^{10}R^{11}$, $C(=S)OR^8$, $C(=S)NR^{10}R^{11}$, $C(=S)SR^9$, $NR^{10}(C=O)R^{12}$, $NR^{10}(C=S)NR^{10}R^{11}$, $O(C=O)NR^{10}R^{11}$, $SO_2R^9$, $S(=O)_2OR^8$, and combinations thereof, wherein $R^8$, $R^9$, $R^{10}$, $R^{11}$, $R^{12}$ are independently selected from H, $C_1$-$C_6$ alkyl, $C_2$-$C_6$ alkenyls, $C_2$-$C_6$ alkynyls, and combinations thereof.

X is a halogen; in some embodiments X can be F, Cl, Br, or I;

$R^1$ and $R^2$ can be the same or different;

In some embodiments, M is selected from, for example, C—$R^5$, N, B, P, Si—$R^5$, aromatics, heteroaryls, cycloalkyls, and (heterocyclyl)alkyls, $R^5$ is selected from H, $C_1$-$C_6$ alkyls, $C_2$-$C_6$ alkenyls, and $C_2$-$C_6$ alkynyls.

In other embodiments, M is selected from the group consisting of

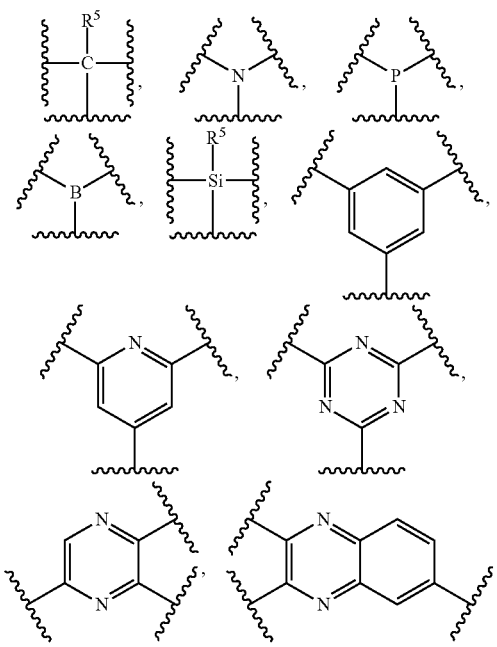

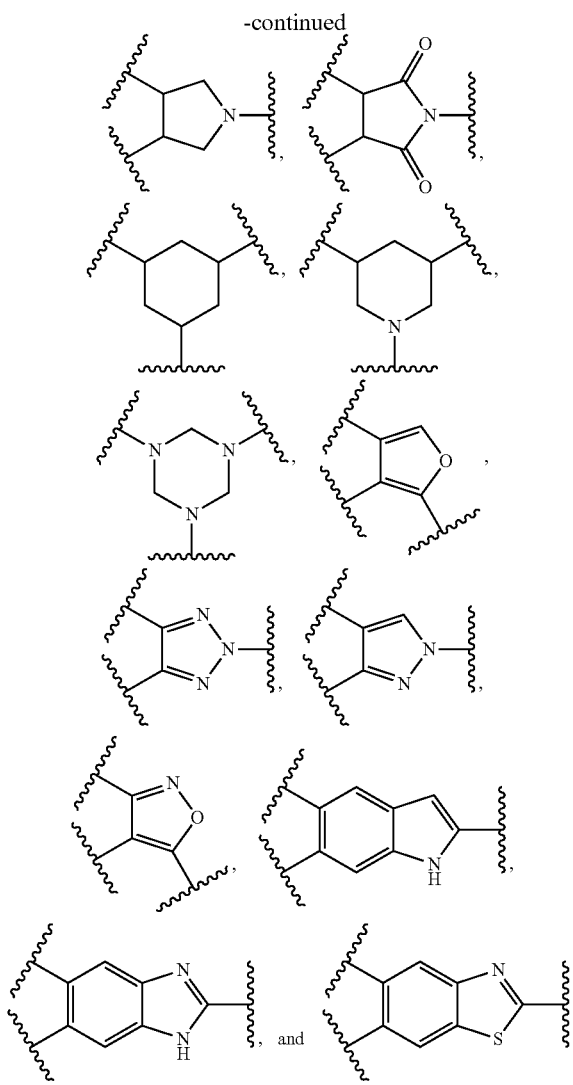

In certain embodiments, M is selected from

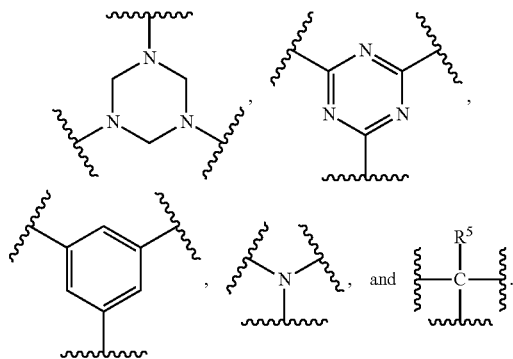

In some embodiments, Q is an active agent, selected from the group consisting of tubulin binders, DNA alkylators, DNA intercalator, enzyme inhibitors, immune modalators, peptides, and nucleotides.

In some embodiments, Q is selected from the group consisting of Maytansinoids, Auristatins, Calicheamicins, Doxorubicins, Duocarmycins, and Pyrrolobenzodiazepines.

In certain embodiments, Q is selected from MMAE, MMAF, PBD dimer, DM1, and DM4. The active agent may be, for example, any of those that are disclosed in WO 2013085925A1, which is incorporated herein, in its entirety, by reference. "Drug" and "active agent" are used interchangeably herein.

In some embodiments, each of the internal linking moieties $L^1$, $L^2$ is independently selected from $C_1$-$C_6$ alkyls, $C_2$-$C_6$ alkenyls, $C_2$-$C_6$ alkynyls, aromatics, heteroaryls, $C_3$-$C_9$ cycloalkyls, $C_3$-$C_9$ heterocyclyl, polyethylene glycol, O, S, $NR^6$, $C(=O)$, $C(=O)O$, $C(=O)NR^6$, $C=NR^6$, $C(=S)O$, $C(=S)NR^6$, $C(=S)S$, $NR^6(C=O)$, $NR^6(C=S)NR^7$, $O(C=O)NR^6$, $S(=O)_2$ and any combination thereof;

wherein, in this embodiment, $R^6$ and $R^7$ are independently selected from H, $C_1$-$C_6$ alkyls, $C_2$-$C_6$ alkenyls, and $C_2$-$C_6$ alkynyls.

In other embodiments, each of $L^1$, $L^2$ is independently selected from:

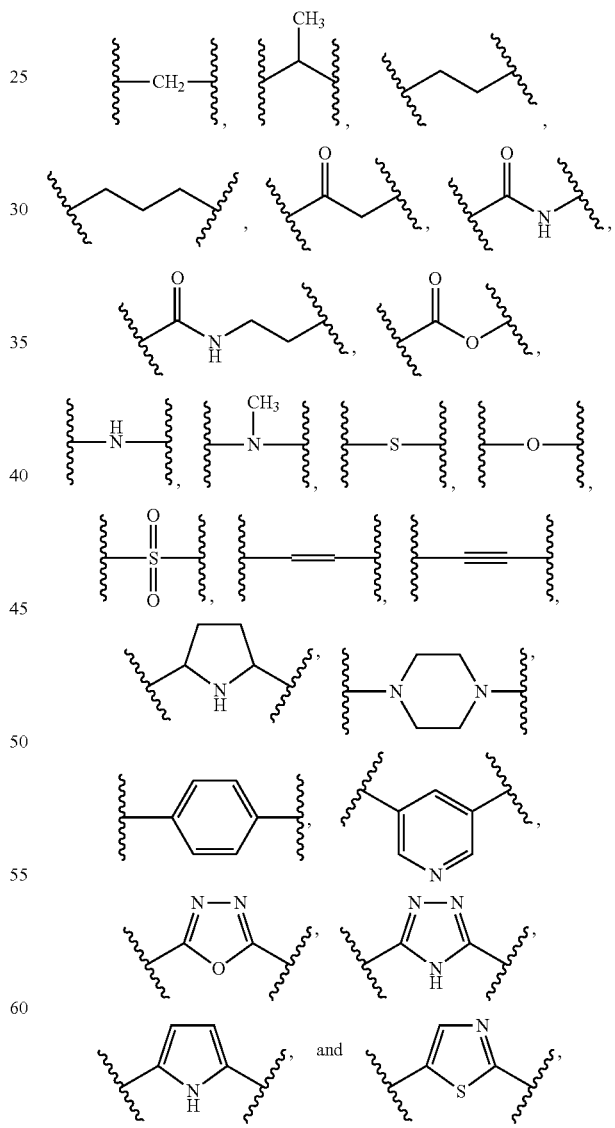

or is null.

In certain embodiments, each of $L^1$, $L^2$ is independently selected from:

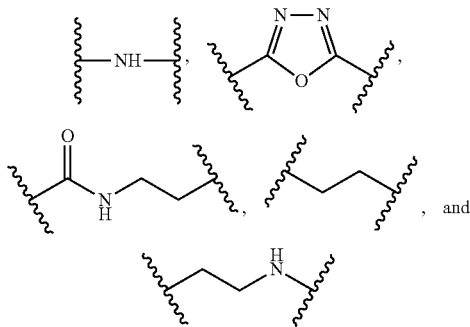

or is null.

L represents a linker, connecting active agent Q to linking group M. In some embodiments, L includes a non-cleavable unit, in other embodiments, L includes a cleavable unit. The linker/active-agent conjugate may have one linker, two linkers, three linkers, four linkers, five linkers or six linkers.

In some embodiments, L is independently selected from $C_1$-$C_9$ alkyls, $C_2$-$C_9$ alkenyls, $C_2$-$C_9$ alkynyls, aromatics, heteroaryls, $C_3$-$C_9$ cycloalkyls, $C_3$-$C_9$ heterocyclyl, polyethylene glycol, O, S, $NR^8$, $C(=O)$, $C(=O)O$, $C(=O)NR^8$, $C=NR^8$, $C(=S)O$, $C(=S)NR^8$, $C(=S)S$, $NR^8(C=O)$, $NR^8(C=S)NR^9$, $O(C=O)NR^8$, $S(=O)_2$, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB and any combination thereof.

In this embodiment, $R^1$ and $R^9$ are independently selected from H, $C_1$-$C_6$ alkyls, $C_2$-$C_6$ alkenyls, and $C_2$-$C_6$ alkynyls.

In some embodiments, L is null. When L is null, active agent Q is connected directly to M.

In some embodiments, L is independently selected from the group consisting of:

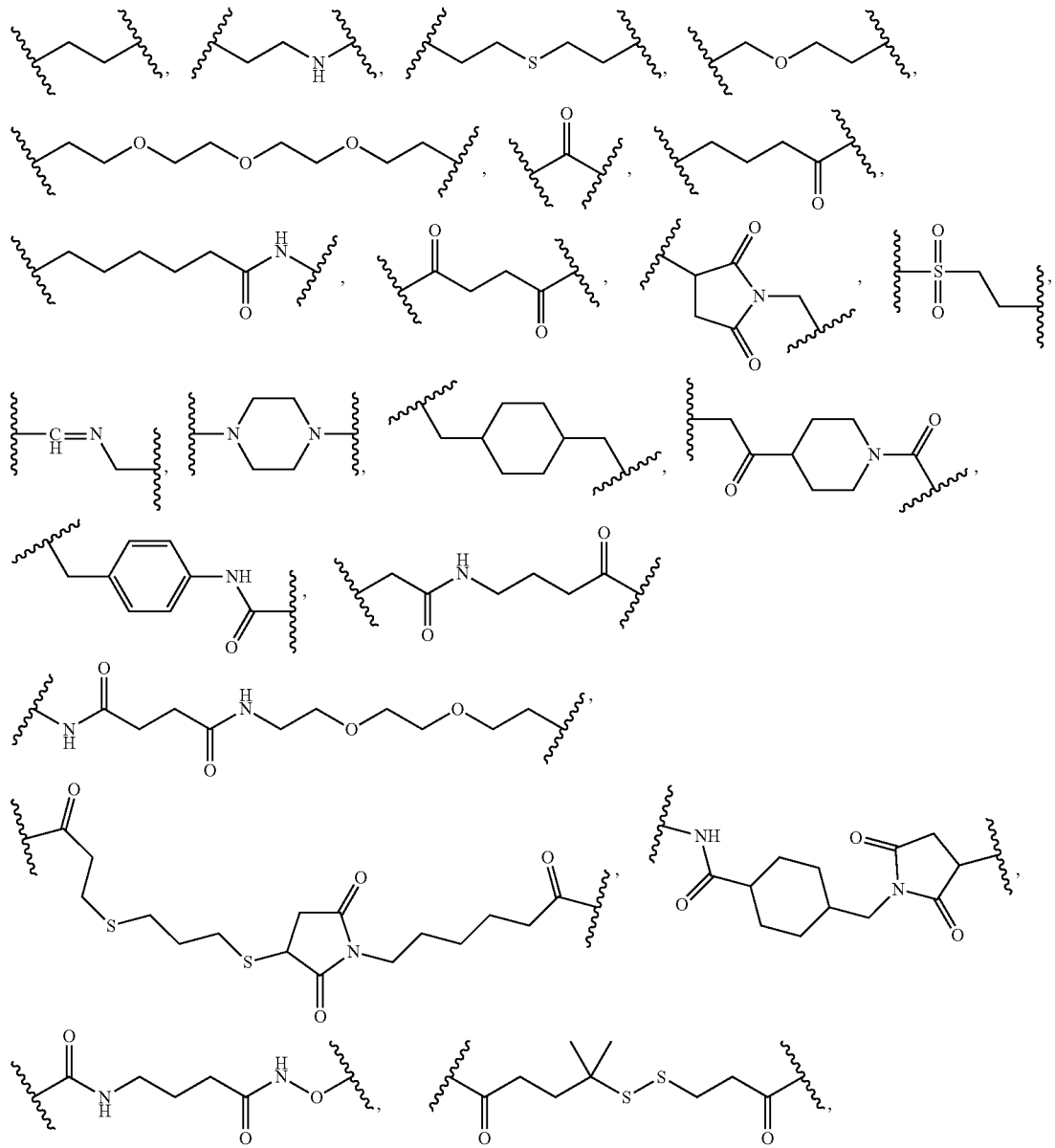

-continued
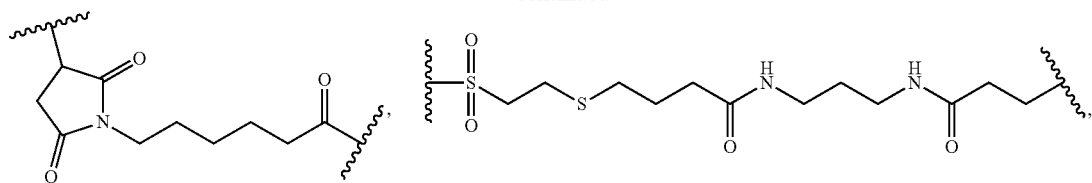
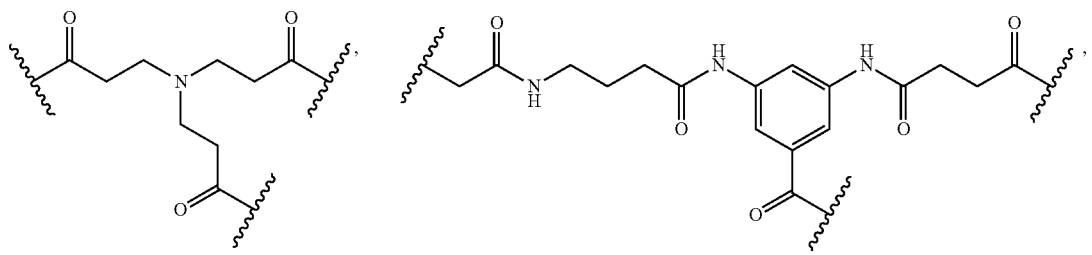
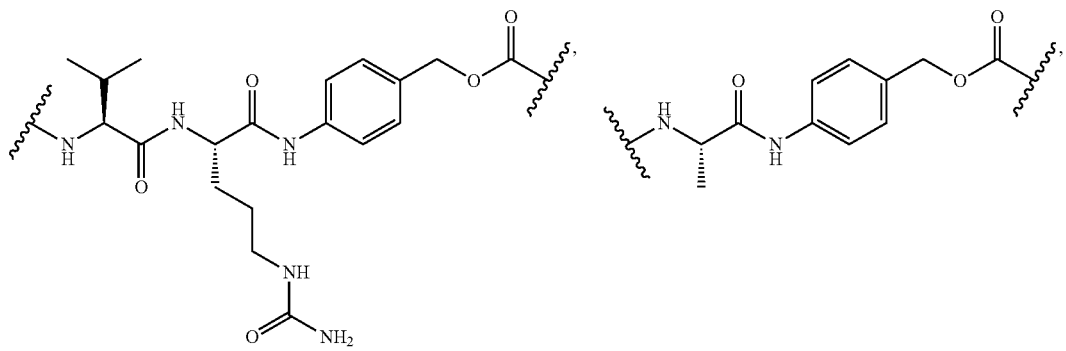
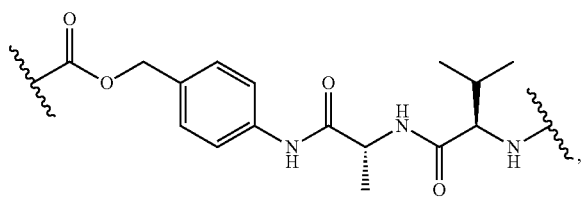
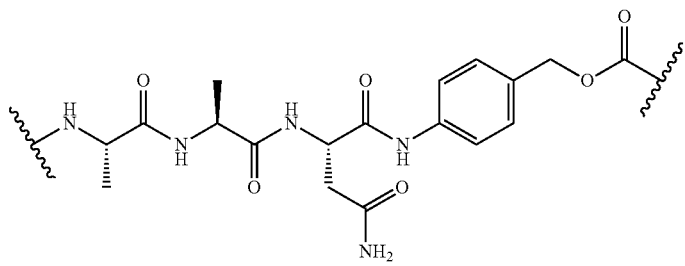
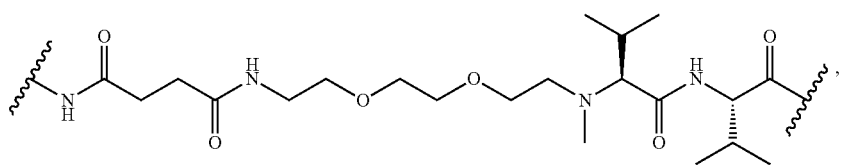

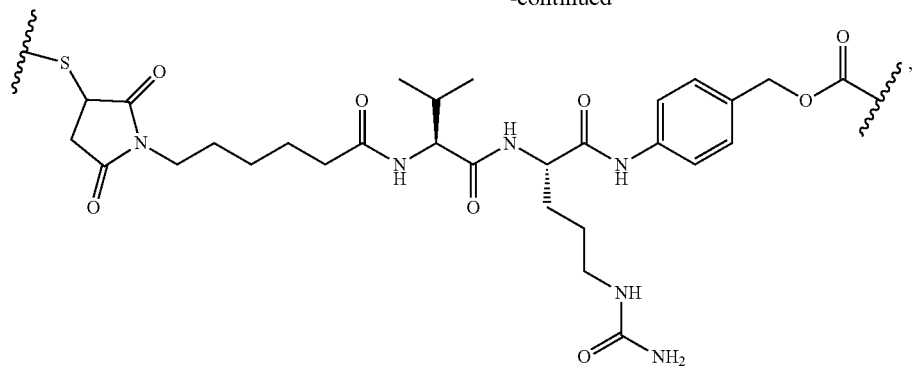
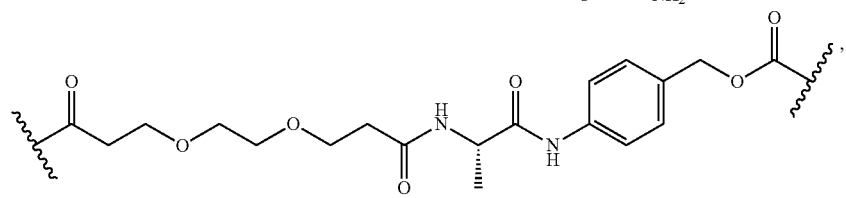
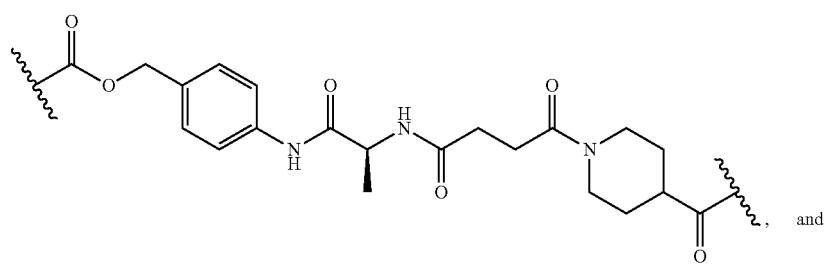
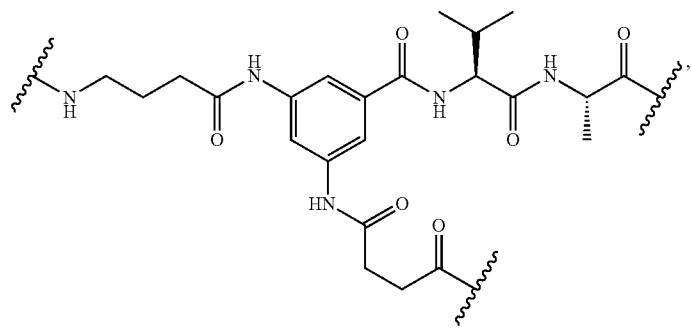 [SMILES: *NCCCC(=O)Nc1cc(NC(=O)CCC(*)=O)cc(C(=O)N[C@H](C(=O)N[C@@H](C)C(*)=O)C(C)C)c1]
or is null.
In some embodiments, L is independently selected from the groups as followed:
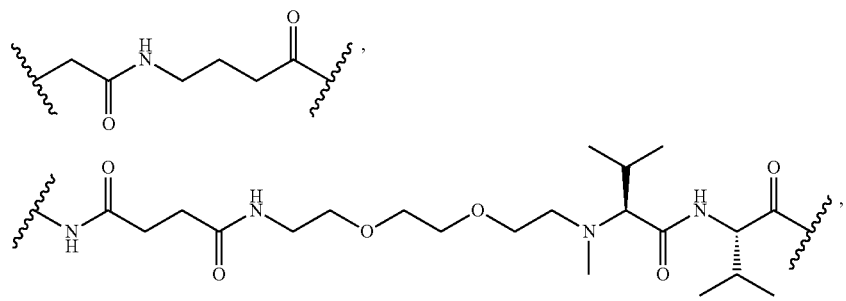

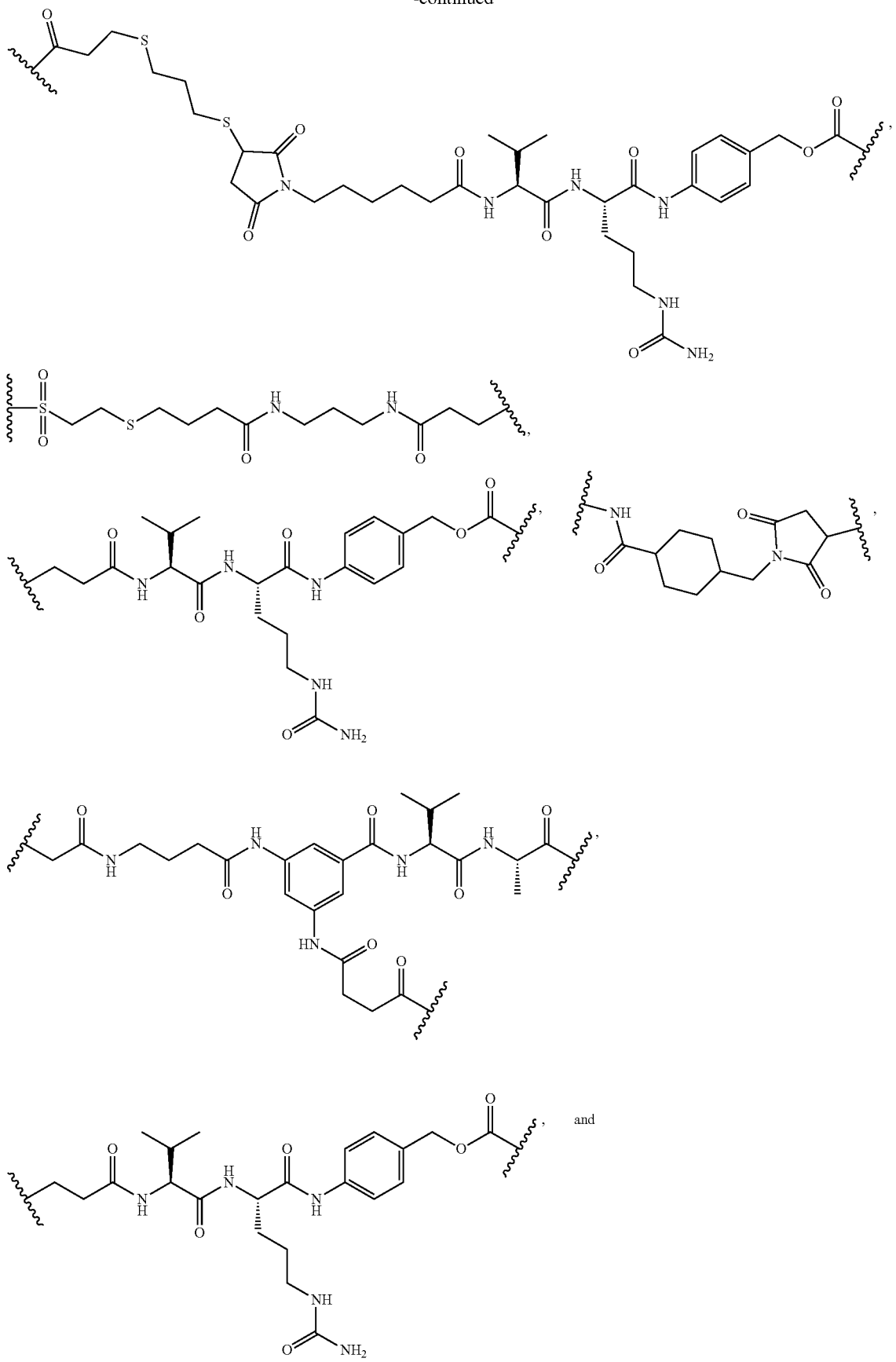

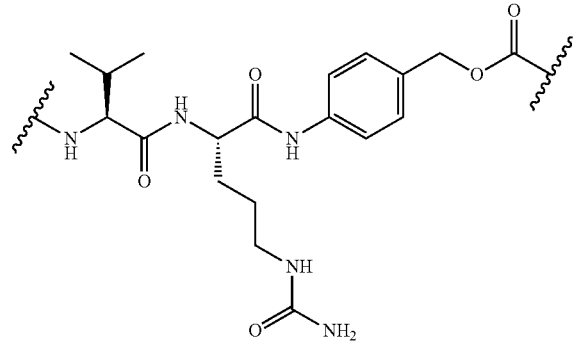
or is null.
In some embodiments, the linker-active agent conjugate has the following structure of Formula I:
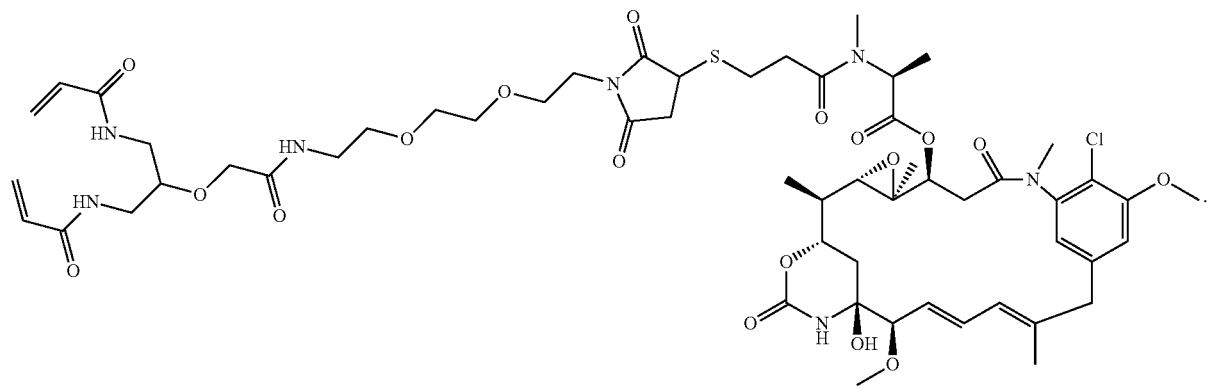 [SMILES: C=CC(=O)NCC(CNC(=O)C=C)OCC(=O)NCCOCCOCCN1C(=O)CC(SCCC(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@@]23C)C1=O]
In some embodiments, the linker-active agent conjugate has the following structure of Formula I:
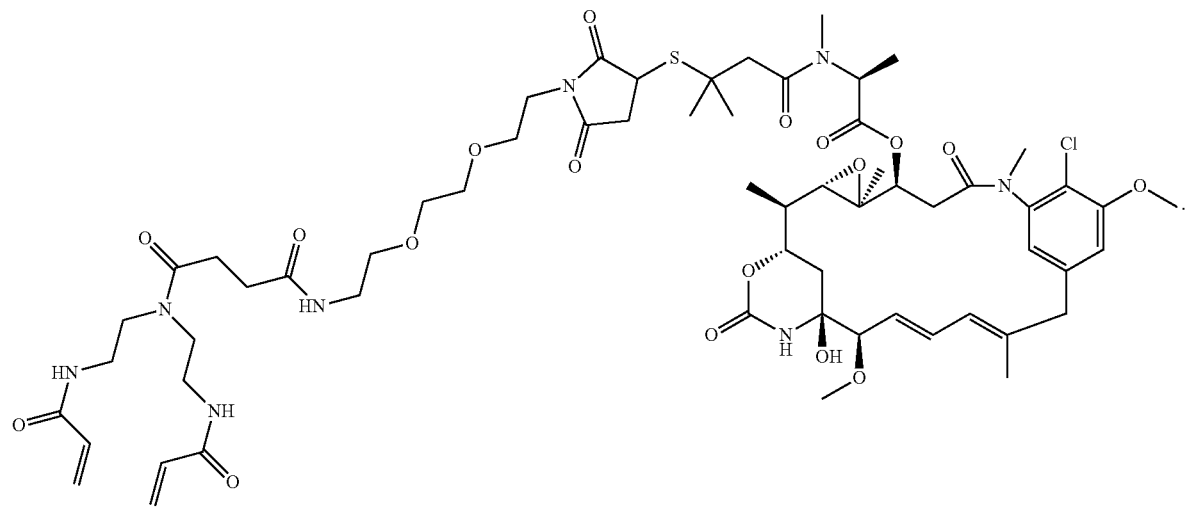 [SMILES: C=CC(=O)NCCN(CCNC(=O)C=C)C(=O)CCC(=O)NCCOCCOCCN1C(=O)CC(SC(C)(C)CC(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@@]23C)C1=O]

In some embodiments, the linker-active agent conjugate has the following structure of Formula I:

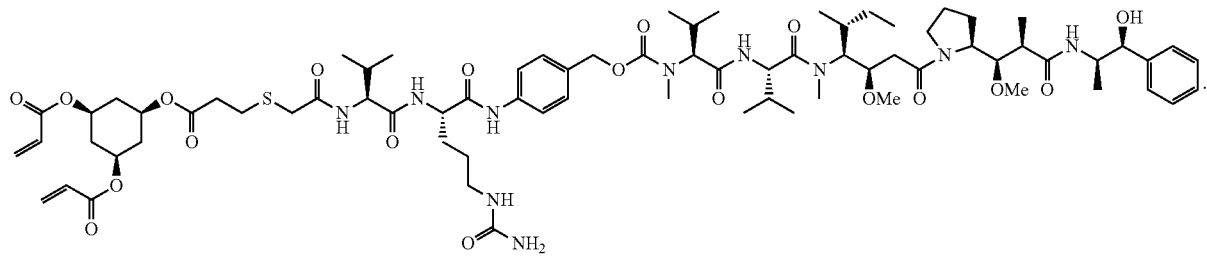 [SMILES: C=CC(=O)O[C@@H]1C[C@H](OC(=O)C=C)C[C@H](OC(=O)CCSCC(=O)N[C@H](C(=O)N[C@@H](CCCNC(N)=O)C(=O)Nc2ccc(COC(=O)N(C)[C@H](C(=O)N[C@H](C(=O)N(C)[C@@H]([C@H](C)CC)[C@@H](CC(=O)N3CCC[C@H]3[C@H](OC)[C@@H](C)C(=O)N[C@H](C)[C@@H](O)c3ccccc3)OC)C(C)C)C(C)C)cc2)C(C)C)C1]

In some embodiments, the linker-active agent conjugate has the following structure of Formula I:

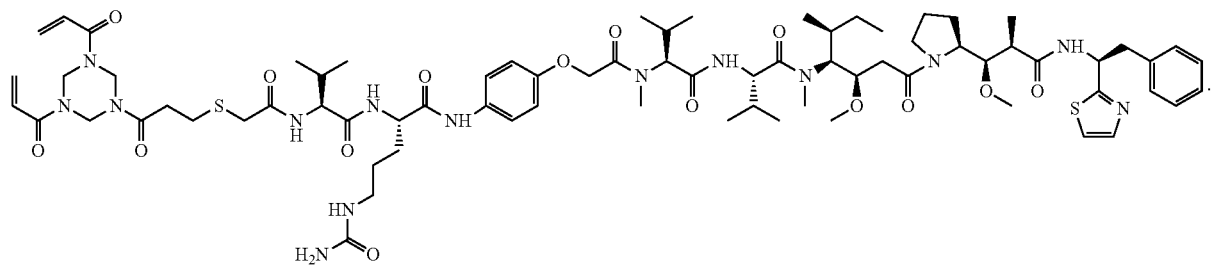 [SMILES: C=CC(=O)N1CN(C(=O)C=C)CN(C(=O)CCSCC(=O)N[C@H](C(=O)N[C@@H](CCCNC(N)=O)C(=O)Nc2ccc(OCC(=O)N(C)[C@H](C(=O)N[C@H](C(=O)N(C)[C@@H]([C@@H](C)CC)[C@@H](CC(=O)N3CCC[C@H]3[C@H](OC)[C@@H](C)C(=O)N[C@@H](Cc3ccccc3)c3nccs3)OC)C(C)C)C(C)C)cc2)C(C)C)C1]

In some embodiments, the linker-active agent conjugate has the following structure of Formula I:

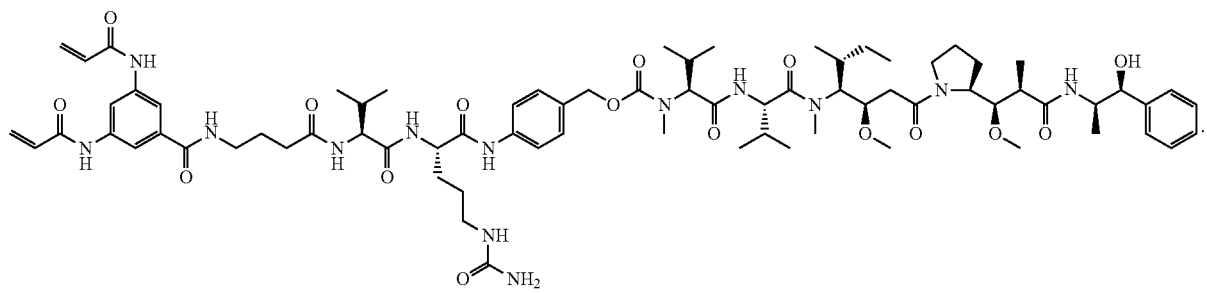 [SMILES: C=CC(=O)Nc1cc(NC(=O)C=C)cc(C(=O)NCCCC(=O)N[C@H](C(=O)N[C@@H](CCCNC(N)=O)C(=O)Nc2ccc(COC(=O)N(C)[C@H](C(=O)N[C@H](C(=O)N(C)[C@@H]([C@H](C)CC)[C@@H](CC(=O)N3CCC[C@H]3[C@H](OC)[C@@H](C)C(=O)N[C@H](C)[C@@H](O)c3ccccc3)OC)C(C)C)C(C)C)cc2)C(C)C)c1]

In some embodiments, the linker-active agent conjugate has the following structure of Formula I:

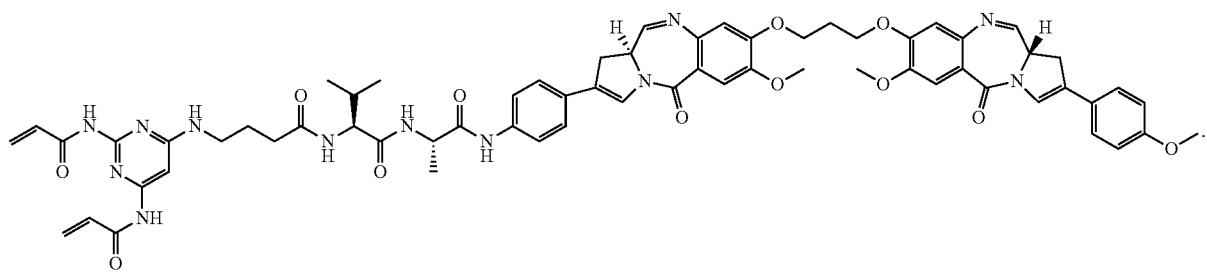 [SMILES: C=CC(=O)Nc1cc(NCCCC(=O)N[C@H](C(=O)N[C@@H](C)C(=O)Nc2ccc(C3=CN4C(=O)c5cc(OC)c(OCCCOc6cc7c(cc6OC)C(=O)N6C=C(c8ccc(OC)cc8)C[C@H]6C=N7)cc5N=C[C@@H]4C3)cc2)C(C)C)nc(NC(=O)C=C)n1]

In some embodiments, the linker-active agent conjugate has the following structure of Formula I:
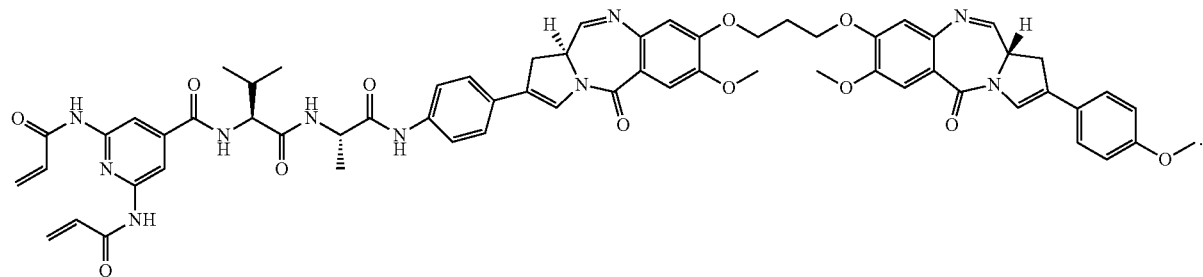 [SMILES: C=CC(=O)Nc1cc(C(=O)N[C@H](C(=O)N[C@@H](C)C(=O)Nc2ccc(C3=CN4C(=O)c5cc(OC)c(OCCCOc6cc7c(cc6OC)C(=O)N6C=C(c8ccc(OC)cc8)C[C@H]6C=N7)cc5N=C[C@@H]4C3)cc2)C(C)C)cc(NC(=O)C=C)n1]
In some embodiments, the linker-active agent conjugate has the following structure of Formula I:
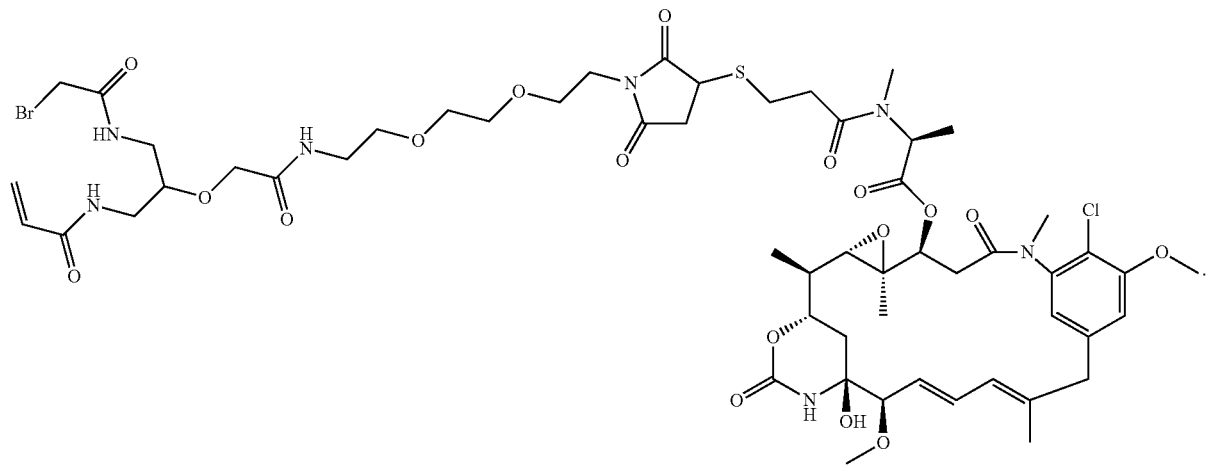
In some embodiments, the linker-active agent conjugate has the following structure of Formula I:
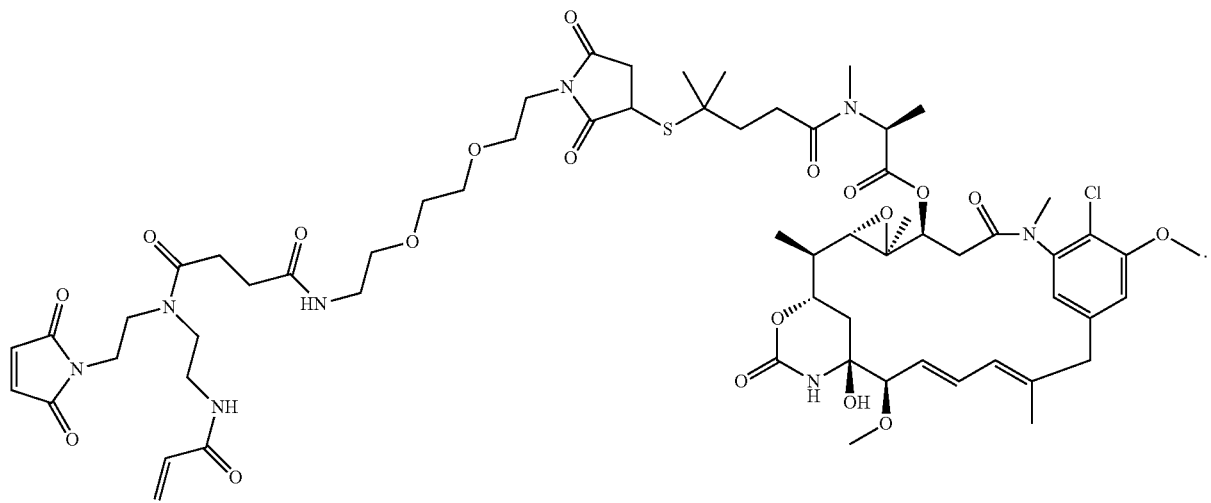 [SMILES: C=CC(=O)NCCN(CCN1C(=O)C=CC1=O)C(=O)CCC(=O)NCCOCCOCCN1C(=O)CC(SC(C)(C)CCC(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@@]23C)C1=O]

In some embodiments, the linker-active agent conjugate has the following structure of Formula I:

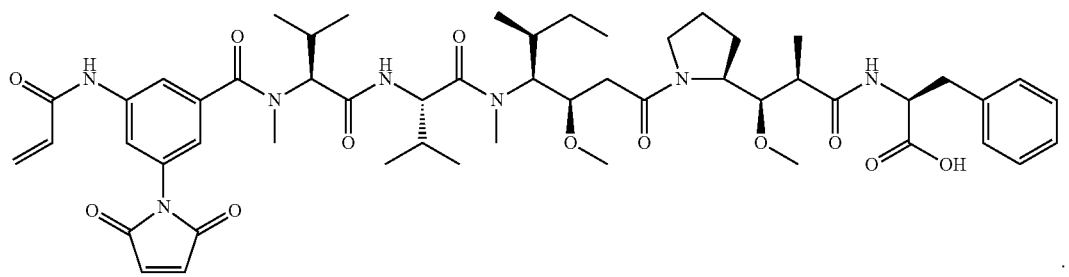 [SMILES: C=CC(=O)Nc1cc(C(=O)N(C)[C@H](C(=O)N[C@H](C(=O)N(C)[C@@H]([C@@H](C)CC)[C@@H](CC(=O)N2CCC[C@H]2[C@H](OC)[C@@H](C)C(=O)N[C@@H](Cc2ccccc2)C(=O)O)OC)C(C)C)C(C)C)cc(N2C(=O)C=CC2=O)c1]

In some embodiments, the linker-active agent conjugate has the following structure of Formula I:

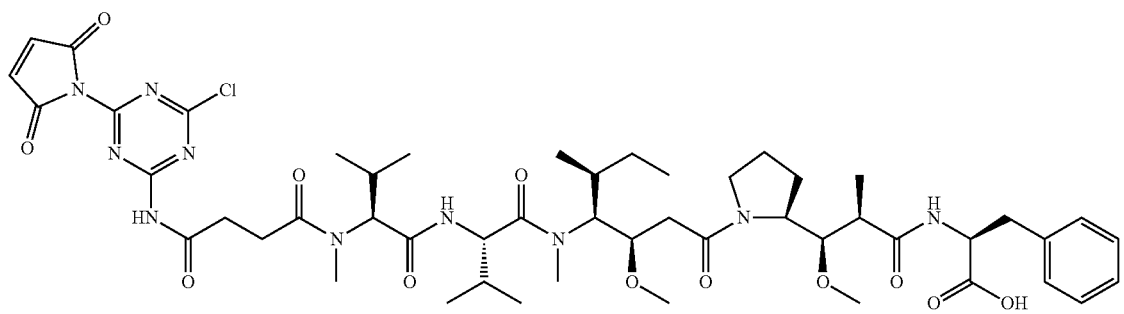

In some embodiments, the linker-active agent conjugate has the following structure of Formula I:

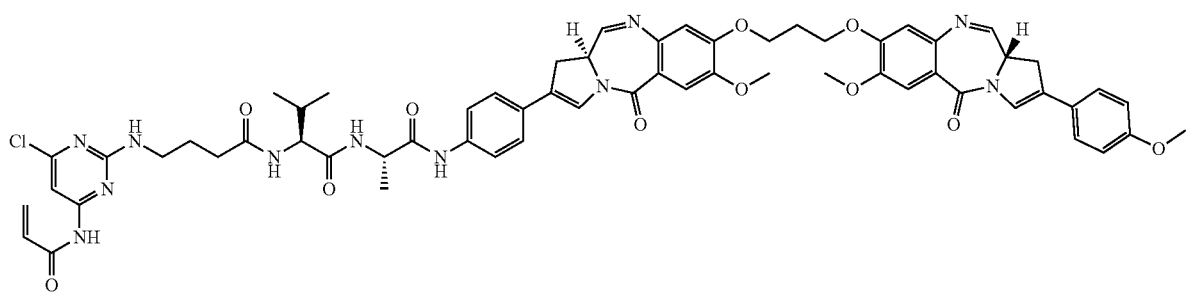 [SMILES: C=CC(=O)Nc1cc(Cl)nc(NCCCC(=O)N[C@H](C(=O)N[C@@H](C)C(=O)Nc2ccc(C3=CN4C(=O)c5cc(OC)c(OCCCOc6cc7c(cc6OC)C(=O)N6C=C(c8ccc(OC)cc8)C[C@H]6C=N7)cc5N=C[C@@H]4C3)cc2)C(C)C)n1]

In another aspect, the present invention provides an antibody drug conjugate having the following formula II:

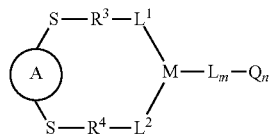

or a pharmaceutically acceptable salt thereof,
A is a targeting moiety;
S is a sulfur atom of a thiol group of the targeting moiety;
$L^1$, $L^2$, L represent a linker or null;
M is a linking group;
Q is an active agent or null;

m is an integer selected from 0 to 6;
n is an integer selected from 0 to 8; and each of $R^3$ and $R^4$ is formed as the result of a reaction between S and a functional group that can react with thiols.

In some embodiments, the functional groups that react with a thiol may, independently, comprise a maleimide, halogen, halogen-substituted functional groups, alkanal, alkanone, sulfonyl-alkene, silane, isocyanate, or norbornene, but both cannot be maleimide and both cannot be halogen.

In certain embodiments, each of $R^3$ and $R^4$ are formed, independently, as the result of a reaction between a thiol group and a group selected from

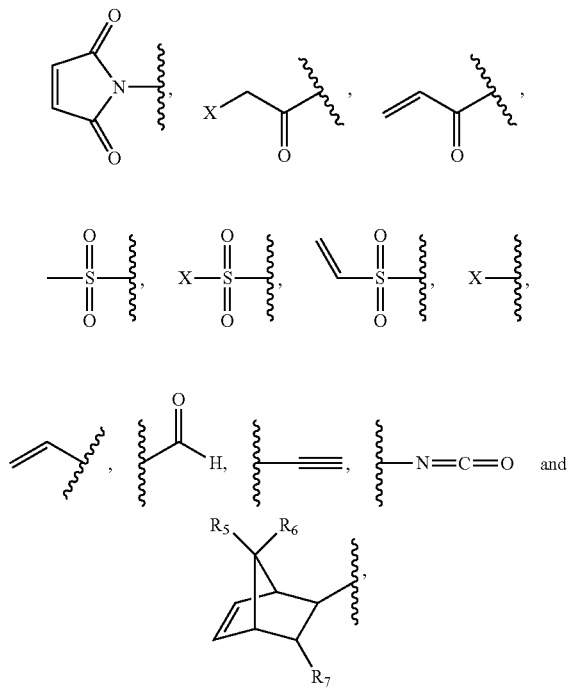

and derivates thereof.

wherein, in this embodiment, $R^5$, $R^6$, and $R^7$ are independently selected from H, halogen, $C_1$-$C_6$ alkyls, $C_2$-$C_6$ alkenyls, $C_2$-$C_6$ alkynyls, aromatics, heteroaryls, $C_3$-$C_9$ cycloalkyls, $C_3$-$C_9$ heterocyclyl, polyethylene glycol, $NO_2$, CN, SCN, $OR^8$, $SR^9$, $NR^{10}R^{11}$, $C(O)R^{12}$, $C(O)OR^8$, $C(=O)NR^{10}R^{11}$, $C(=S)OR^8$, $C(=S)NR^{10}R^{11}$, $C(=S)SR^9$, $NR^{10}(C=O)R^{12}$, $NR^{10}(C=S)NR^{10}R^{11}$, $O(C=O)NR^{10}R^{11}$, $SO_2R^9$, $S(=O)_2OR^8$, and combinations thereof, wherein $R^8$, $R^9$, $R^{10}$, $R^{11}$, $R^{12}$ are independently selected from H, $C_1$-$C_6$ alkyl, $C_2$-$C_6$ alkenyls, $C_2$-$C_6$ alkynyls, and combinations thereof.

In certain embodiments $R^3$ and R have 10 or fewer, preferably 5 or fewer, carbon atoms, are cylic and/or comprise a ketone group.

In specific embodiments, each of $R^3$ and $R^4$ is independently selected from:

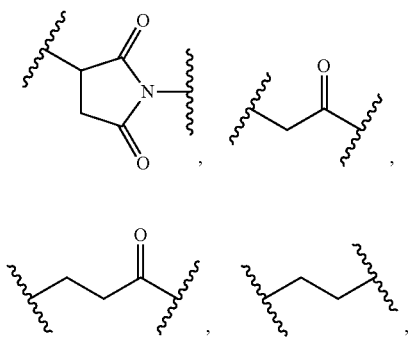

and derivatives thereof. In one embodiment, $R^3$ and $R^4$ are able to link 2 sulfhydryl groups and make light-heavy chains of an antibody more stable.

When $R^3$ or $R^4$ is null, $L^1$ or $L^2$ is conjugated directly to the targeting moiety.

$R^3$ and $R^4$ can be the same or different.

Only $R^3$ is

$R^3$ and $R^4$ can be the same.

In some embodiments, M is selected from, for example, C—$R^5$, C, N, B, P, Si—$R^5$, aromatics, heteroaryls, cycloalkyls, and (heterocyclyl)alkyls, $R^5$ is selected from H, $C_1$-$C_6$ alkyls, $C_2$-$C_6$ alkenyls, and $C_2$-$C_6$ alkynyls. In other embodiments, M is selected from the group consisting of

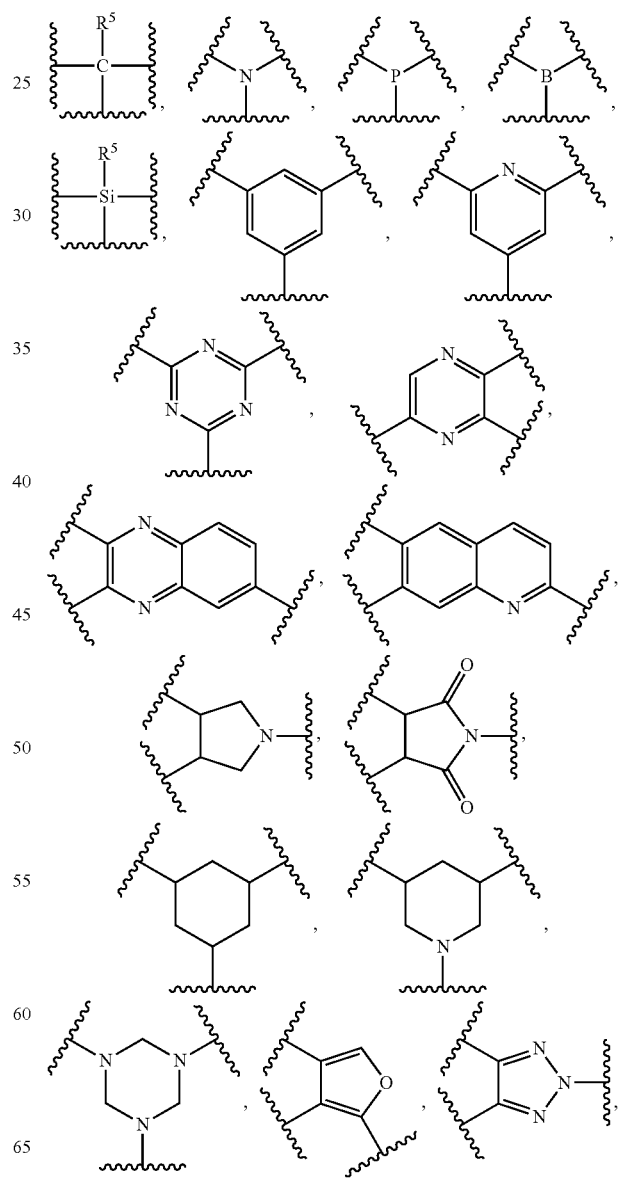

-continued

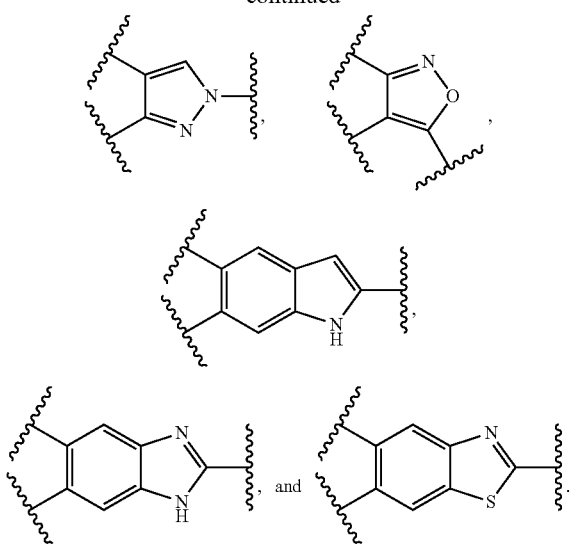

In certain embodiments, M is selected from

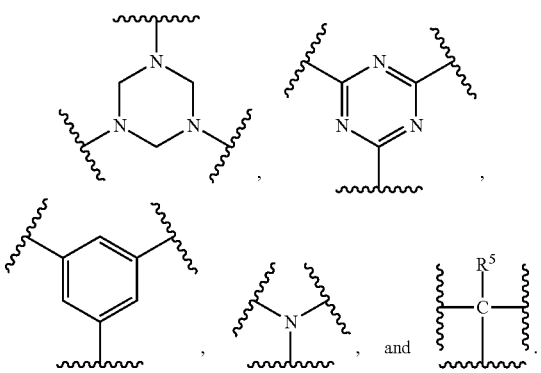

In some embodiments, Q is an active agent selected from the group consisting of tubulin binders, DNA alkylators, DNA intercalator, enzyme inhibitors, immune modulators, peptides, and nucleotides. "Drug" and "active agent" are used interchangeably herein.

In some embodiments, Q is selected from the group consisting of Maytansinoids, Auristatins, Calicheamicins, Doxorubicins, Duocarmycins, and PBDs.

In certain embodiments, Q is selected from MMAE, MMAF, PBD, DM1, and DM4. The active agent may be, for example, any of those that are disclosed in WO 2013085925A1, which is incorporated herein, it its entirety, by reference.

In some embodiments, each of the internal linking moieties $L^1$, $L^2$ is independently selected from $C_1$-$C_6$ alkyls, $C_2$-$C_6$ alkenyls, $C_2$-$C_6$ alkynyls, aromatics, heteroaryls, $C_3$-$C_9$ cycloalkyls, $C_3$-$C_9$ heterocyclyl, polyethylene glycol, O, S, $NR^6$, $C(=O)$, $C(=O)O$, $C(=O)NR^6$, $C=NR^6$, $C(=S)O$, $C(=S)NR^6$, $C(=S)S$, $NR^6(C=O)$, $NR^6(C=S)$ $NR^7$, $O(C=O)NR^6$, $S(=O)_2$ and any combination thereof.

Wherein, in this embodiment, $R^6$ and $R^7$ are independently selected from H, $C_1$-$C_6$ alkyls, $C_2$-$C_6$ alkenyls, and $C_2$-$C_6$ alkynyls.

In other embodiments, each of $L^1$ and $L^2$ is independently selected from:

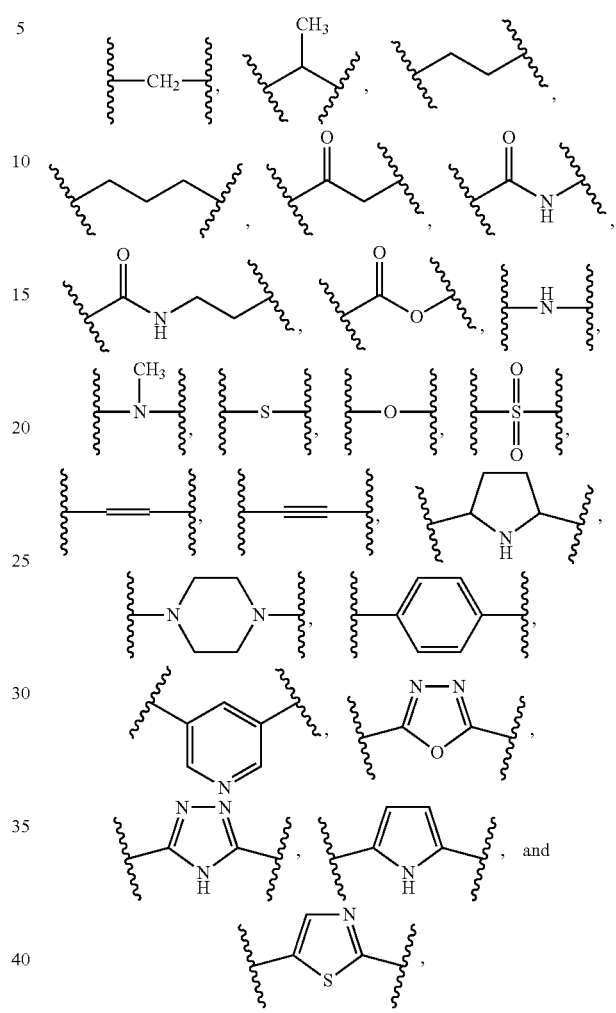

or is null.

In certain embodiments, each of $L^1$ and $L^2$ is independently selected from:

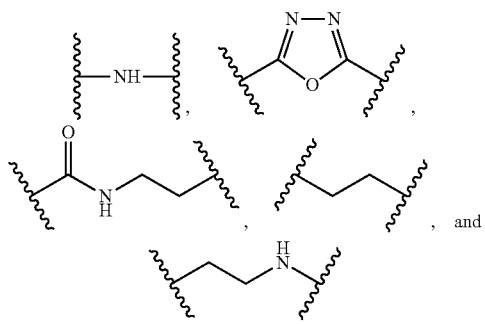

or is null.

L represents a linker, connecting drug Q to linking group M. In some embodiments, L includes a non-cleavable unit, in other embodiments, L includes a cleavable unit. The antibody drug conjugate may have one linker, two linkers, three linkers, four linkers, five linkers or six linkers.

In some embodiments, L is independently selected from $C_1$-$C_9$ alkyls, $C_2$-$C_9$ alkenyls, $C_2$-$C_9$ alkynyls, aromatics, heteroaryls, $C_3$-$C_9$ cycloalkyls, $C_3$-$C_9$ heterocyclyl, polyethylene glycol, O, S, $NR^8$, C(=O), C(=O)O, C(=O)$NR^8$, C=$NR^8$, C(=S)O, C(=S)$NR^8$, C(=S)S, $NR^8$(C=O), $NR^8$(C=S)$NR^9$, O(C=O)$NR^8$, S(=O)$_2$, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB and any combination thereof.

Wherein, in this embodiment, $R^8$ and $R^9$ are independently selected from H, $C_1$-$C_6$ alkyls, $C_2$-$C_6$ alkenyls, and $C_2$-$C_6$ alkynyls.

In some embodiments, L is null. When L is null, active agent Q is connected directly to M.

In some embodiments, L is independently selected from the group consisting of:

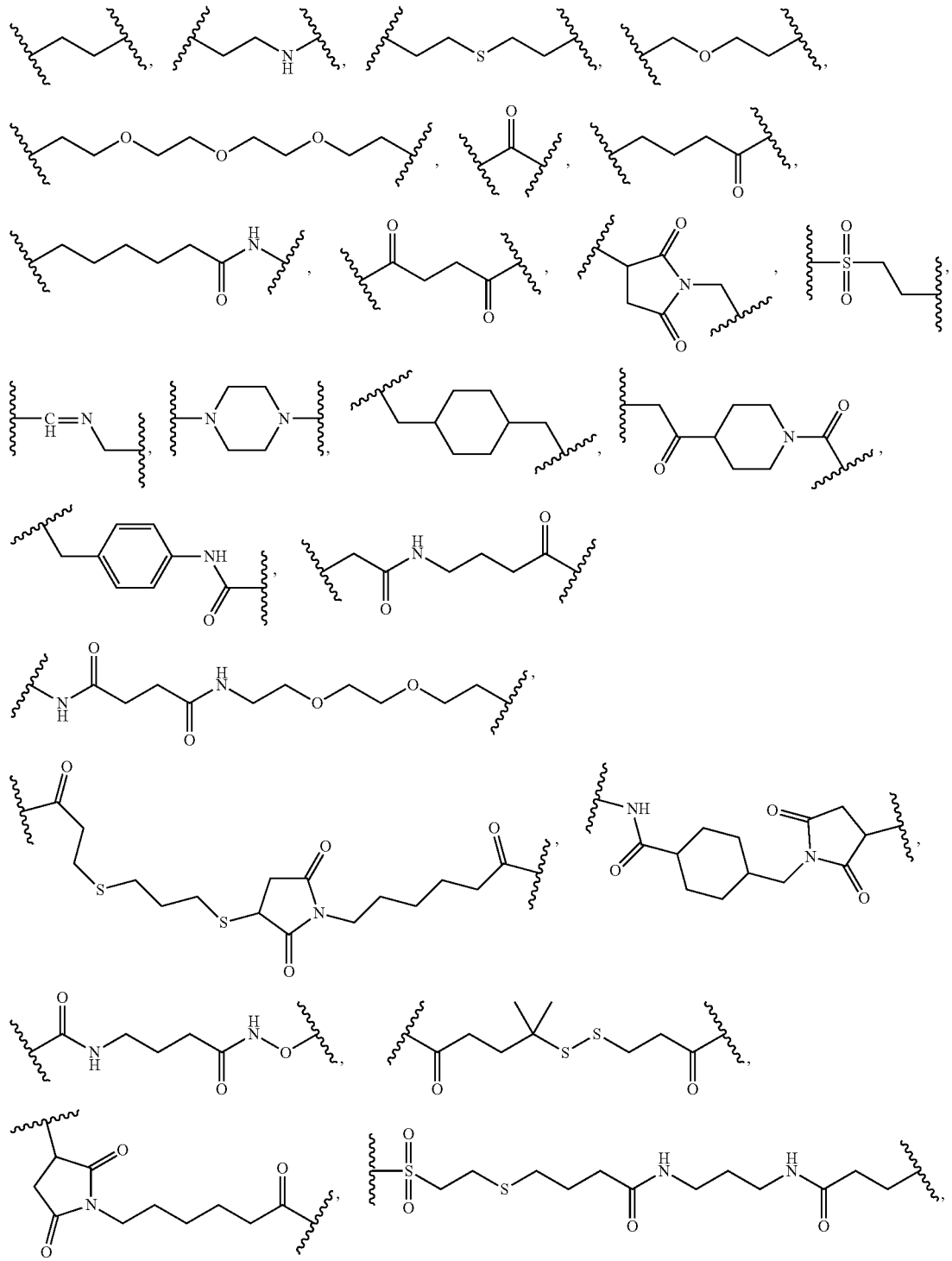

-continued
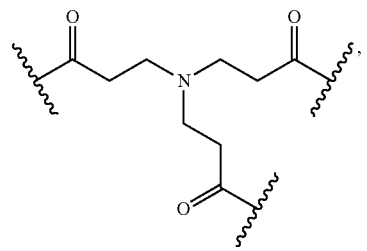
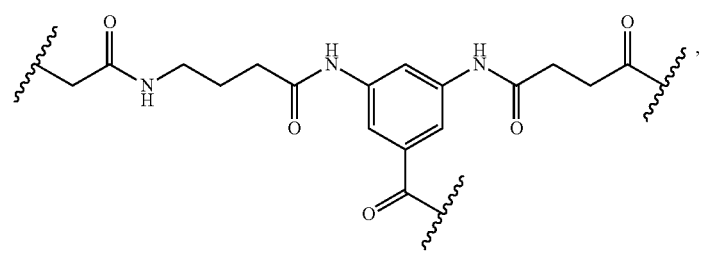
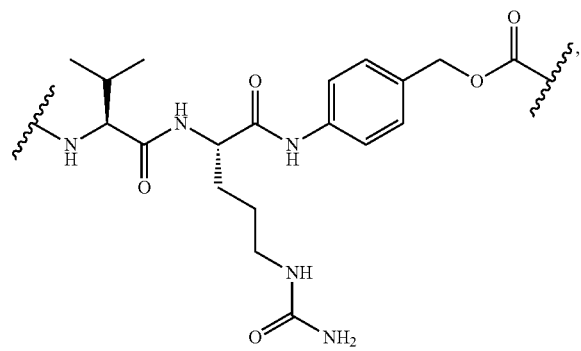
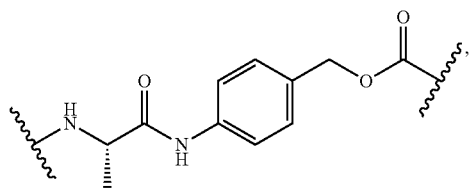
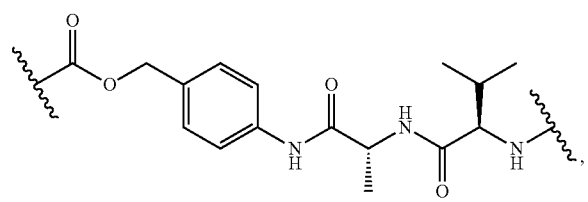
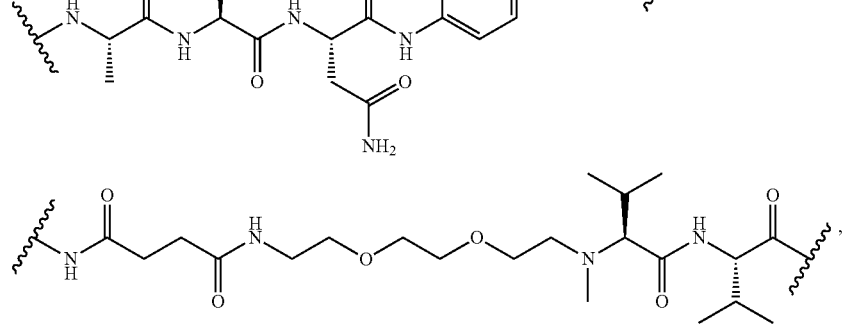
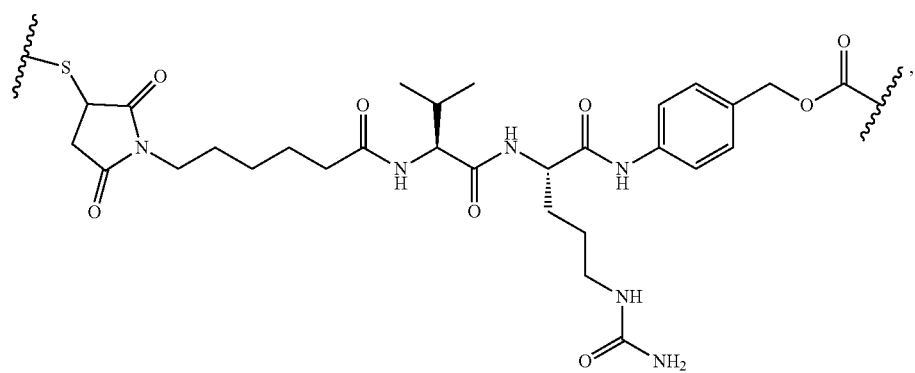

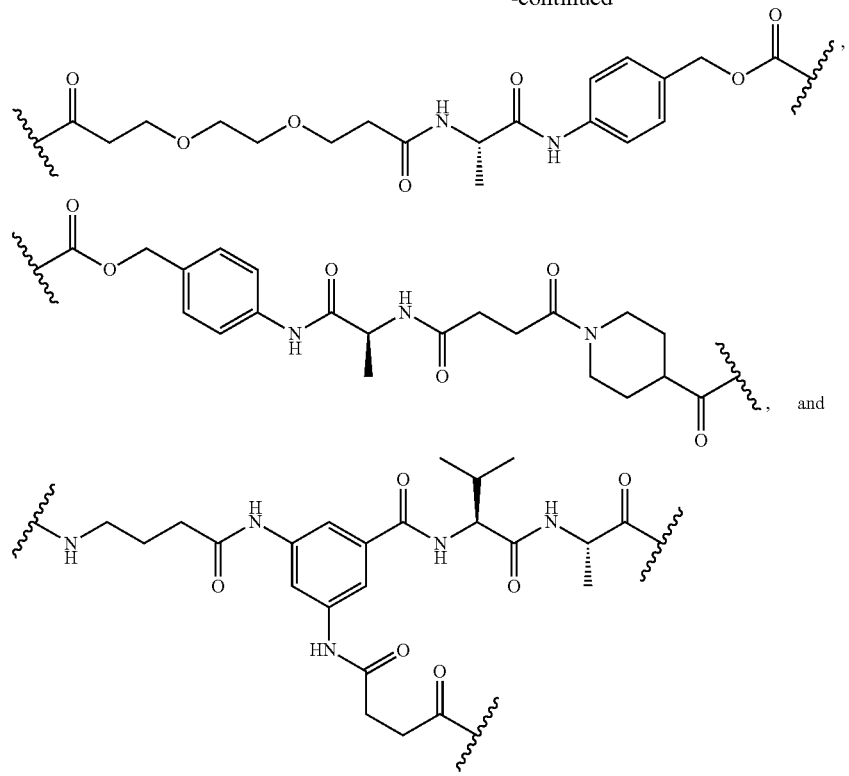
or is null.
In some embodiments, L is independently selected from the groups as follows:
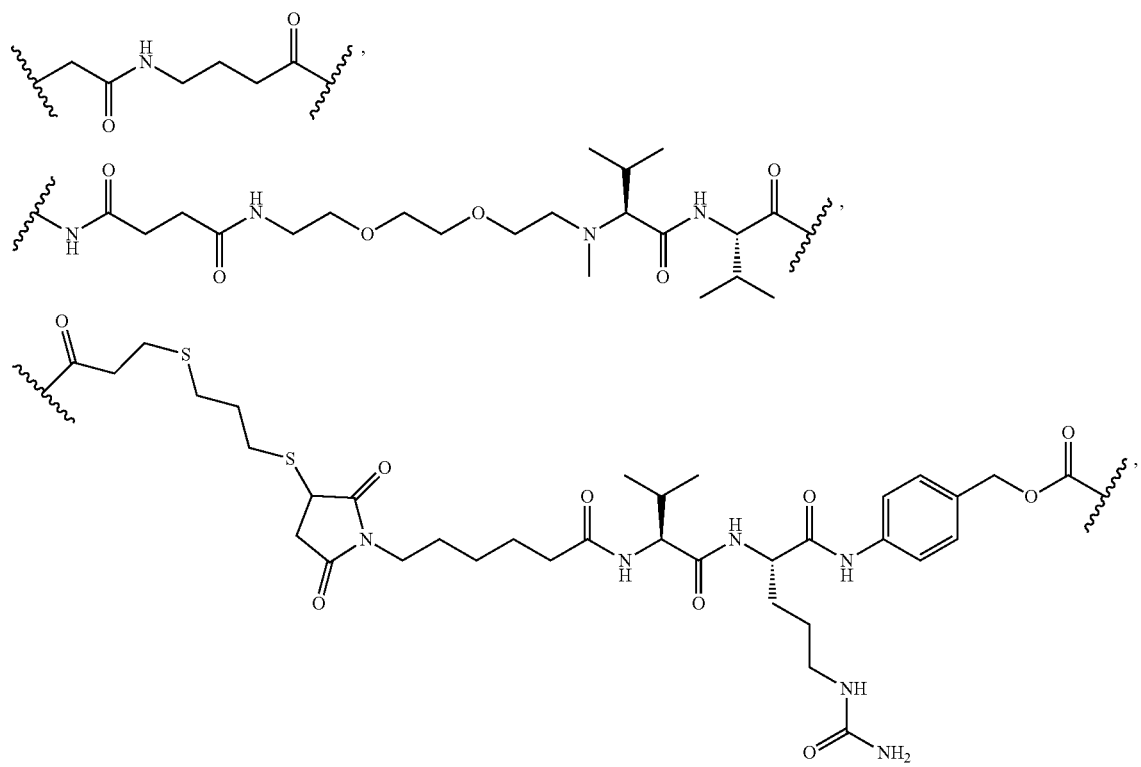

-continued

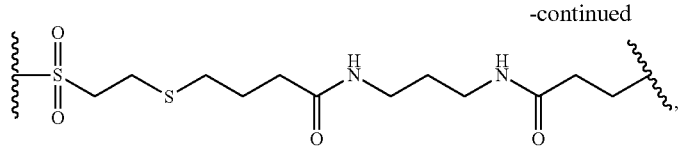

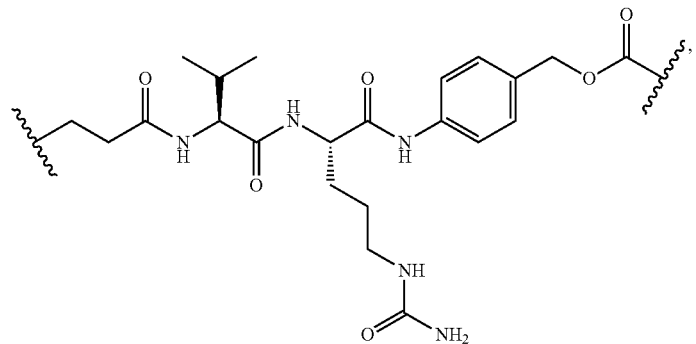

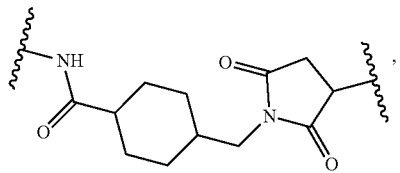

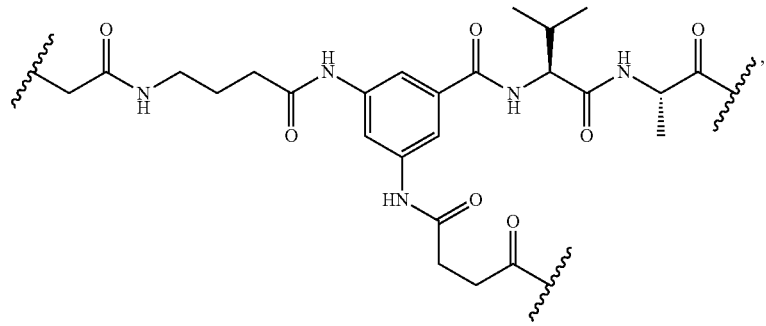

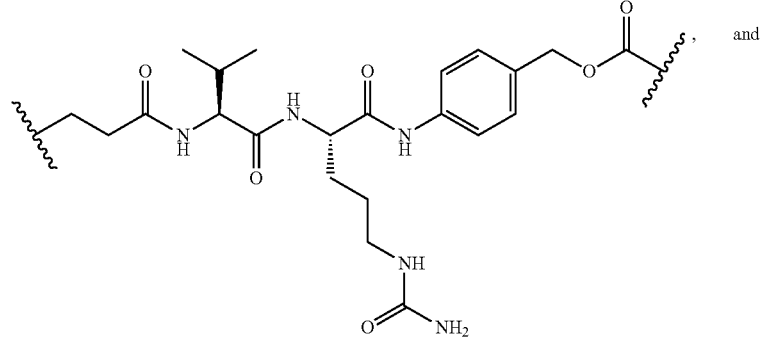

and

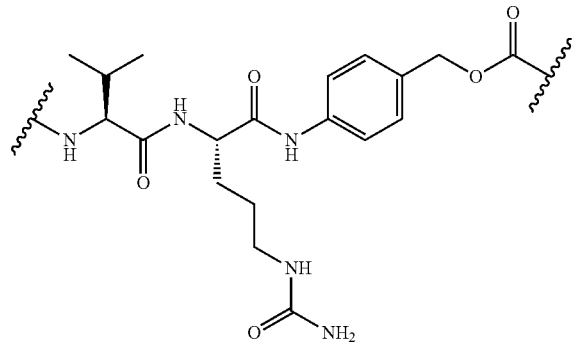

or is null.

A is a targeting moiety. In some embodiments, A is an antibody; an antibody fragment, surrogate or variant; a protein ligand; a protein scaffold; a peptide; or a small molecule ligand. The antibody fragment can be, for example, Fab, Fab', (Fab')₂, or scFv, Fv.

Examples of the tumor-associated antigens that can be targeted according to the subject invention include, but are not limited to, tumor-associated antigens (1) to (36) listed below. The name, alternative name, and GenBank accession number of each of the antigen examples is provided. Nucleic acid and protein sequences corresponding to these exemplary tumor-associated antigens can be found in public databases such as GenBank.

(1) BMPR1B (bone morphogenetic protein receptor type-1B. GenBank accession number NM_001203);

(2) E16 (LAT1, SLC7A5, GenBank accession number bandit_00: 3486);

(3) STEAP1 (six transmembrane epithelial antigen of prostate, GenBank accession number NM_012449);

(4) 0772P (CA 125, MUC16, GenBank accession number AF361486);

(5) MPF (MPF, MSLN, SMR, megakaryocyte strengthening factor, mesothelin, GenBank accession number NM_005823);

(6) Napi3b (NAP1-3B, NPTI1b, SLC34A2, solute carrier family 34 member (sodium phosphate) member 2, type II sodium-dependent phosphate transporter 3b, GenBank accession number NM_006424);

(7) Sema5b (FLJ10372, KIAA1445, Mm.42015, SEMA5B, SEMAG, semaphorin 5b Hlog, sema domain, seven thrombospondin repeats (type I and type I), a transmembrane domain (TM) and short cytoplasmic domain, (semaphorin) 5b, GenBank accession number AB040878);

(8) PSCA hlg (2700050C12Rik, C530008016Rik, RIKEN cDNA2700050C12, RIKENcDNA2700050C12 gene, GenBank accession number AY358628);

(9) ETBR (the endothelin B receptor, GenBank accession number AY275463);

(10) MSG783 (RNF124, Pseudo protein FLJ20315, GenBank accession number NM 017763);

(11) STEAP2 (HGNC_8639, IPCA-1, PCANAP I, STAMP I, STEAP2, STMP, prostate cancer-related genes I, prostate cancer-associated protein 1, six transmembrane epithelial antigen of prostate 2, six transmembrane prostate protein, GenBank accession number AF455138);

(12) TrpM4 (BR22450, FLJ20041, TRPM4, TRPM4B, transient receptor potential cation channel, subfamily M, member 4, GenBank accession number NM_017636);

(13) CRIPTO (CR, CR1, CRGF, CRIPTO, TDGFI, teratoma-derived growth factor, GenBank accession number NP_003203 or NM_003212);

(14) CD21 (CR2 (complement receptor type 2) or C3DR (C3d/EB virus receptor) or Hs.73792, GenBank accession number M26004);

(15) CD79b (CD79B, CD79 β, IGb (immunoglobulin related β), B29, GenBank accession number NM_000626);

(16) FcRH2 (IFGP4, IRTA4, SPAPIA (comprising phosphatase anchored proteins Ia of SH2 domains), SPAP1B, SPAP 1C, GenBank accession number NM_030764);

(17) HER2 (ErbB2, GenBank accession number M11730);

(18) NCA (CEACAM6, GenBank accession number M18728);

(19) MDP (DPEP1, GenBank accession number BC017023);

(20) IL20Ra (IL20Ra, ZCYT0R7, GenBank accession number AF184971);

(21) Brevican (BCAN, BEHAB, GenBank accession number AF229O53);

(22) EphB2R (DRT, ERK, HekS, EPHT3, Tyro5, GenBank accession number NM_004442);

(23) ASLG659 (B7h, GenBank accession number AX092328);

(24) PSCA (prostate stem cell antigen former body, GenBank accession number AJ297436);

(25) GEDA (GenBank accession number AY260763);

(26) BAFF-R (B cell activating factor receptor, BLyS receptor 3, BR3, GenBank accession number AF116456);

(27) CD22 (B-cell receptor CD22-B isoform, GenBank Accession No. AK026467);

(28) CD79a (CD79A, CD79a, immunoglobulin-related α, capable of covalent interactions with Ig (CD79B) and form a complex with IgM molecules on the surface, transduced B cells involved in B cell signal specific protein, GenBank accession number NP_001774.I);

(29) CXCR5 (Burkitt's lymphoma receptor 1, a G protein-coupled receptor chemokine-activated by CXCL13, plays a role in lymphocyte migration and humoral defense, possibly affects HIV-2 infection, AIDS, lymphoma, myeloma, and leukemia, GenBank accession number NP_001701.1);

(30) HLA-DOB (MHCII molecules of Beta subunit (Ia antigen) that binds peptides and presents them to CD4+ T cells in small lymphoid, GenBank accession number NP_002111.1);

(31) P2X5 (P2X purinergic receptor ligand-gated ion channel 5, the extracellular ATP-gated ion channels, may be involved in synaptic transmission and neurogenesis, the defect thereof may cause pathophysiology of idiopathic detrusor instability, GenBank accession number NP_002552.2);

(32) CD72 (B cell differentiation antigen CD72, Lyb-2, GenBank accession number NP_001773.1);

(33) LY64 (lymphocyte antigen 64 (RP105), leucine-rich repeat type I membrane proteins (LRR) family, regulates B cell activation, apoptosis, and loss of functions, may be involved in increased activities in patients with systemic lupus erythematosus, GenBank accession number NP_005573.1);

(34) FcRH1 (Fe 1 receptor-like protein, an immunoglobulin domain receptor putative Fc, comprises C2 type Ig-like and ITAM domains, may play a role in B cell differentiation, GenBank accession No. NP_443170.1);

(35) IRTA2 (immunoglobulin superfamily translocation associated receptor 2, putative immune receptor, may play a role in B cell development and lymphoma development; genetic disorders caused by a translocation occurs in some B the cell malignancies, GenBank accession number NP_112571.1);

(36) TENB2 (putative transmembrane proteoglycan, and relevant to growth factors EGF/hereguli family and follistatin, GenBank accession number AF179274).

In certain embodiments, A is a humanized monoclonal antibody that targets a tumor-associated antigen. The humanized antibody may, but is not limited to: Trastuzumab (anti-HER2), Pertuzumab (anti-HER2), Rituximab (anti-CD20), Alemtuzumab (anti-CD52), Bevacizumab (anti-VEGF), Adalimumab (anti-TNF-alpha), Cetuximab (anti-EGFR), Amatuximab (anti-mesothelin), Blinatumomab (anti-CD19), Brentuximab (anti-CD30), Certolizumab pegol (anti-TNF-alpha), Panitumumab (anti-EGFR), Nimotuzumab (anti-EGFR), Gemtuzumab (anti-CD33), Golimumab (anti-TNF-alpha), Ibritumomab (anti-CD20), Infliximab (anti-TNF-alpha), Ipilimumab (anti-CTLA-4), Ofatumumab (anti-CD20), and Tositumomab (anti-CD20).

In some embodiments, the antibody-drug conjugate has the following structure of Formula II:
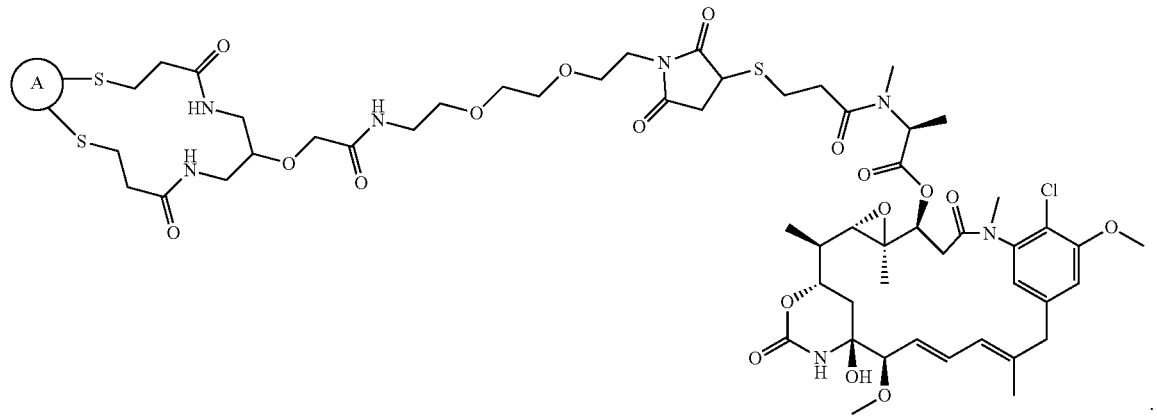
25
In some embodiments, the antibody-drug conjugate has the following structure of Formula II:
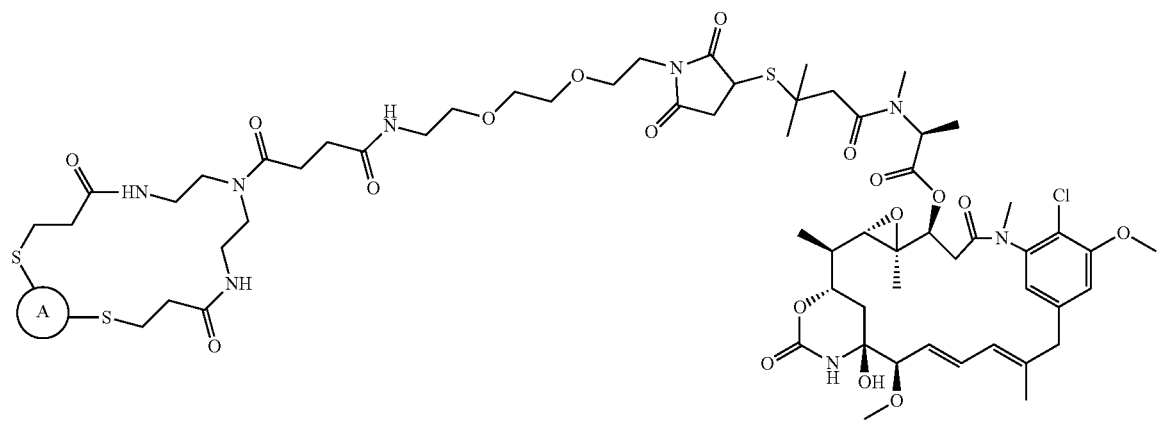
50
In some embodiments, the antibody-drug conjugate has the following structure of Formula II:
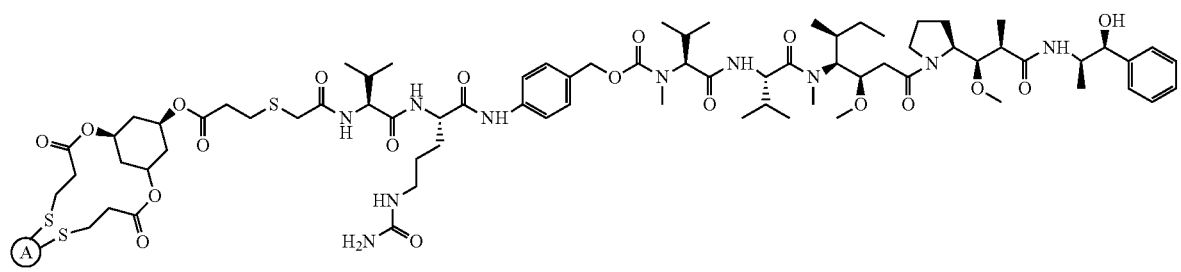

In some embodiments, the antibody-drug conjugate has the following structure of Formula II:

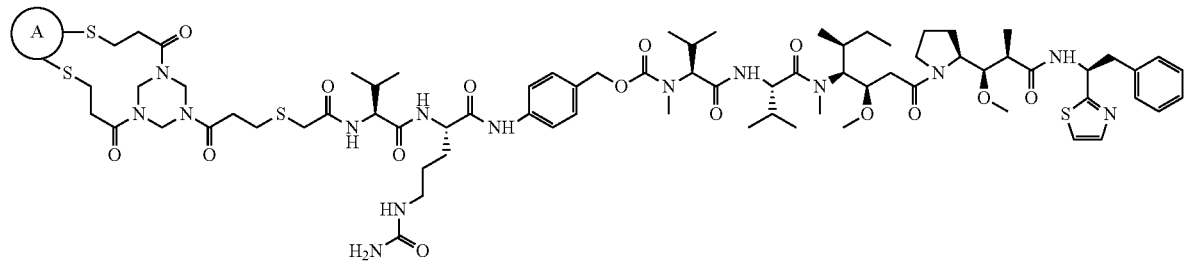

In some embodiments, the antibody-drug conjugate has the following structure of Formula II:

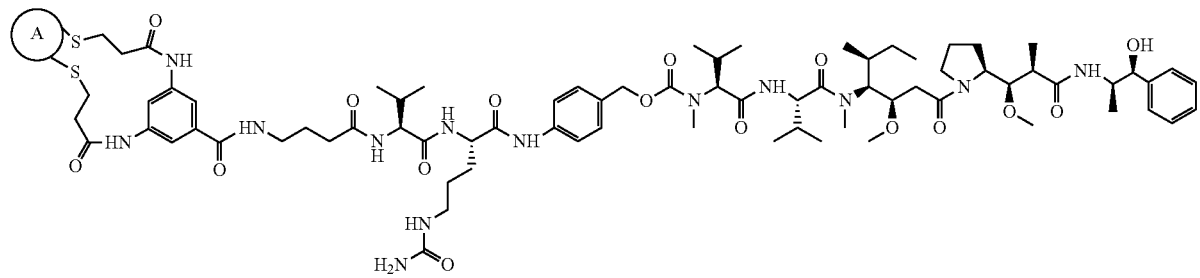

In some embodiments, the antibody-drug conjugate has the following structure of Formula II:

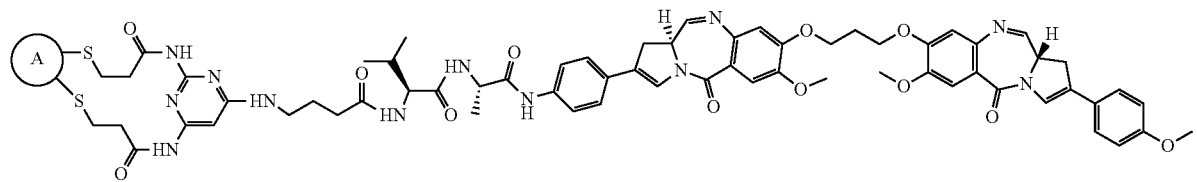

In some embodiments, the antibody-drug conjugate has the following structure of Formula II:

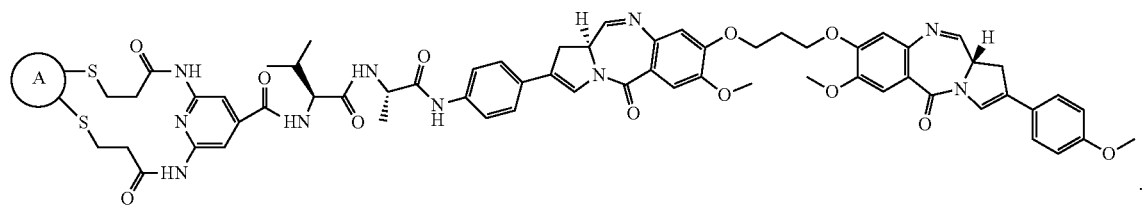

In some embodiments, the antibody-drug conjugate has the following structure of Formula II:
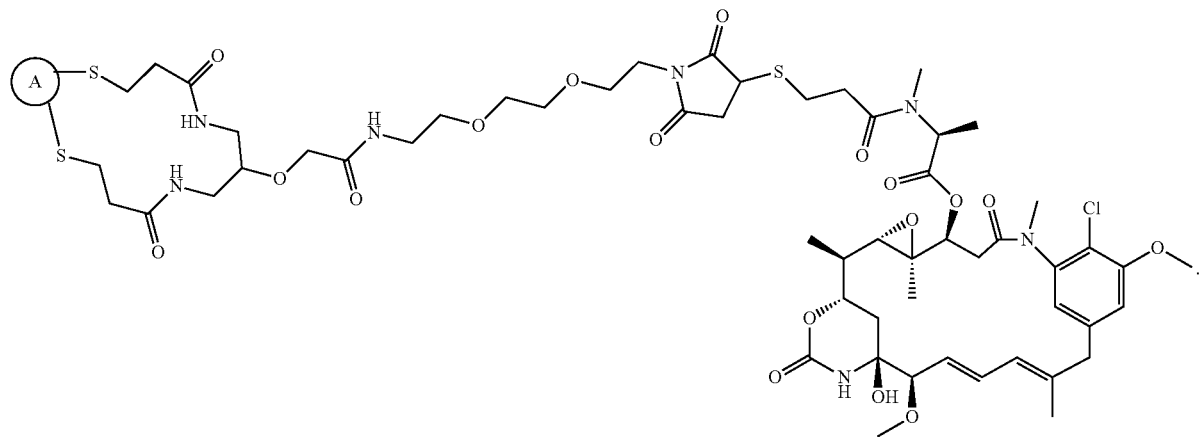
In some embodiments, the antibody-drug conjugate has the following structure of Formula II:
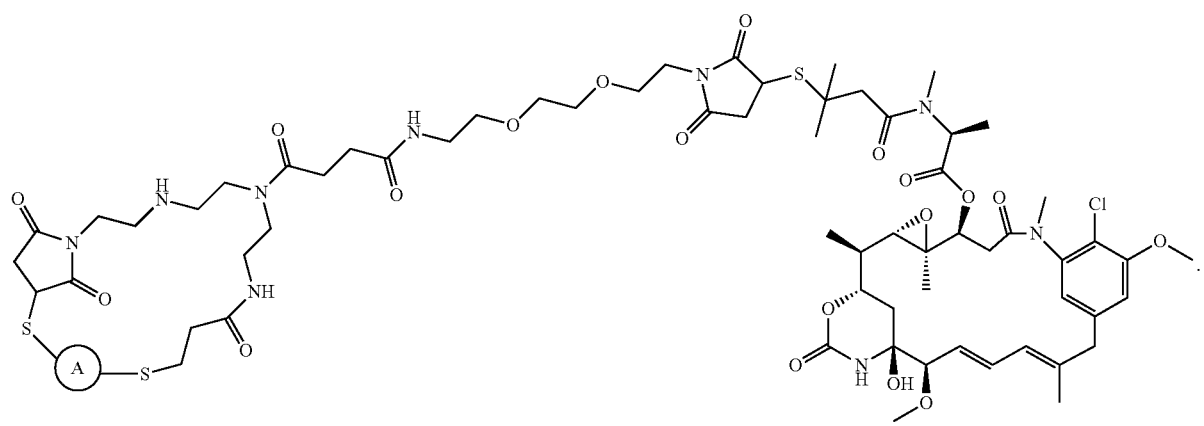
In some embodiments, the antibody-drug conjugate has the following structure of Formula II:
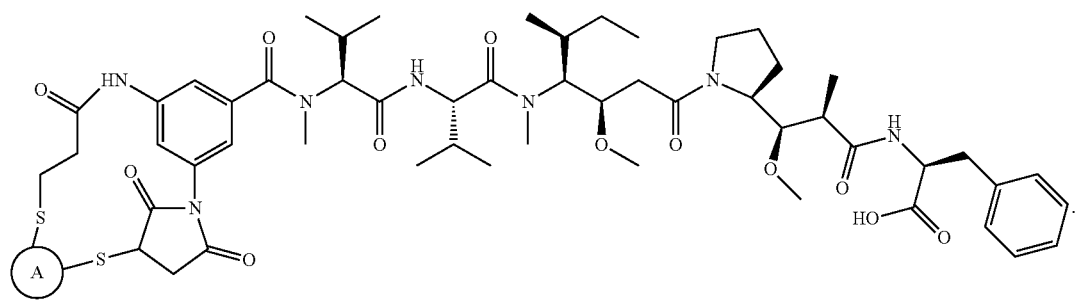

In some embodiments, the antibody-drug conjugate has the following structure of Formula II:

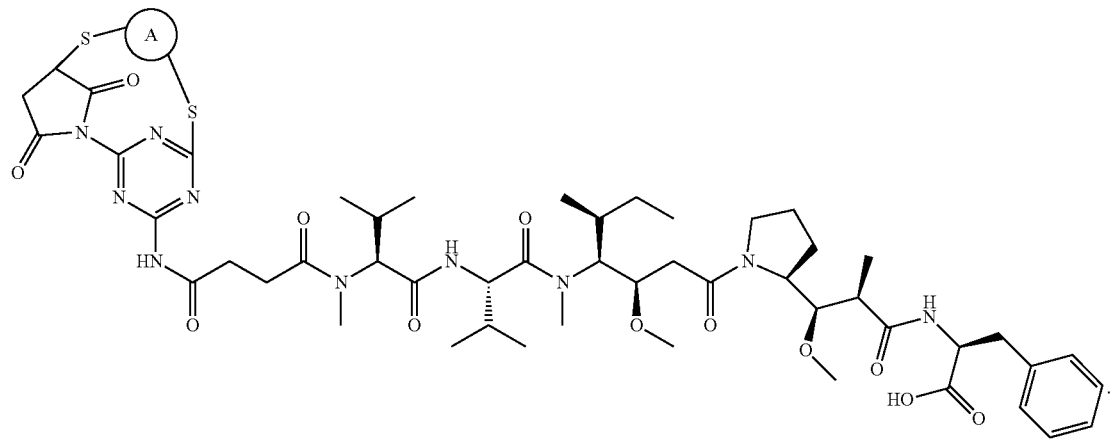

In some embodiments, the antibody-drug conjugate has the following structure of Formula II:

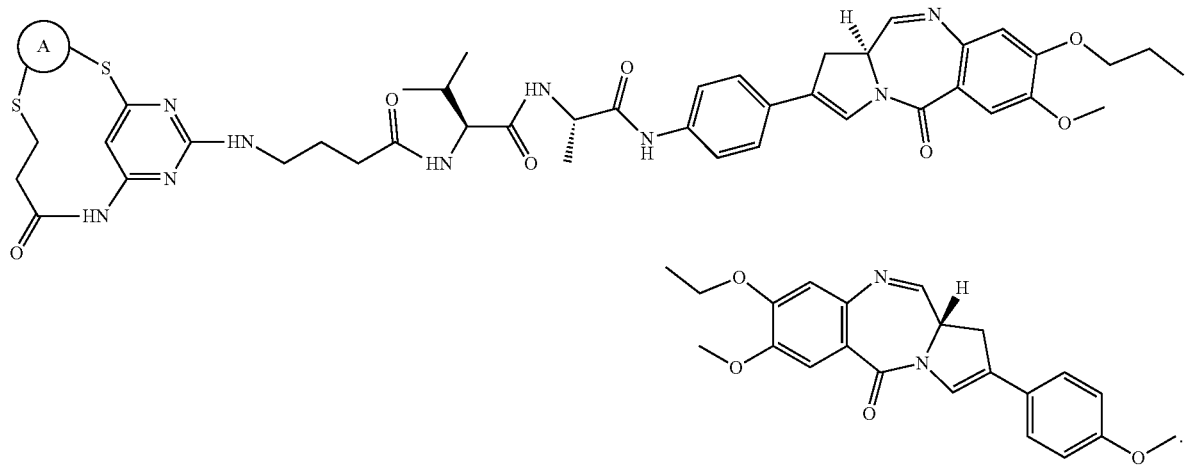

In certain embodiments, in the above compounds, A includes, but is not limited to trastuzumab.

Therapeutic Uses

In certain embodiments, the conjugates of the subject invention provide treatment for cancers including, but not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, oral cancer, liver cancer, bladder cancer, cancer of the urinary tract, hepatoma, breast cancer including, for example, HER2-positive breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain cancer, head and neck cancers, and associated metastases.

The conjugates of the subject invention can also be used to deliver active agents for the treatment of a variety of other conditions including, but not limited to, inflammatory disorders, autoimmune disorders, disorders of the nervous system, and cardiovascular disorders.

Diagnostic Uses

In other embodiments, the conjugate of the subject invention comprises a detectable entity as the active agent. The detectable entity may be, for example, a visualization agent. The agent can be a synthetic or natural product, and capable of reflecting or emitting light at a wavelength detectable by suitable imaging and/or diagnostic equipment such as a microscope. Non-limiting examples of suitable visualization agents include organic dyes, food dyes, and fluorescence dyes.

Thus, in one embodiment the subject invention provides a diagnostic method that involves contacting a sample, suspected of having an analyte of interest, with the antibody-drug conjugate of the subject invention, wherein the target moiety selectively binds to the analyte of interest and Q is a detectable entity and/or is an entity to which one or more additional entities will bind wherein said one or more additional entities are, themselves, detectable entities, and wherein said method further comprises analyzing the sample to determine the presence of a detectable entity, which presence would be indicative of the presence of the analyte of interest. In one embodiment, the analyte is HER2, or other antigen associated with cancer. The method could be carried out either in vivo or in vitro.

Biological Activity of the Conjugates

The conjugates of the subject invention herein can be evaluated for efficacy and toxicity using known methods. For example, the toxicology of a particular compound, or of a subset of the compounds, sharing certain chemical moieties, can be established by determining in-vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, can be determined using known methods.

The efficacy of a particular compound can be established using art-recognized methods, such as in-vitro methods, animal models, or human clinical trials. Art-recognized in-vitro models exist for nearly every class of condition, including the conditions abated by the compounds disclosed herein, including cancer, cardiovascular disease, and various immune system dysfunction, and infectious diseases. Similarly, acceptable animal models can be used to establish efficacy of chemicals to treat such conditions. When selecting a model to determine efficacy, a person of ordinary skill in the art can be guided by the state of the art to choose an appropriate model, dose, and route of administration, and regimen.

The complexes provided herein may be assayed for binding affinity to, and specificity for, the desired target by any of the methods conventionally used for the assay of antibodies. The complexes may be assayed for efficacy as anti-cancer agents by any of the methods conventionally used for the assay of cytostatic/cytotoxic agents, such as assays for potency against cell cultures, xenograft assays, and the like.

A person of ordinary skill in the art having the benefit of the current disclosure will have no difficulty, considering that skill and the literature available, in determining suitable assay techniques; from the results of those assays, in determining suitable doses to test in humans as anticancer agents, and, from the results of those tests, in determining suitable doses to use to treat cancers in humans.

Formulations and Administration

The compositions of the subject invention comprise, in addition to the complexes described herein, a physiologically acceptable carrier and/or diluent allowing the transport of the complexes to the target within the animal after administration. The carrier and/or diluent can generally be any suitable medium by which the desired purpose is achieved and that does not affect the conjugates' capability to be directed to the desired target and to transport the active agent to this target for the desired effect. Particularly, the carrier and/or diluent should not deteriorate the pharmacological potency of the active agent and the capability of the complex to be directed to a desired target within, or on, the animal body. Preferably, said carrier and/or diluent is/are selected from water, physiologically acceptable aqueous solutions containing salts and/or buffers and any other solution acceptable for administration to an animal. Such carriers and diluents are well known to a person skilled in this field and can be, for example, distilled water, de-ionized water, pure or ultrapure water, saline, phosphate-buffered saline (PBS), solutions containing usual buffers which are compatible with the other components of the drug targeting system etc.

The compositions can be administered to a subject by methods including, but not limited to, (a) administration through oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the present embodiment into contact with living tissue; and (f) administration via controlled released formulations, depot formulations, and infusion pump delivery.

As further examples of such modes of administration and as further disclosure of modes of administration, disclosed herein are various methods for administration of the disclosed compounds and pharmaceutical compositions including modes of administration through intraocular, intranasal, and intraauricular pathways.

In specific embodiments, the complexes of this invention can be formulated as solutions for intravenous administration, or as lyophilized concentrates for reconstitution to prepare intravenous solutions (to be reconstituted, e.g., with normal saline, 5% dextrose, or similar isotonic solutions). They will typically be administered by intravenous injection or infusion. A person of ordinary skill in the art of pharmaceutical formulation, especially the formulation of anti-cancer antibodies, will have no difficulty, considering that skill and the literature available, in developing suitable formulations.

EXAMPLES
Following are examples that illustrate procedures for practicing the invention. These examples should not be construed as limiting.
Example I Synthesis of Linker-Active Agent Conjugates
Example I-1 Synthesis of Compound 9
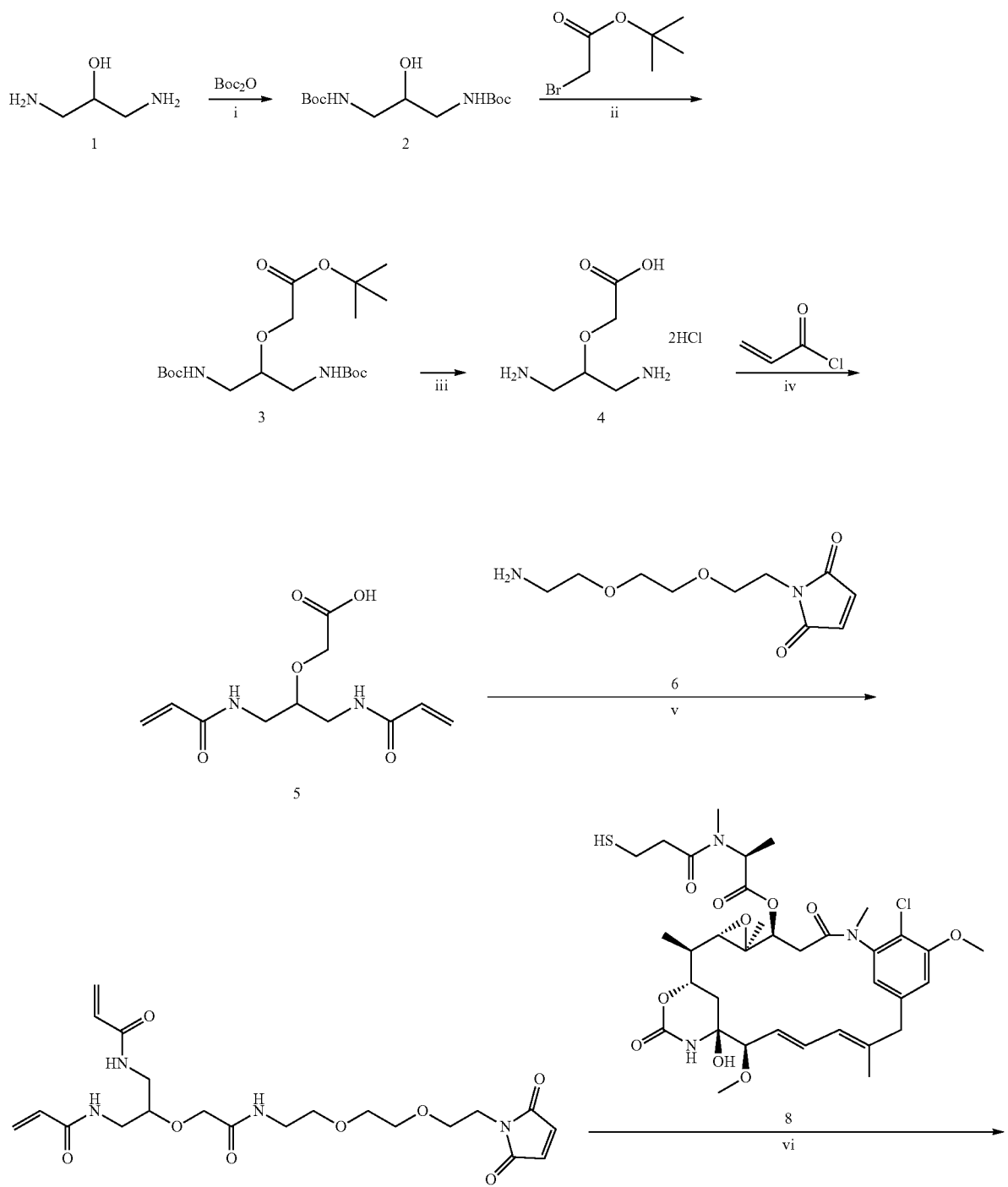

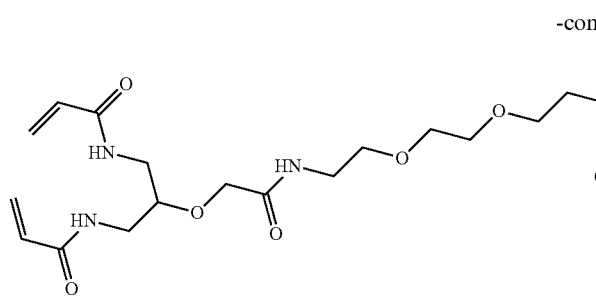
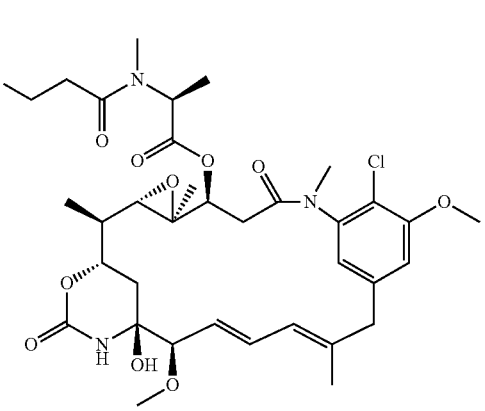

9 i) Et₃N, MeOH R.T., 2 h; ii) NaH, THF, R.T., 5 h; iii) Hydrochloric acid, 1,4-dioxane, R.T., 16 h; iv) NaHCO₃, H₂O/THF, R.T., 3 h; v) HOBt, DIC, DIPEA, DMF, R.T., 12 h; vi) Et₃N, CH₂Cl₂, R.T., 2 h.

Synthesis of Compound 2

A solution of 1,3-diamino-2-propanol (3.15 g, 0.035 mol) and Et₃N (4.85 mL, 0.035 mol) in methanol (120 mL) was heated to 45° C. To the solution, (Boc)₂O (17.05 g, 0.078 mol) in methanol (80 mL) was dropwise added slowly. The reaction solution was stirred at 45° C. for 30 min. After additional stirring at room temperature for 1.5 h, the solvent was removed under reduced pressure. The crude product was extracted with diethyl ether (200 mL×3) and dried over sodium sulfate to yield the compound 2 (9.94 g, 97.8%) as a white powder. LC-MS m/z (ES⁺), 291.19 (M+H)⁺.

Synthesis of Compound 3

Tert-butylbromoacetate (5.41 mL, 33.5 mmol) was added to a solution of Compound 2 (3.89 g, 13.4 mmol) in dry THF (40 mL) at room temperature. To the solution, sodium hydride (60% dispersion in mineral oil, 2.42 g, 60.5 mmol) was subsequently added. The mixture was filtrated after 5 hours. The filtrate was evaporated and the residue was purified by column chromatography (petroleum ether:ethyl acetate=10:1 to 5:1) to give the product 3 (3.96 g, 73.1%) as a white solid. LC-MS m/z (ES⁺), 405.26 (M+H)⁺.

Synthesis of Compound 4

5 mL of hydrochloric acid was added to a stirred solution of compound 3 (1.0 g, 2.5 mmol) in 1,4-dioxane (10 mL) at room temperature. The reaction was completed after 16 hours. Then the solvent was removed to give a white crude product (384.2 mg, 69.8%). The product 4 could be used in the next step without purification. LC-MS m/z (ES⁺), 221.05 (M+H)⁺.

Synthesis of Compound 5

Acryloyl chloride (267 µL, 3.3 mmol) was added to a solution of compound 4 (242.1 mg, 1.1 mmol) in saturated sodium bicarbonate solution/THF (v/v=1:1, 20 mL) at 0° C. The resulting mixture was vigorously stirred at 0° C. After 10 minutes, the solution was allowed to raise to room temperature and reacted for 3 hours. The mixture was acidified with hydrochloric acid to adjust pH<4. The mixture was extracted with ethyl acetate (50 mL×2). The organic layers were combined and washed with saturated sodium chloride solution (40 mL), dried over anhydrous magnesium sulfate, filtered and removed the solvent. The solid residue was purified by prep-HPLC to give product 5 as a gray powder (196.0 mg, 69.6%). LC-MS m/z (ES⁺), 257.12 (M+H)⁺.

Synthesis of Compound 7

To a stirred solution of compound 5 (25.6 mg, 0.10 mmol) and DIPEA (16.5 µL, 0.10 mmol) in dry DMF (6 ml) at 0° C. was added HOBt (14.9 mg, 0.11 mmol) and DIC (13.9 mg, 0.11 mmol). After 15 minutes, compound 6 (20.5 mg, 0.09 mmol) was added to the solution. The reaction mixture was allowed to warm to room temperature and stirred overnight. The mixture was diluted with water (10 mL) and extracted with ethyl acetate (20 mL×3). The combined organic layers were dried over anhydrous magnesium sulfate and the solvent was removed in vacuo. The crude product was purified by column chromatography (petroleum ether: ethyl acetate=3:1) to yield compound 7 as a white solid (24.3 mg, 62.6%). LC-MS m/z (ES⁺), 467.22 (M+H)⁺.

Synthesis of Compound 9

Compound 7 (140.1 mg, 0.3 mmol) was dissolved in 5 mL CH₂Cl₂ and cooled to 0° C. in an ice bath. Et₃N (1 mg, 0.01 mmol) and the compound 8 (73.7 mg, 0.1 mmol) were added to the resulting mixture and left to stir for 30 minutes. The solution was allowed to warm to room temperature and stirred for another 1.5 hours. The solvent was removed under reduced pressure, and the solid residue was purified by pre-HPLC to give compound 9 as a white powder (90 mg, 74.8%). LC-MS m/z (ES⁺), 1204.49 (M+H)⁺.

Example I-2 Synthesis of Compound 17
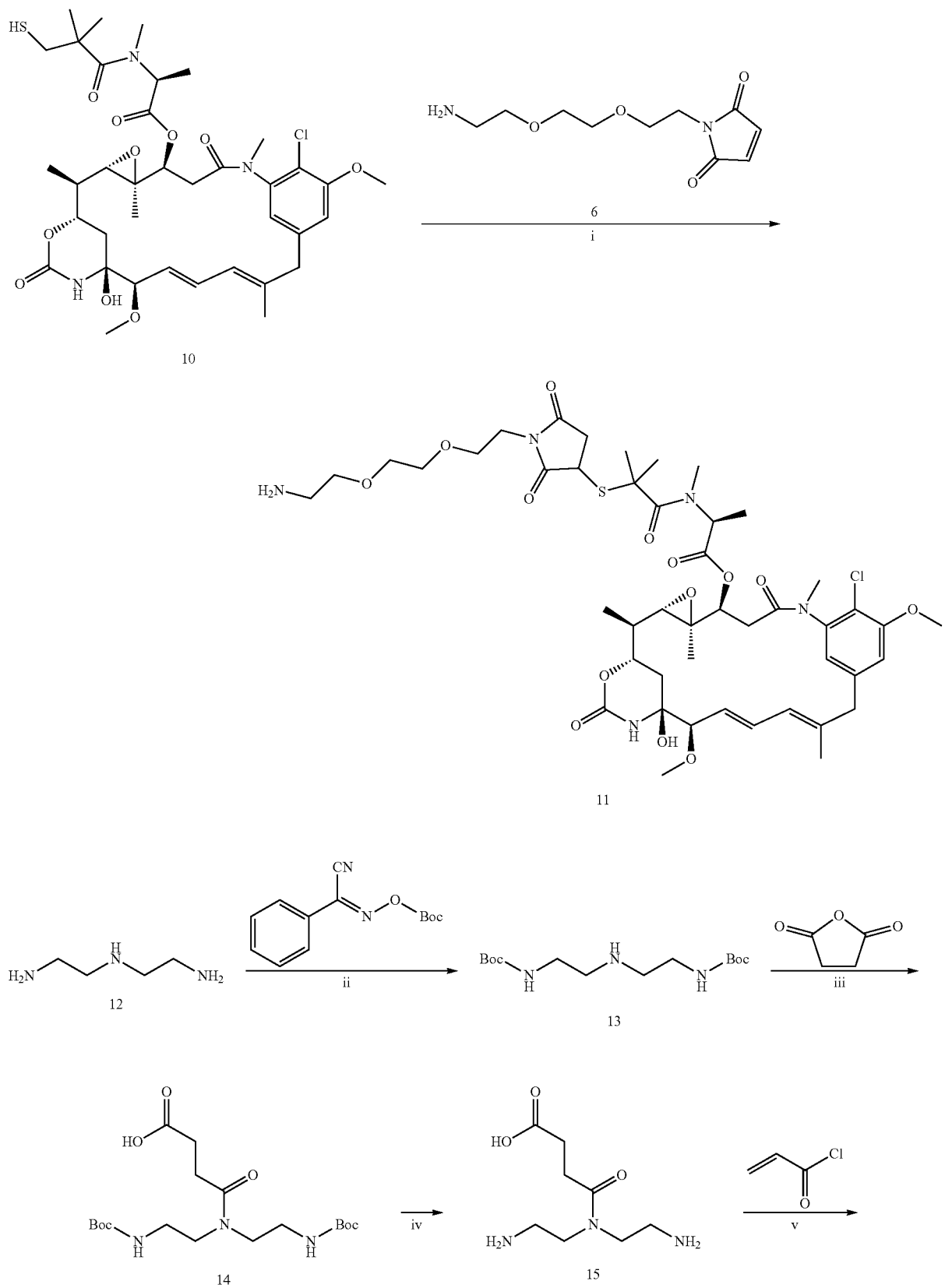

-continued

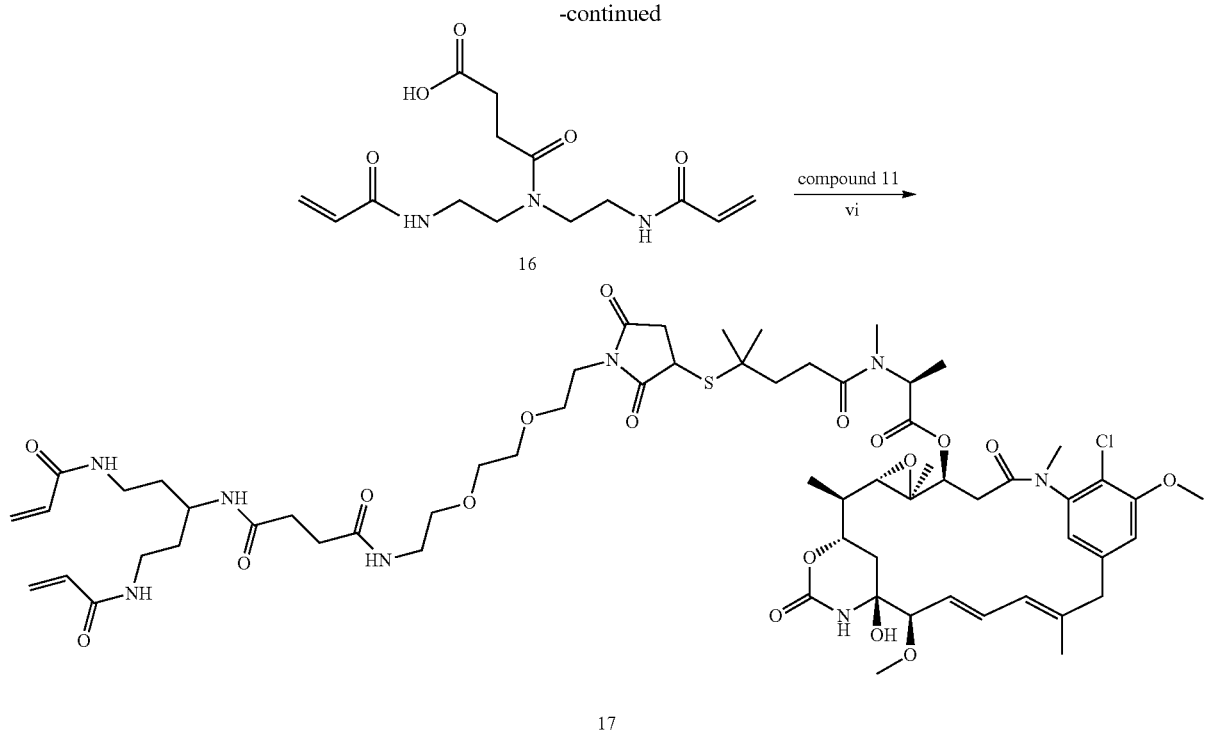

17 i) Et₃N, CH₂Cl₂, R.T., 5 h; ii) Et₃N, THF, R.T., 4 h; iii) CH₂Cl₂, R.T., 12 h; iv) TFA, CH₂Cl₂, R.T., 3 h; v) K₂CO₃, H₂O/EtOAc, R.T., 5 h;
vi) HOBt, DIC, DIPEA, DMF, R.T., 24 h.

Synthesis of Compound 11

Compound 10 (263.3 mg, 1.15 mmol) was dissolved in CH$_2$Cl$_2$ (15 mL), Et$_3$N (5.9 µL, 0.04 mmol) and the compound 6 (300.1 mg, 0.39 mmol) was added to the resulting mixture at 0° C. The solution was allowed to warm to room temperature and maintained for 5 hours. The solvent was removed in vacuo and the crude product was purified by prep-HPLC to yield compound 11 (193.2 mg, 49.7%) as a white solid. LC-MS m/z (ES$^+$), 994.43 (M+H)$^+$.

Synthesis of Compound 13

To a mixture of compound 12 (0.45 g, 4.2 mol) and Et$_3$N (8 mL, 0.06 mol) in THF (15 mL), a solution of 2-(tert-Butoxycarbonyloxyimino)-2-phenylacetonitrile (2.1 g, 8.3 mol) in THF (30 mL) was added dropwise at 0° C. Following complete addition, the solution was allowed to warm to room temperature and left to stir for 4 hours. The reaction mixture was concentrated to oil under reduced pressure and CH$_2$Cl$_2$ (50 mL) was added. The mixture was washed with sodium hydroxide (5%, 30 mL) and brine (30 mL). The organic layer was dried over sodium sulfate and concentrated under reduced pressure. The crude product was purified by column chromatography (silica gel, MeOH:CH$_2$Cl$_2$=1:10, v/v) to give compound 13 as a yellow oil (803.1 mg, 60.7%). LC-MS m/z (ES$^+$), 304.22 (M+H)$^+$.

Synthesis of Compound 14

Succinic anhydride (265.2 mg, 2.65 mmol) was added to a solution of compound 13 (800.1 mg, 2.65 mmol) in CH$_2$Cl$_2$ (10 mL). The mixture was stirred at room temperature overnight and then concentrated to oil under reduced pressure. The crude product was purified by column chromatography (silica gel, MeOH:CH$_2$Cl$_2$=1:8, v/v) to give compound 14 (506.5 mg 47.6%) as a gray oil. LC-MS m/z (ES$^+$), 404.24 (M+H)$^+$.

Synthesis of Compound 15

Compound 14 (503.5 mg 1.25 mmol) was dissolved in CH$_2$Cl$_2$ (10 mL) along with trifluoroacetic acid (2 mL). The solution was allowed to react for 3 hours at room temperature. The solvent was removed under reduced pressure to yield compound 15 as a gray oil (190.2 mg, 75.1%) without further purification. LC-MS m/z (ES$^+$), 204.13 (M+H)$^+$.

Synthesis of Compound 16

To a mixture of potassium carbonate (68.3 mg, 0.5 mmol) in water (5 mL) and compound 15 (67.2 mg, 0.33 mmol) in ethyl acetate (10 mL), a solution of acryloyl chloride (53.6 µL, 0.67 mmol) in ethyl acetate (10 mL) was added dropwise at 0° C. The resulting mixture was stirred at 0° C. in an ice bath for 10 minutes and then allowed to react at room temperature for 5 hours. The mixture was acidified with hydrochloric acid to adjust pH<5. The mixture was extracted with ethyl acetate (20 mL×2). The organic layers were combined and washed with saturated sodium chloride solution (20 mL), dried over anhydrous magnesium sulfate, filtered and the solvent removed. The solid residue was purified by column chromatography (MeOH:CH$_2$Cl$_2$=10:1) to give product 16 as a yellow oil (63.1 mg, 61.7%). LC-MS m/z (ES$^+$), 312.15 (M+H)$^+$.

Synthesis of Compound 17

Compound 16 (22.2 mg, 0.07 mmol), HOBt (9.7 mg 0.07 mmol) and DIC (11 µL, 0.07 mmol) were dissolved in 8 mL DMF and cooled to 0° C. in an ice bath. Subsequently, compound 11 (59.1 mg, 0.06 mmol) and DIPEA (12.4 µL, 0.07 mmol) were added to the mixture. The solution was allowed to warm to room temperature and left to react for 24 hours. The resulting mixture was concentrated and purified by prep-HPLC to yield compound 17 (11.3 mg, 39.5%) as a white solid. LC-MS m/z (ES$^+$), 1287.56 (M+H)$^+$.

Example I-3 Synthesis of Compound 25
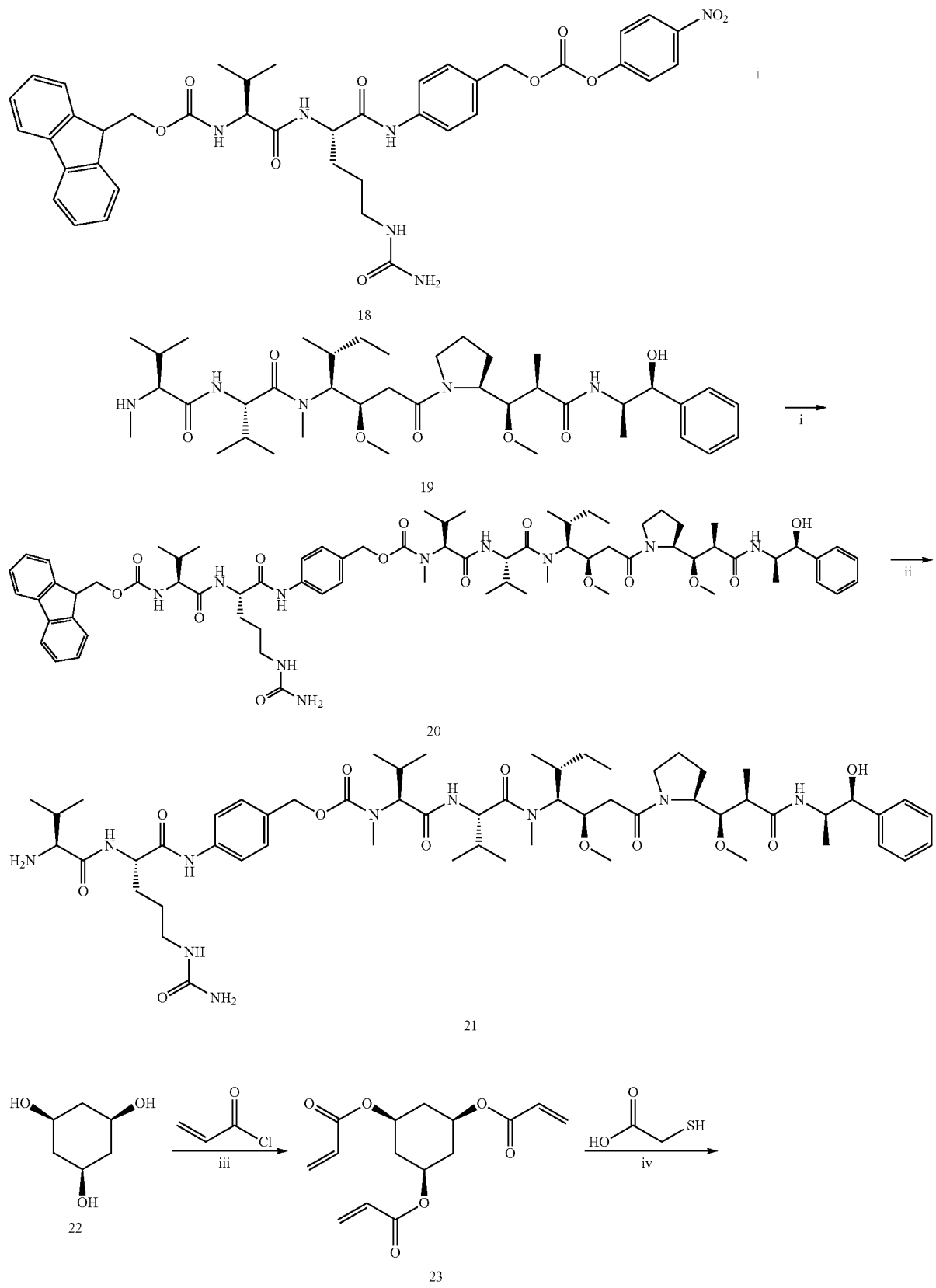

-continued

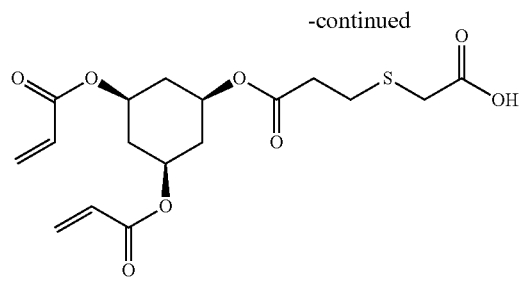

24

→ Compound 21
  v

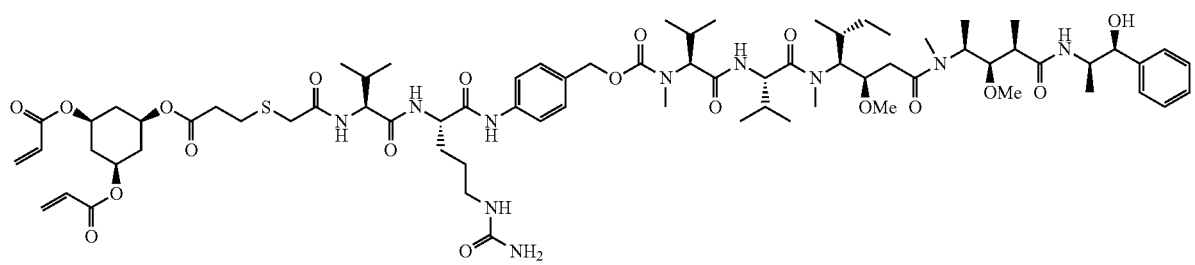

25 i) HOBt, DIPEA, Pyridine, DMF, R.T., 32 h ii) DEA, DMF, R.T., 2 h; iii) Et₃N, CH₂Cl₂, R.T., 4 h; iv) Et₃N, CH₂Cl₂, R.T., 12 h;
v) EDCI, HOBt, DIPEA CH₂Cl₂, R.T., 24 h.

Synthesis of Compound 20

To a stirred solution of 18 (191.6 mg, 0.25 mmol) in dry DMF (15 mL) at 0° C. under nitrogen, HOBt (33.8 mg, 0.25 mmol) and compound 19 (197.3 mg, 0.26 mmol) was added. After 15 minutes, pyridine (3 mL) and DIPEA (52.4 µL, 0.30 mmol) were added and reacted for 30 minutes at 0° C. Then the reaction mixture was allowed to warm to room temperature and stirred for 3 hours. The mixture was replenished DIPEA (52.4 µL, 0.30 mmol) and reacted for 32 hours. Upon completion of the reaction, the solvent was removed under reduced pressure. The residue was purified by column chromatography (MeOH:CH₂Cl₂=20:1) to give the compound 20 (126.4 mg, 37.5%) as a white solid. LC-MS m/z (ES⁺), 1344.77 (M+H)⁺.

Synthesis of Compound 21

Diethylamine (4 mL, 38.8 mmol) was added to a solution of compound 20 (126.4 mg, 0.1 mmol) in DMF (8 mL) at room temperature. After stirring for 2 hours, the solvent was removed under reduced pressure to give a crude product 21 (104.1 mg, 99%/a). The product could be used in the next step without purification. LC-MS m/z (ES⁺), 1123.72 (M+H)⁺.

Synthesis of Compound 23

A solution of acryloyl chloride (7.31 mL, 90.00 mmol) in dry CH₂Cl₂ (50 mL) was added dropwise to a mixture of compound 22 (2.64 g, 20.00 mmol) and Et₃N (16.60 mL; 120.00 mmol) in dry CH₂Cl₂ (60 mL) at 0° C. under argon. The mixture was allowed to raise to room temperature and reacted for 4 hours. Then the mixture was treated with saturated sodium bicarbonate solution (150 mL) and brine (150 mL), and extracted with CH₂Cl₂ (150 mL×3). The combined organic layers were dried over anhydrous magnesium sulfate and the solvent was removed in vacuo. The crude product was purified by column chromatography (petroleum ether:ethyl acetate=10:1) to afford the compound 23 as a white solid (4.88 g, 83.0%). LC-MS m/z (ES⁺), 295.10 [M+H]⁺.

Synthesis of Compound 24

To a solution of compound 23 (444.1 mg, 1.5 mmol) and Et₃N (0.23 mL, 1.66 mmol) in CH₂Cl₂ (30 mL), mercapto acetic acid (0.23 mL, 3.32 mmol) in CH₂Cl₂ (5 mL) was added dropwise under an ice bath. Following complete addition, the solution was allowed to warm to room temperature and left to stir overnight. The solvent was removed in vacuo and the residue was purified by column chromatography (MeOH:CH₂Cl₂=60:1-30:1) to give the compound 24 as a yellow oil (1.72 g, 36.87%). LC-MS m/z (ES⁻), 385.10 (M−H)⁻.

Synthesis of Compound 25

Compound 24 (22.2 mg, 0.057 mmol), HOBt (9.3 mg, 0.069 mmol) and EDCI (16.5 mg, 0.086 mmol) were dissolved in 5.0 mL CH₂Cl₂. Subsequently, compound 21 (64.5 mg, 0.063 mmol) and DIPEA (20.3 µL, 0.104 mmol) were added to the mixture. The solution was allowed to warm to room temperature and left to react for 24 hours. The resulting solution was separated by prep-HPLC to give compound 25 as a white solid (25.3 mg, 29.7%). LC-MS m/z (ES⁺), 1479.80 (M+H)⁺.

Example I-4 Synthesis of Compound 31
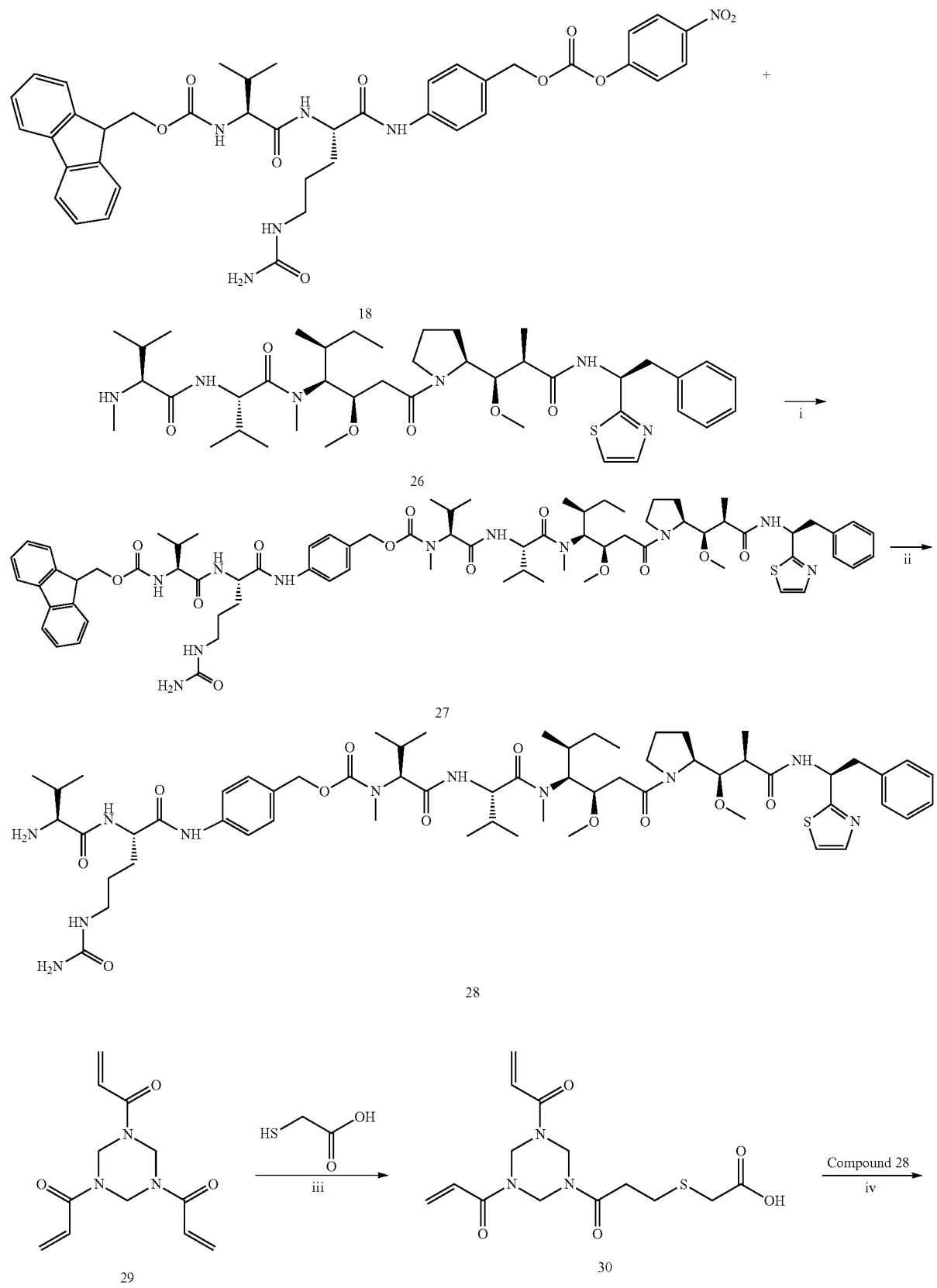

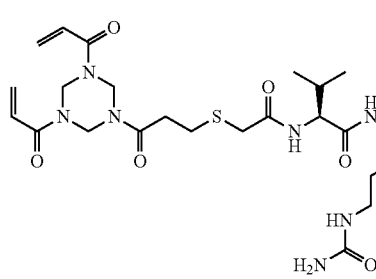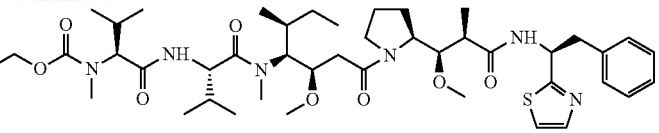

31 i) HOBt, DIPEA, Pyridine, DMF, R.T., 24 h ii) DEA, DMF, R.T., 2.5 h; iii) Et$_3$N, CH$_2$Cl$_2$, R.T., 12 h; iv) DIC, HOBt, DIPEA, DMF, R.T., 24 h.

Synthesis of Compound 27

To a solution of 18 (194.2 mg, 0.25 mmol) in dry DMF (15 mL) at 0° C. under nitrogen, HOBt (34.2 mg, 0.25 mmol) and compound 26 (200.3 mg, 0.28 mmol) was added. After stirring for 15 minutes, pyridine (3 mL) and DIPEA (53.1 μL, 0.32 mmol) were added and left to react for 30 minutes at 0° C. Then the reaction mixture was allowed to stir at room temperature for 3 hours. The mixture was replenished DIPEA (53.1 μL, 0.32 mmol) and reacted for another 24 hours. Upon completion of the reaction, the mixture was concentrated in vacuo. The crude product was purified by column chromatography to give the compound 27 (126.2 mg, 37.0%) as a white solid. LC-MS m/z (ES$^+$), 1398.75 (M+H)$^+$.

Synthesis of Compound 28

Diethylamine (4 mL) was added to a solution of compound 27 (126.2 mg, 0.09 mmol) in DMF (8 mL) at room temperature. After stirring for 2.5 hours, the solvent was removed under reduced pressure to give a crude product 28 (73.3 mg, 68.9%) which could be used without purification. LC-MS m/z (ES$^+$), 1176.68 (M+H)$^+$.

Synthesis of Compound 30

To a solution of compound 29 (1.87 g, 7.5 mmol) and Et$_3$N (104 μL, 0.75 mmol) in CH$_2$Cl$_2$ (40 mL), mercapto acetic acid (103.9 μL, 1.5 mmol) in CH$_2$Cl$_2$ (10 mL) was dropwise added at 0° C. Upon complete addition, the solution was allowed to warm to room temperature and left to stir overnight. The solvent was removed in vacuo and the residue was purified by column chromatography to give the compound 30 as a white solid (1.72 g, 36.87%). LC-MS m/z (ES$^-$), 342.11 (M–H)$^-$.

Synthesis of Compound 31

Compound 30 (22.2 mg 0.065 mmol), HOBt (8.8 mg 0.065 momol) and DIC (11 μL, 0.065 mmol) were added to DMF (8 mL) and cooled to 0° C. in an ice bath. Compound 28 (63.7 mg, 0.054 mmol) and DIPEA (12.4 μL, 0.054 mmol)) were added to the solution. The mixture was allowed to warm to room temperature and left to react for 24 hours. The residue was purified by column chromatography (MeOH:CH$_2$Cl$_2$=60:1-30:1) to yield compound 31 as a white solid (11.3 mg, 39.5%). LC-MS m/z (ES$^+$), 1499.78 (M+H)$^+$.

Example I-5 Synthesis of Compound 36

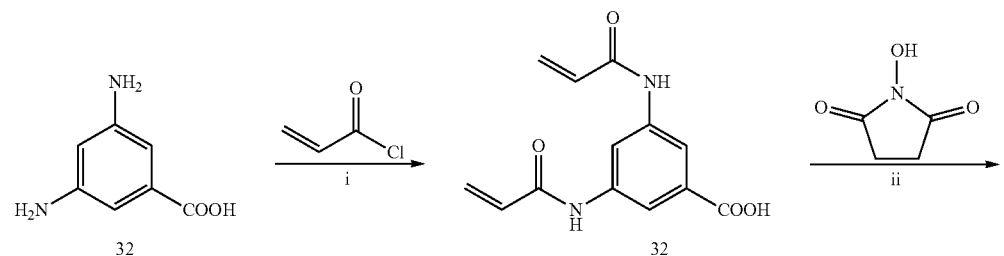

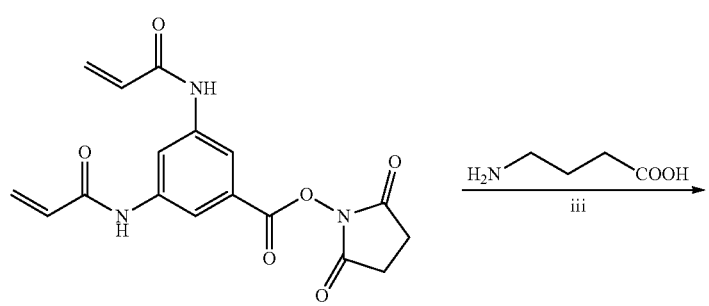

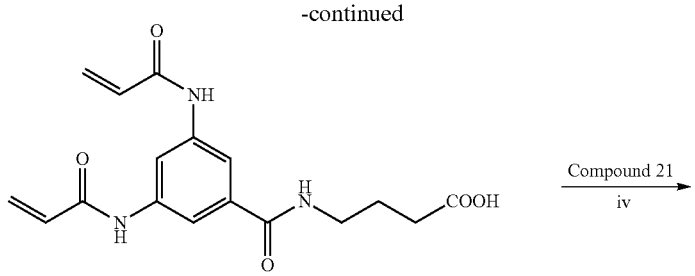

35

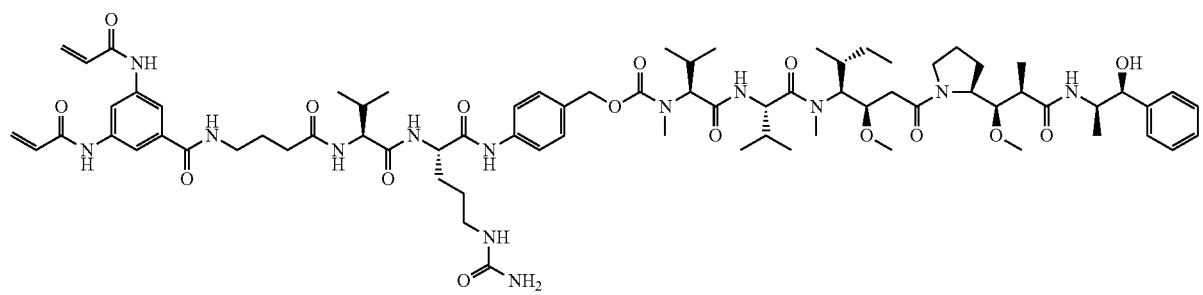

36 i) K$_2$CO$_3$, EtOAc/H$_2$O, R.T., 2 h ii) EDCI, DMF, R.T., 12 h; iii) DIPEA, DMF, R.T.,12 h; iv) EDCI, HOBt, DIPEA, DMF, R.T., 24 h.

Synthesis of Compound 33

2,4-Diaminobenzoic acid 32 (501.8 mg, 3.3 mmol) was dispersed in ethyl acetate (20 mL) and a solution of potassium carbonate (9.0 g, 66 mmol) in water (20 mL) was added. To the mixture, acryloyl chloride (1 mL, 13 mmol) was carefully added, resulting in the formation of a light brown precipitate. The reacting mixture was then allowed to reach room temperature, lead to the dissolution of the precipitate. After 2 hour, the reaction was complete. The organic layer was discarded and the aqueous layer was acidified with 5% hydrochloric acid, making a precipitate appear at pH<4. The precipitate was filtered, washed with petroleum ether and diluted with ethyl acetate. The organic layer was then dried over anhydrous magnesium sulfate, filtered, and removed in vacuo. The solid residue was suspended in water, filtered, and washed thoroughly with diethyl ether to give product 33 (670.2 mg, 78%) as a gray powder. LC-MS m/z (ES$^+$), 261.09 (M+H)$^+$.

Synthesis of Compound 34

Compound 33 (260.1 mg, 1.0 mmol) and EDCI (210.9 mg, 1.1 mmol), N-hydroxy succinimide (126.6 mg, 1.1 mmol) was dissolved in DMF (14 mL). The solution was stirred overnight at room temperature. Upon completion of the reaction, the solvent was removed under reduced pressure. The solid residue was purified by column chromatography with CH$_2$Cl$_2$/MeOH (10:1) as eluent to give the product 34 as a light brown solid (273 mg, 76.4%). LC-MS m/z (ES$^+$), 358.11 (M+H)$^+$.

Synthesis of Compound 35

To a solution of 4-aminobutyric acid (82.4 mg, 0.8 mmol) and DIPEA (489 µL, 2.8 mmol) in DMF (10 mL), a solution of compound 34 (260.7 mg, 0.73 mmol) in DMF (10 mL) was added at 0° C. in an ice bath. The mixture was stirred for 10 minutes at 0° C. and then stirred at room temperature overnight. The solvent was removed in vacuo when the reaction was completed. The solid residue was purified by column chromatography (CH$_2$Cl$_2$:MeOH=10:1, v/v) to yield the compound 35 (192.3 mg, 76.2%). LC-MS m/z (ES$^+$), 346.14 (M+H)$^+$.

Synthesis of Compound 36

HOBt (14.9 mg, 0.11 mmol), EDCI (21.1 mg, 0.11 mmol) and DIPEA (19.2 µL, 0.11 mmol) was added to a stirred solution of 35 (34.5 mg, 0.1 mmol) in dry DMF (10 ml) at 0° C. After 15 minutes, compound 21 (112.3 mg, 0.1 mmol) was added. The reaction mixture was allowed to warm to room temperature and stirred for 24 hours. The mixture was added water (15 mL) and extracted with ethyl acetate (20 mL×3). The combined organic layers were dried over anhydrous magnesium sulfate, filtered, and removed in vacuo. The crude product was purified by column chromatography (CH$_2$Cl$_2$:MeOH=10:1, v/v) to afford compound 36 as a white solid (56.5 mg, 39%). LC-MS m/z (ES$^+$), 1450.84 (M+H)$^+$.

Example I-6 Synthesis of Compound 43

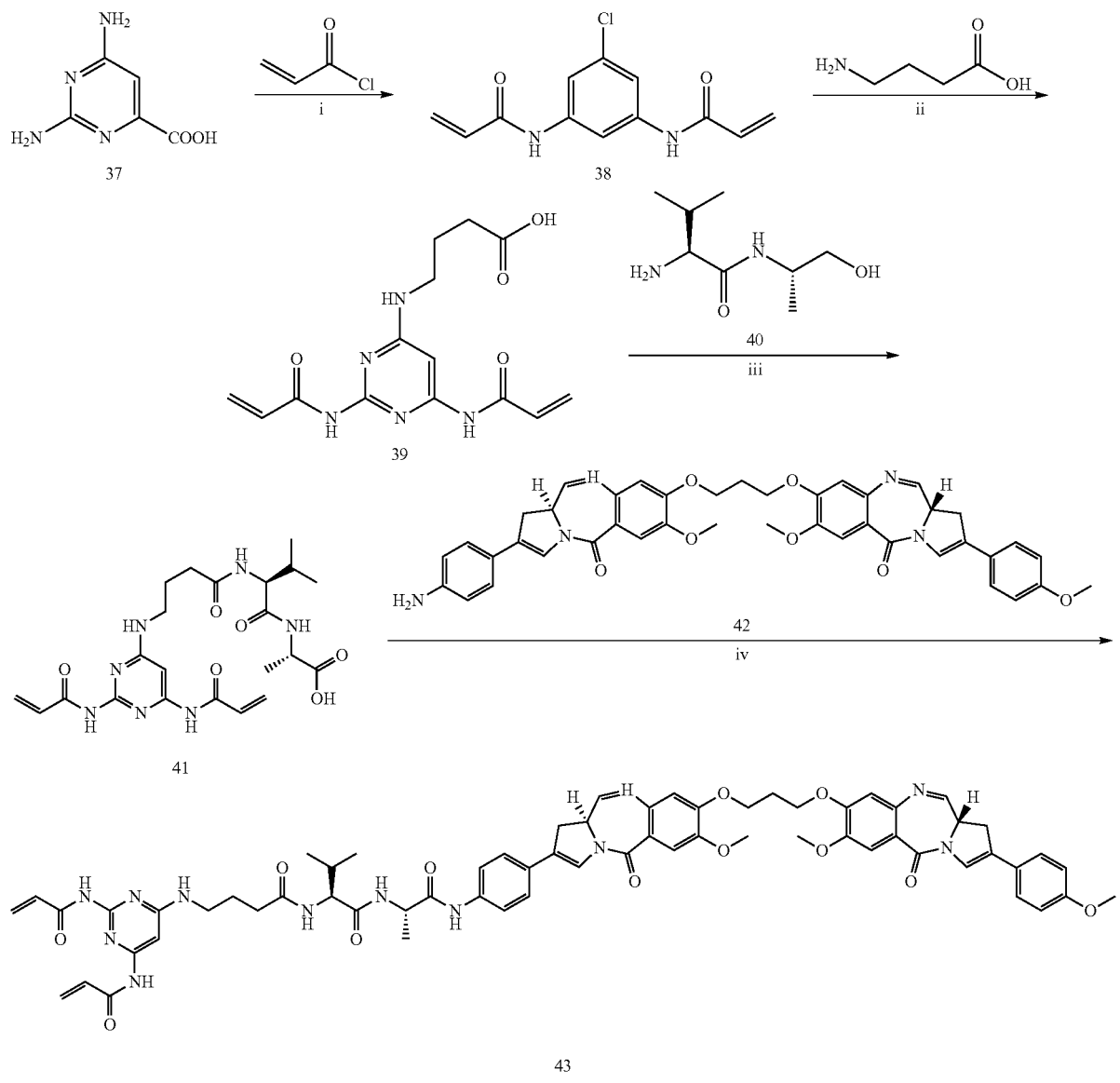

i) DMAP, CH$_2$Cl$_2$, R.T., 1 h; ii) NAOH, EtOH/H$_2$O, 80° C., 2 h; iii) EDCI, HOBt, DIPEA, DMF, R.T., 18 h; (iv) EEDQ, CH$_2$Cl$_2$, MeOH, R.T., 18 h.

Synthesis of Compound 38

Into a 100 mL round-bottom flask was placed a solution of compound 37 (1.05 g, 6.9 mmol) and DMAP (1.94 g, 15.9 mmol) in CH$_2$Cl$_2$ (20 mL), acryloyl chloride (1.38 g, 15.2 mmol) was added dropwise with stirring at 0° C. The reaction was stirred for 1 hour at room temperature. The reaction was quenched by the addition of water (50 mL) and extracted with CH$_2$Cl$_2$ (20 mL×3). The organic phase was combined, washed with saturated sodium bicarbonate solution (30 mL), and brine (30 mL), dried over anhydrous sodium sulfate, and filtered. The filtrate was concentrated under reduced pressure to afford compound 38 (1.51 g, 85.8%) as a light yellow semi-solid. LC-MS m/z (ES$^+$), 253.04 (M+H)$^+$.

Synthesis of Compound 39

Compound 38 (1.56 g, 5.94 mmol) and 4-aminobutanoic acid (673.0 mg, 6.53 mmol) were dissolved in EtOH (15 ml) along with sodium hydroxide (713.3 mg, 17.82 mmol) in water (15 mL). The reaction mixture was stirred for 2 hours at 80° C. After cooled to room temperature, the solvent was concentrated under reduced pressure. The mixture was acidify to ph<7 with hydrochloric acid (0.5 N). The solid was collected by filtration, washed with water (10 mL×2) and dried to afford compound 39 (490.2 mg, 25.8%) as an off-white solid. LC-MS m/z (ES$^+$), 320.03 (M+H)$^+$.

Synthesis of Compound 41

Compound 39 (230.1 mg, 0.72 mmol), HOBt (116.7 mg, 0.86 mmol), EDCI (151.8 mg, 0.79 mmol) and DIPEA (279.2 mg, 2.2 mmol) were added to DMF (20 mL) and stirred at 0° C. in an ice bath. After 1 hour, compound 40

(149.1 mg, 0.79 mmol) was added to the solution. The mixture was allowed to warm to room temperature and left to react for 18 hours. The reaction mixture was diluted with brine (50 mL), extracted with ethyl acetate (20 mL×3). The organic layers were combined and dried with anhydrous sulfate sodium, filtered and concentrated. The residue was purified by column chromatography (MeOH:CH$_2$C$_2$=200/1-10/1, v/v) to yield compound 41 as a yellow solid (97.3 mg, 27.6%). LC-MS m/z (ES$^+$), 490.23 (M+H)$^+$.

Synthesis of Compound 43

A solution of compound 41 (90.1 mg, 0.18 mmol), EEDQ (54.6 mg, 0.22 mmol) in anhydrous CH$_2$Cl$_2$ (7 ml) and anhydrous MeOH (0.07 mL) was stirred for 1 hour at room temperature. Subsequently, compound 42 (133.5 mg, 0.184 mmol) was added. The reaction mixture was stirred for additional 18 hours. The reaction mixture was concentrated in vacuo, and purified by prep-HPLC to afford compound 43 (12.3 mg, 5.6%) as a white solid. LC-MS m/z (ES$^+$), 1197.51 (M+H)$^+$.

Example I-7 Synthesis of Compound 49

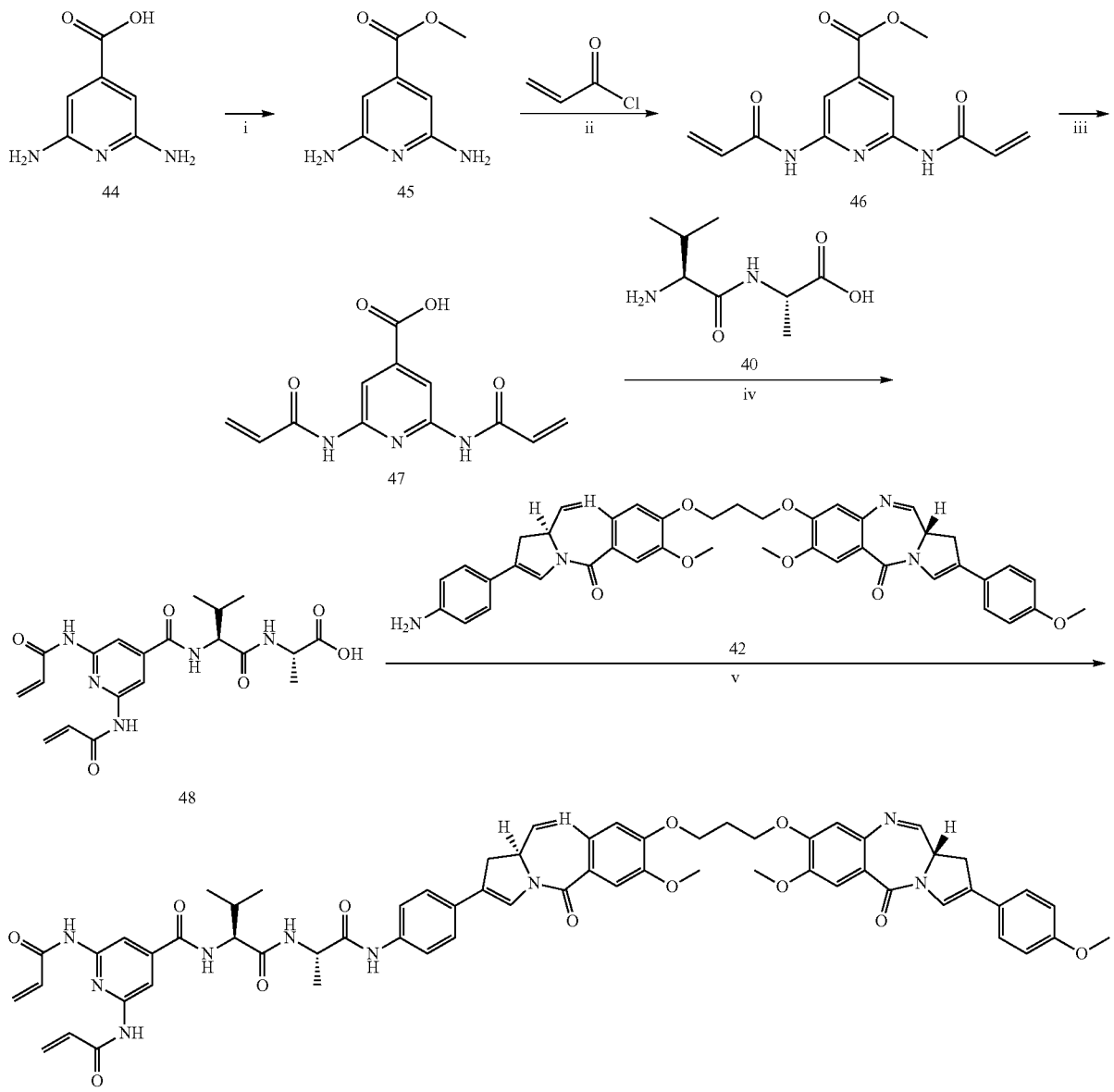

i) HCl(g), MeOH, 0° C., 2 h; ii) pyridine, 100° C., 2 h; iii) NaOH, THF/H$_2$O, R.T., 4 h; iv) EDCI, HOBt, DIPEA, DMF, R.T., 18 h; v) EEDQ, CH$_2$Cl$_2$/MeOH, R.T., 18 h.

Synthesis of Compound 45

To a solution of compound 44 (1.13 g, 6.53 mmol) in methanol (30 mL), hydrochloric acid (gas) was introduced in with stirring at 0° C. The reaction was stirred for 2 hours at 0° C. The mixture was concentrated and the residue was dissolved in water (50 mL). The mixture was adjust to 8 with saturated sodium bicarbonate, extracted with ethyl acetate (20 mL×3). The organic layer was combined and dried with anhydrous sodium sulfate, filtered. The filtrate was concentrated to afford compound 45 (710.1 mg, 65.1%) as a yellow solid. LC-MS m/z (ES+), 168.07 (M+H)+.

Synthesis of Compound 46

Acryloyl chloride (947.1 mg, 10.47 mmol) was added dropwise to a solution of compound 45 (700.5 mg, 4.19 mmol) in pyridine (20 mL) with stirring at 0° C. in an ice bath. The reaction mixture was stirred for 2 hours at 100° C. After cooled to room temperature, the reaction mixture was concentrated under reduced pressure. The residue was purified by column chromatography (MeOH:CH$_2$Cl$_2$=200/1-10/1, v/v) to afford compound 46 (520.4 mg, 45.2%) as a yellow solid. LC-MS m/z (ES+), 276.09 (M+H)+.

Synthesis of Compound 47

A mixture of compound 46 (510.2 mg, 1.85 mmol), sodium hydroxide (370.6 mg, 9.26 mmol), THF (10 mL) and water (10 mL) was stirred for 4 hours at room temperature. Upon complete reaction, the mixture was concentrated and adjusted PH to 7 with hydrochloric acid (IN). The compound 47 (360.2 mg, 74.1%) was collected by filtration as an off-white solid. LC-MS m/z (ES+), 262.07 (M+H)+.

Synthesis of Compound 48

Compound 47 (120.5 mg, 0.5 mmol), HOBt (4.7 mg, 0.6 mmol), EDCI (96.8 mg, 0.5 mmol) and DIPEA (178.1 mg, 1.4 mmol) were added to DMF (10 mL) and stirred at 0° C. in an ice bath After 1 hour, compound 40 (95.1 mg, 0.5 mmol) was added to the solution. The mixture was allowed to warm to room temperature and left to react for 18 hours. The reaction mixture was diluted with brine (20 mL), extracted with ethyl acetate (10 mL×3). The organic layers were combined and dried with anhydrous sulfate sodium, filtered and concentrated. The residue was purified by column chromatography (MeOH:CH$_2$Cl$_2$=100/1-20/1, v/v) to yield compound 41 as an off white solid (71 mg, 35.8%). LC-MS m/z (ES+), 432.07 (M+H)+.

Synthesis of Compound 49

Compound 48 (60.2 mg, 0.14 mmol), EEDQ (41.3 mg, 0.17 mmol) was dissolved in anhydrous CH$_2$Cl$_2$ (6 ml) and anhydrous MeOH (0.06 mL) and left to stir for 1 hour at room temperature. Compound 42 (100.9 mg, 0.14 mmol) was added to the solution. The reaction mixture was stirred for additional 18 hours. The reaction mixture was concentrated under reduced pressure, and purified by prep-HPLC to afford compound 49 (12.4 mg, 7.61%) as a white solid. LC-MS m/z (ES+), 1139.45 (M+H)+.

Example I-8 Synthesis of Compound 55

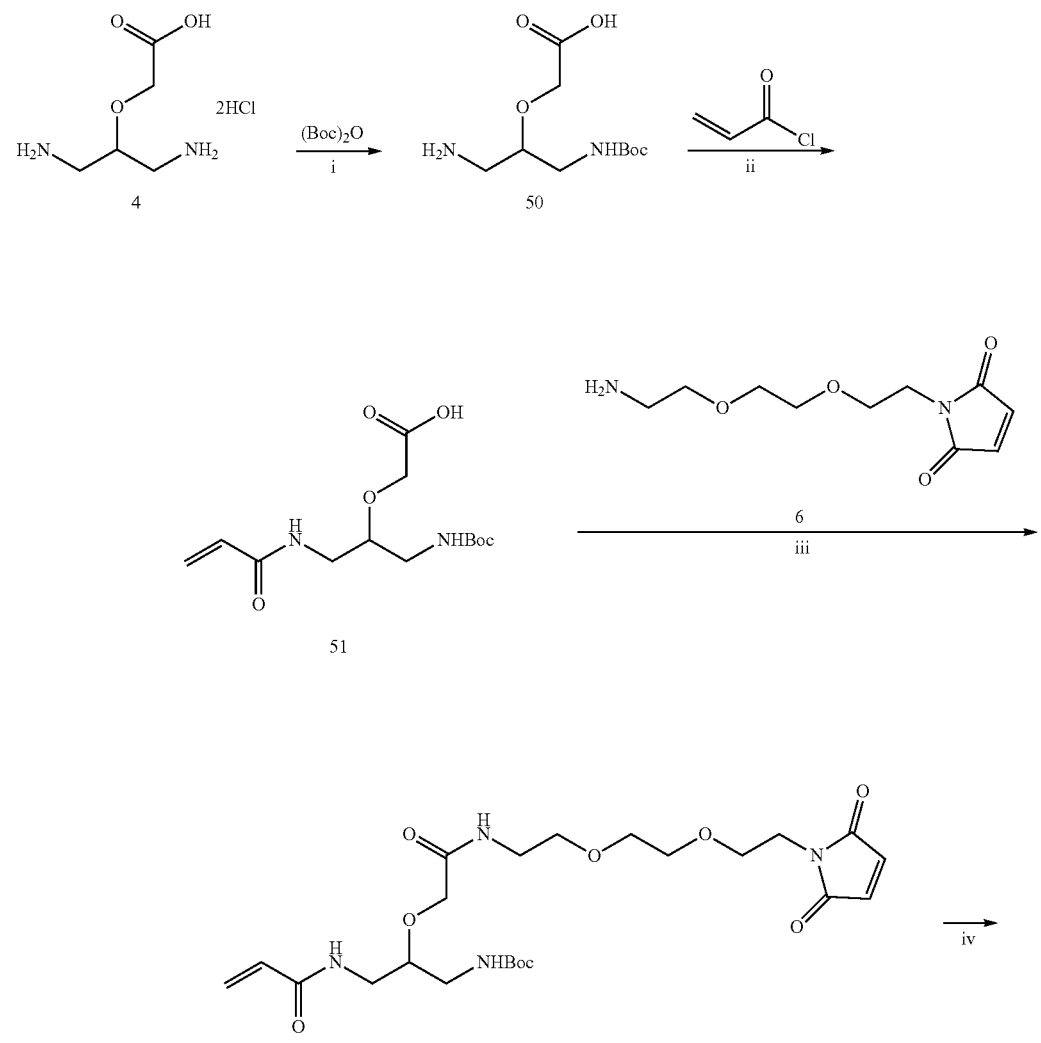

-continued

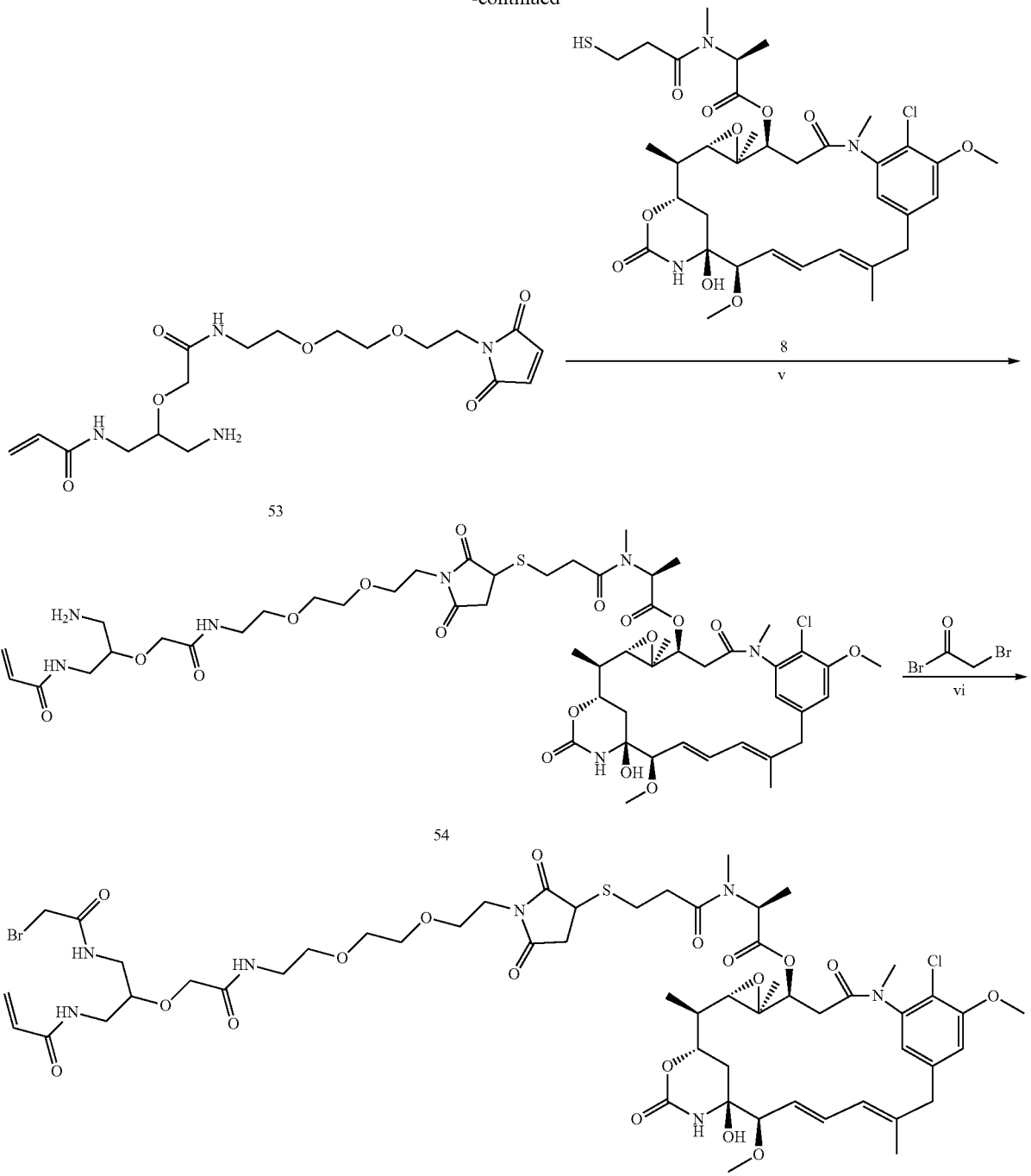

i) Et₃N, MeOH R.T., 3 h; ii) Na₂CO₃, THF/H₂O, R.T., 3 h; iii) HOBt, DIC, DIPEA, DMF, R.T., 12 h; iv) TFA, CH₂Cl₂, R.T., 3 h; v) Et₃N, CH₂Cl₂, R.T., 2 h; vi)

Synthesis of Compound 50

Et₃N (332.7 Id, 2.4 mmol) was added to a solution of compound 4 (440.0 mg, 2 mmol) in MeOH (10 mL) at 45° C. Then a solution of (Boc)₂O (436.2 mg, 2 mmol) in MeOH (10 mL) was added. The resulting mixture was vigorously stirred at 45° C. for 30 minutes, followed by stirring at room temperature for 2 hours. After solvent removed, the residue was washed with hydrochloric acid (5%, 10 mL), saturated sodium chloride solution (15 mL), and extracted with ethyl acetate (10 mL×3). The organic layer was dried over anhydrous magnesium sulfate, filtered, and removed in vacuo. The solid residue was recrystallized by petroleum ether/ethyl acetate (10 mL, v:v=2:1,) to give compound 50 (375.4 mg, 75.6%) as a white powder. LC-MS m/z (ES⁺), 249.15 (M+H)⁺.

Synthesis of Compound 51

Acryloyl chloride (121 µL, 1.5 mmol) was added to a solution of compound 50 (248.0 mg, 1.0 mmol) in saturated sodium bicarbonate solution/THF (v/v=1:1, 20 mL) at 0° C. The resulting mixture was vigorously stirred at 0° C. for 10 minutes. The mixture was allowed to raise to room temperature and reacted for 3 hours. The mixture was acidified with hydrochloric acid to adjust pH<4. The mixture was extracted by ethyl acetate (20 mL×3). The organic layers were combined and washed with saturated sodium chloride solution (30 mL), dried over anhydrous magnesium sulfate, filtered and the solvent was removed. The solid residue was purified by prep-HPLC to give product 51 (176.1 mg, 58.3%) as a gray oil. LC-MS m/z (ES$^+$), 303.16 (M+H)$^+$.

Synthesis of Compound 52

Compound 51 (30.2 mg, 0.1 mmol), HOBt (14.7 mg, 0.11 mmol) and DIC (13.9 mg, 0.11 mmol) were dissolved in dry DMF (6 mL) and cooled to 0° C. in an ice bath. After 15 minutes, compound 6 (20.5 mg, 0.09 mmol) and DIPEA (19.2 µL, 0.11 mmol) were added to the mixture. The solution was allowed to warm to room temperature and stirred overnight. The mixture was diluted with water (10 mL) and extracted with ethyl acetate (20 mL×3). The combined organic layers were dried over anhydrous magnesium sulfate and the solvent was removed in vacuo. The crude product was purified by column chromatography (CH$_2$Cl$_2$:MeOH=20:1, v/v) to yield compound 52 as a white solid (28.2 mg, 60.7%). LC-MS m/z (ES$^+$), 513.26 (M+H)$^+$.

Synthesis of Compound 53

A solution of Compound 52 (28.2 mg, 0.06 mmol) trifluoroacetic acid (1.0 mL) in CH$_2$Cl$_2$ (5 mL) was stirred for 3 hours at room temperature. The solvent was removed under reduced pressure to yield compound 53 (20.4 mg, 88.2%) as a gray solid which could be used in next step without further purification. LC-MS m/z (ES$^+$), 413.21 (M+H)$^+$.

Synthesis of Compound 54

Compound 53 (41.2 mg, 0.1 mmol) was dissolved in 10 mL DMF and cooled to 0° C. in an ice bath. Et$_3$N (6.9 µL, 0.05 mmol) and the compound 8 (73.7 mg, 0.1 mmol) were added dropwise to the solution and left to stir for 30 minutes. The solution was allowed to warm to room temperature and stirred for another 5 hours. The mixture was concentrated under reduced pressure, and the residue was purified by pre-HPLC to give compound 54 (73 mg, 63.6%) as a white powder. LC-MS m/z (ES$^+$), 1148.47 (M+H)$^+$.

Synthesis of Compound 55

Bromoacetyl bromide (150.0 mg, 0.75 mmol) was added to a solution of compound 54 (573.7 mg, 0.5 mmol) in DMF (10 mL) at 0° C. The resulting mixture was stirred at 0° C. for 10 minutes and then allowed to stir at room temperature for another 3 hours. The mixture was added water (20 mL) and extracted by ethyl acetate (20 mL×3). The combined organic layers were concentrated, and the residue was purified by pre-HPLC to give compound 55 (421 mg, 66.4%) as a yellow powder. LC-MS m/z (ES$^+$), 1270.38 (M+H)$^+$.

Example I-9 Synthesis of Compound 59

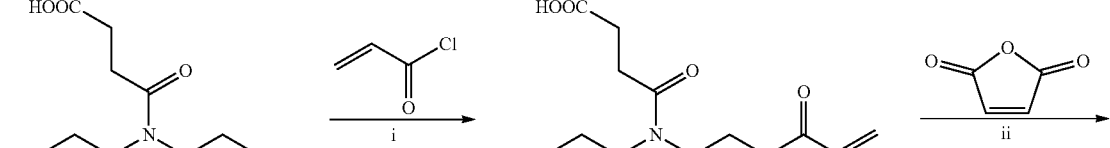

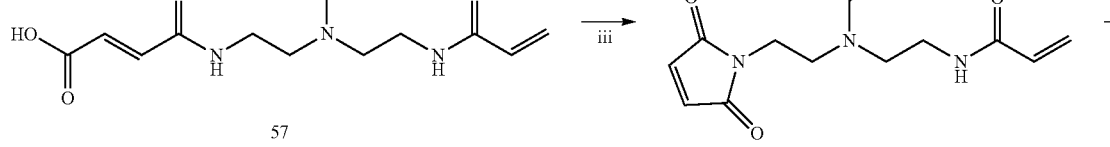

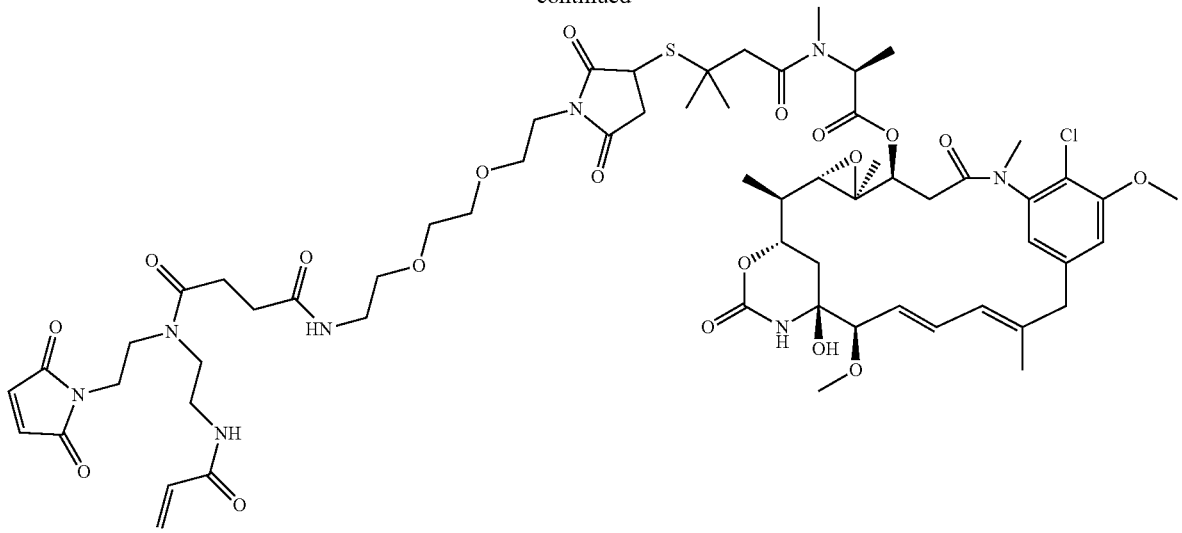

59 i) K$_2$CO$_3$, H$_2$O/EtOAc, R.T., 5 h; ii) CHCl$_3$, Reflux, 12 h; iii) Ac$_2$O, NaAc, 100° C., 2 h; iv) HOBt, DIC, DIPEA, DMF, R.T., 24 h.

Synthesis of Compound 56

To a mixture of potassium carbonate (51.2 mg, 0.37 mmol) in water (5 mL) and compound 15 (50.0 mg, 0.25 mmol) in ethyl acetate (10 mL), a solution of acryloyl chloride (16 µL, 0.2 mmol) in ethyl acetate (8 mL) was dropwise added slowly at 0° C. Upon complete addition, the resulting mixture was stirred at 0° C. in an ice bath for additional 10 minutes. Then the mixture was allowed to raise to room temperature and reacted for 5 hours. The mixture was acidified with hydrochloric acid to adjust pH<5. The mixture was extracted with ethyl acetate (15 mL×3). The organic combined layers were washed with saturated sodium chloride solution (15 mL), dried over anhydrous magnesium sulfate, filtered and removed the solvent. The solid residue was purified by column chromatography (MeOH:CH$_2$Cl$_2$=8:1) to give product 56 (26.2 mg, 40.1%) as a gray oil. LC-MS m/z (ES$^+$), 258.14 (M+H)$^+$.

Synthesis of Compound 57

Compound 56 (26.0 mg, 0.10 mmol) was stirred in CHCl$_3$ (10 mL), maleic anhydride (28.1 mg, 0.11 mmol) was added to the mixture. The reaction was heated to reflux for 12 hours. After cooled to room temperature, solid product precipitated was filtered and washed with CHCl$_3$ (30 mL×3) to afford the compound 57 (20.1 mg, 59.1%) as a white solid. LC-MS m/z (ES$^+$), 356.14 (M+H)$^+$.

Synthesis of Compound 58

A solution compound 57 (20.1 mg 0.054 mmol) and sodium acetate (6.3 mg, 0.047 mmol) in acetic anhydride (10 mL) was heated to 100° C. for 2 hours. Once the reaction was complete, the reaction solution was slowly poured into crushed ice with stirring, and iced water was added. Solid was precipitated out after 1 hour stirring. The solid residue was filtered and washed with iced water (15 mL×3) to give the compound 58 (9.1 mg, 46.1%) as a white solid. LC-MS m/z (ES$^+$), 338.13 (M+H)$^+$.

Synthesis of Compound 59

Compound 58 (8.1 mg 0.02 mmol), HOBt (3.25 mg, 0.02 mmol) and DIC (3.7 µL, 0.02 mmol) were dissolved in 5 mL DMF and cooled to 0° C. in an ice bath. Subsequently, compound 11 (20.1 mg, 0.02 mmol) and DIPEA (4.1 µL, 0.02 mmol) were added to the mixture. The solution was allowed to warm to room temperature and left to react for 24 hours. The resulting mixture was concentrated and purified by prep-HPLC to yield compound 59 (9.3 mg, 34.9%) as a white solid. LC-MS m/z (ES$^+$), 1313.53 (M+H)$^+$.

Example I-10 Synthesis of Compound 64

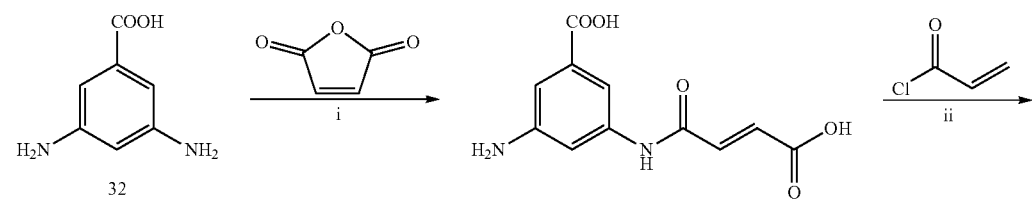

60

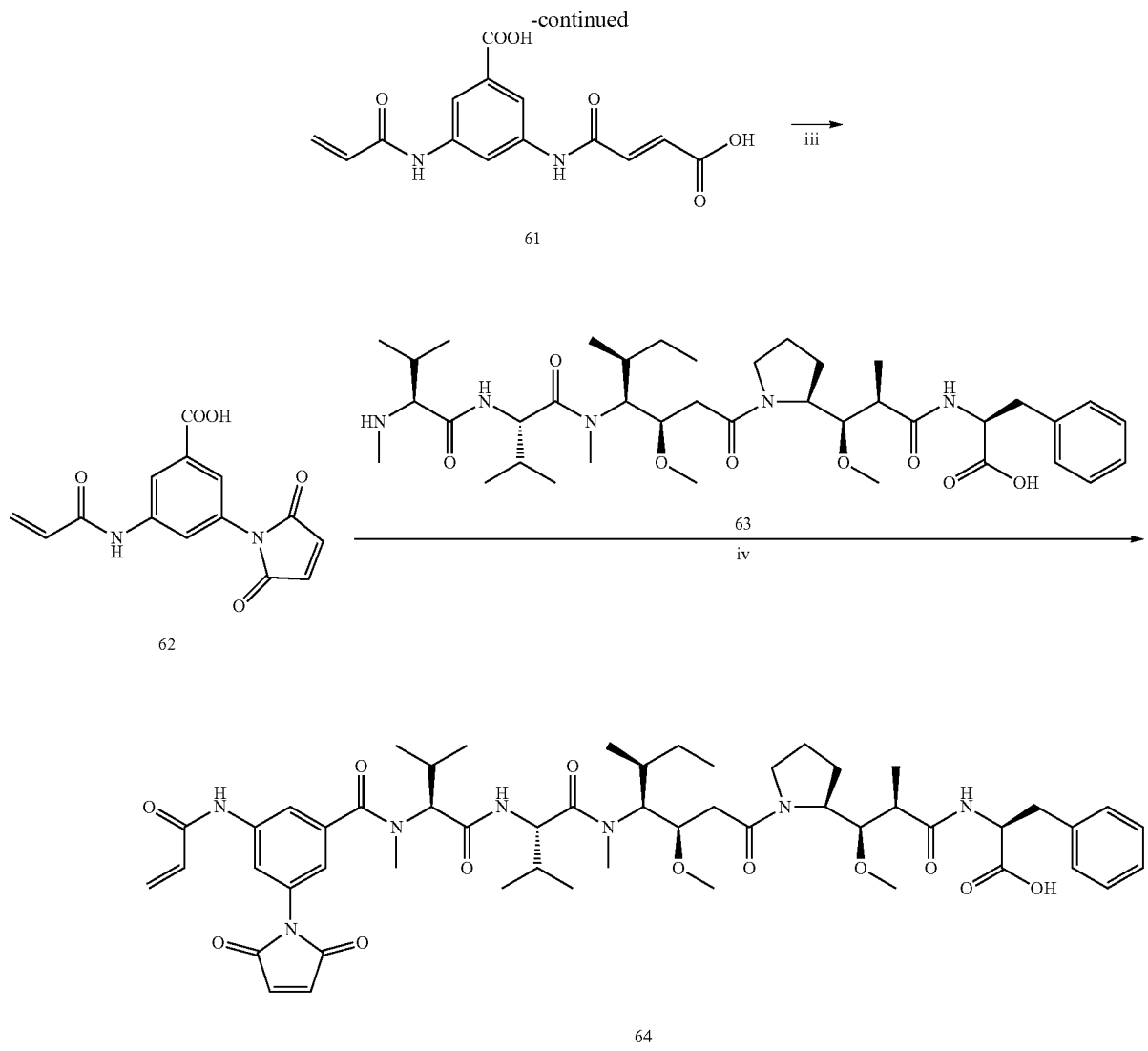

i) DMF, 80° C., 6 h; ii) K$_2$CO$_3$, EtOAc/H$_2$O, R.T., 5 h; iii) Ac$_2$O, NaAc, 90° C., 3 h; iv) HOBt, DIC, DIPEA, DMF, R.T., 24 h.

Synthesis of Compound 60

To a solution of compound 32 (140.0 mg, 0.9 mmol) in DMF (6 mL), maleic anhydride (89.8 mg, 0.9 mmol) was added dropwise. The mixture was stirred at 60° C. for 6 hours and then concentrated to oil under reduced pressure. The compound 60 (white solid, 209.1 mg, 90.7%) was obtained by recrystallization from ethyl acetate (5 ml). LC-MS m/z (ES$^+$), (M+H)$^+$251.06.

Synthesis of Compound 61

To a mixture of potassium carbonate (201.3 mg, 1.4 mmol) in water (15 mL) and compound 60 (209.1 mg, 0.9 mmol) in ethyl acetate (20 mL), a solution of acryloyl chloride (90 µL, 1.1 mmol) in ethyl acetate (10 mL) was added dropwise at 0° C. Upon complete addition, the mixture was allowed to warm to room temperature and reacted for 5 hours. The mixture was acidified with hydrochloric acid to adjust pH<5. The mixture was extracted with ethyl acetate (20 mL×2). The organic layers were combined and washed with saturated sodium chloride solution (20 mL), dried over anhydrous magnesium sulfate, and filtered. The solvent was removed under in vacuo to give compound 61 (201.0 mg, 82.7%) as a gray solid which could be used in next step without further purification. LC-MS m/z (ES$^+$), (M+H)$^+$ 304.07.

Synthesis of Compound 62

To a solution of crude compound 61 (201.0 mg, 0.7 mmol) in acetic anhydride (30 mL), sodium acetate (60.5 mg, 0.7 mmol) was added. The mixture was stirred at 90° C. for 3 hours. The reaction mixture was poured into ice water and stirred for 30 min and extracted with ethyl acetate (20 mL×3). The combined organic layers were concentrated and purified by prep-HPLC to give compound 62 (92.2 mg, 48.6%) as a white solid. LC-MS m/z (ES$^+$), (M+H)$^+$ 287.06.

Synthesis of Compound 64

The compound 62 (57.0 mg, 0.2 mmol), HOBt (27.2 mg, 0.2 mmol), DIC (29.3 µL, 0.2 mmol) and DIPEA (0.2 mmol, 33.1 µL) were added to DMF (6 mL). After 30 min, the compound 63 (109.8 mg, 0.15 mmol) and was added at 0° C. The mixture was allowed to stir at room temperature for 24 hours. The solution was concentrated and purified by prep-HPLC to give compound 64 (94.8 mg, 47.6%) as a white solid. LC-MS m/z (ES$^+$), 1000.53 (M+H)$^+$.

Example I-11 Synthesis of Compound 69

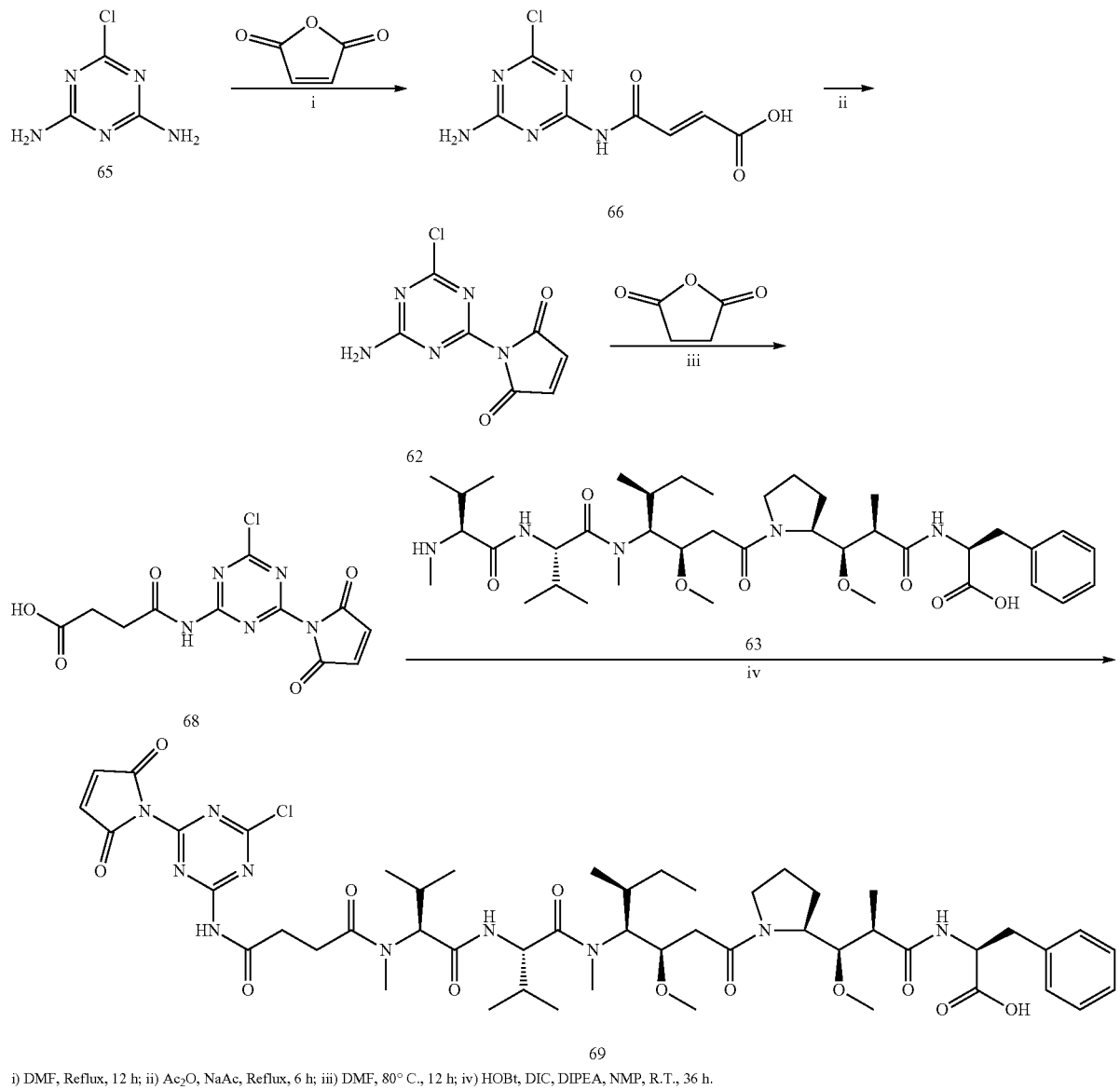

i) DMF, Reflux, 12 h; ii) Ac₂O, NaAc, Reflux, 6 h; iii) DMF, 80° C., 12 h; iv) HOBt, DIC, DIPEA, NMP, R.T., 36 h.

Synthesis of Compound 66

To a mixture of compound 65 (145.0 mg, 1.0 mmol) in DMF (6 mL), maleic anhydride (89.8 mg, 0.9 mmol) was dropwise added slowly. The mixture was heated to reflux for 12 hours. After cooled to room temperature, solid product precipitated was filtered and washed with $CH_2Cl_2$ (20 mL×3) to afford the compound 66 (110.2 mg, 45.1%) as a white solid. LC-MS m/z ($ES^+$), 244.02 $(M+H)^+$.

Synthesis of Compound 67

A mixture of compound 66 (110.2 mg, 0.5 mmol) and sodium acetate (14.2 mg, 0.2 mmol) in acetic anhydride (10 mL) was heated to reflux for 6 hours. Once the reaction was complete, the reaction mixture was slowly poured into crushed ice with stirring, and iced water was added. Solid residue was precipitated out after 1 hour stirring. The solid residue was filtered and washed with iced water (10 mL×3) to give the compound 67 (87.3 mg, 85.7%) as a white solid. LC-MS m/z ($ES^+$), 226.01 $(M+H)^+$.

Synthesis of Compound 68

Succinic anhydride (38.8 mg, 0.4 mmol) was added to a mixture of compound 67 (87.3 mg, 0.4 mmol) in DMF (6 mL). The mixture was stirred at 80° C. overnight and then concentrated to oil under reduced pressure. The crude product was purified by prep-HPLC to give compound 68 (45.0 mg, 35.7%) as white solid. LC-MS m/z ($ES^+$), 326.02 $(M+H)^+$.

Synthesis of Compound 69

Compound 68 (45.0 mg, 0.14 mmol), HOBt (19.0 mg, 0.14 mmol), DIC (20.5 µL, 0.14 mmol) and DIPEA (23.2 µL, 0.14 mmol) were added to DMF (10 mL) and stirred at 0° C. in an ice bath for 1 hour. Compound 63 (76.9 mg, 0.11 mmol) was added to the solution. The mixture was allowed to warm to room temperature and left to react for 36 hours.

The reaction mixture was purified by prep-HPLC to yield compound 69 (64.3 mg, 44.3%) as a white solid. LC-MS m/z (ES+), 1039.49 (M+H)+.

Example I-12 Synthesis of Compound 74

Synthesis of Compound 72
Acryloyl chloride (947.2 mg, 10.47 mmol) was added dropwise to a solution of compound 71 (450.5 mg, 1.95 mmol) and TEA (590.8 mg, 5.85 mmol) in CH$_2$Cl$_2$ (20 ml) with stirring at 0° C. in an ice bath. The reaction mixture was stirred for 18 hours at room temperature. The reaction was

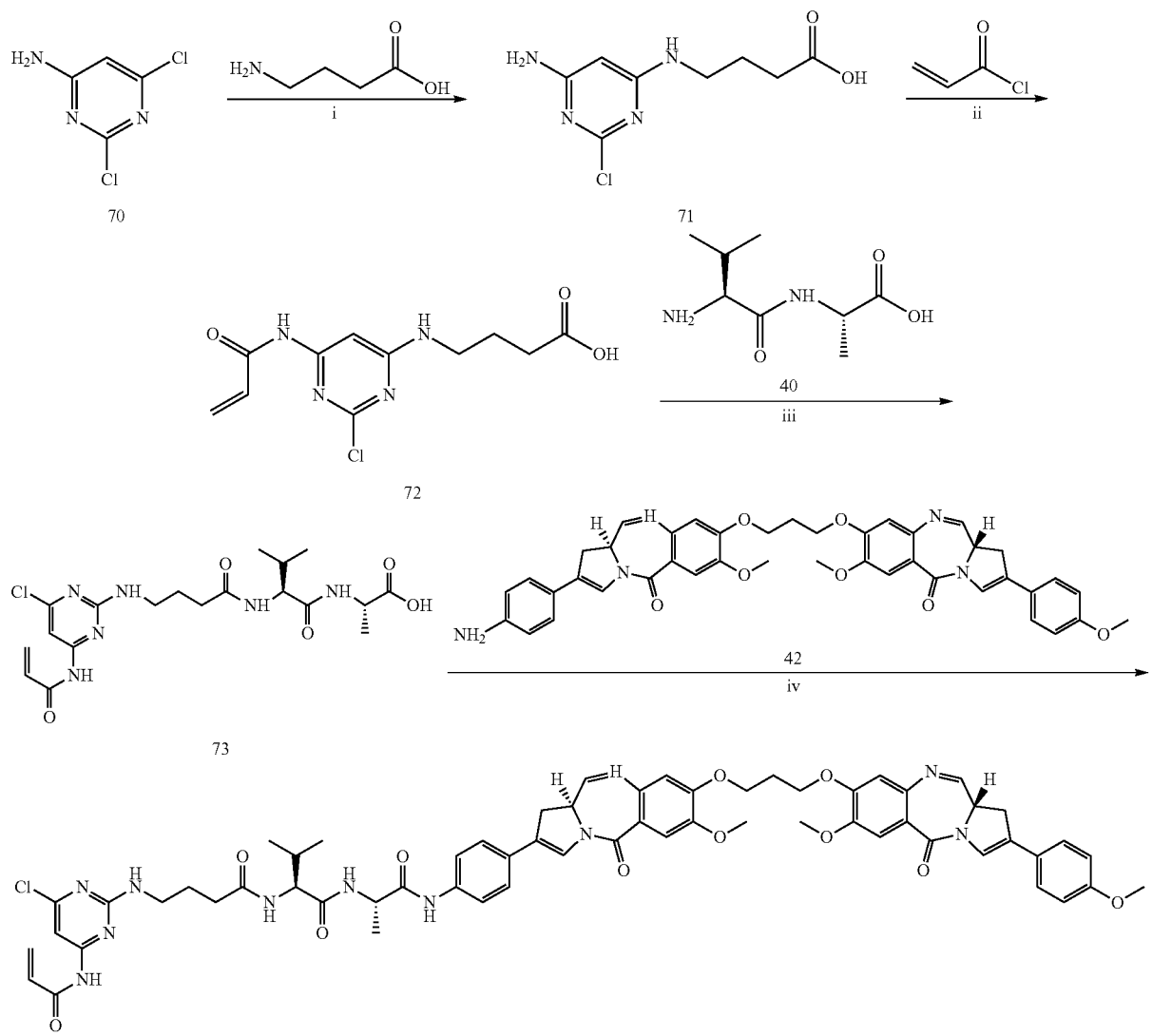

i) Et$_3$N, n-Butanol, 90° C., 18 h; ii) Et$_3$N, CH$_2$Cl$_2$, R.T., 18 h; iii) EDCI, HOBt, DIPEA, DMF, R.T., 18 h, (iv) EEDQ, CH$_2$Cl$_2$, MeOH, R.T., 18 h.

Synthesis of Compound 71
Compound 69 (1.0 g, 6.10 mmol) and 4-aminobutanoic acid (691.9 mg, 6.71 mmol) and triethylamine (3.09 g, 30.5 mmol) was dissolved in n-Butanol (30 mL). The reaction mixture was stirred for 18 hours at 900. After cooled to room temperature, the solvent was concentrated under reduced pressure. The residue was diluted with water (100 mL) and extracted with ethyl acetate (30 mL×3). The organic phase was combined and dried over anhydrous sulfate sodium, filtered and concentrated. The residue was purified by column chromatography (MeOH:CH$_2$Cl$_2$=200/1-10/1, v/v) to yield compound 71 as a yellow solid (482.3 mg, 34.3%). LC-MS m/z (ES+), 231.06 (M+H)+.

quenched by the addition of water (50 mL) and extracted with CH$_2$Cl$_2$ (20 mL×3). The organic layer was combined, washed with brine (30 mL), dried over anhydrous sulfate sodium, filtered and concentrated to afford compound 72 (255.4 mg, 46%) as a yellow solid. LC-MS m/z (ES+), 285.07 (M+H)+.

Synthesis of Compound 73
Compound 3 (155.7 mg, 0.547 mmol), HOBt (88.7 mg, 0.656 mmol), EDCI (115.4 mg, 0.602 mmol) and DIPEA (212.1 mg, 1.64 mmol) were added to DMF (10 mL) and stirred at 0° C. in an ice bath for 1 hour. Compound 40 (113.3 mg, 0.602 mmol) was added to the solution. The mixture was allowed to warm to room temperature and left to react for 18 hours. The reaction mixture was diluted with brine (30 mL), extracted with CH$_2$Cl$_2$ (10 mL×3). The organic layer was combined and dried over anhydrous sulfate sodium, filtered and concentrated. The residue was purified by column chromatography (MeOH:CH$_2$Cl$_2$=200/1-10/1, v/v) to yield compound 73 as a yellow solid (90.2 mg, 36.2%). LC-MS m/z (ES$^+$), 455.17 (M+H)$^+$.

Synthesis of Compound 74

A solution of compound 73 (85.4 mg, 0.19 mmol), EEDQ (55.4 mg, 0.23 mmol) in anhydrous CH$_2$Cl$_2$ (7 ml) and anhydrous MeOH (0.07 mL) was stirred for 1 hour at room temperature. Subsequently, compound 42 (135.7 mg, 0.19 mmol) was added. The reaction mixture was stirred for additional 18 hours. The reaction mixture was concentrated in vacuo, and purified by prep-HPLC to afford compound 74 (19.1 mg, 6.7%) as a white solid. LC-MS m/z (ES$^+$), 1162.45 (M+H)$^+$.

TABLE 1

| | Other linker-active agent conjugates | |
|---|---|---|
| ID | Structure of linker-active agent conjugates | MS (M + H)$^+$ |
| 75 | | 1446.80 |
| 76 | | 1041.62 |
| 77 | | 1234.58 |
| 78 | | 1444.89 |
| 79 | | 1419.85 |

TABLE 1-continued

Other linker-active agent conjugates

| ID | Structure of linker-active agent conjugates | MS (M + H)+ |
|---|---|---|
| 80 | | 1237.25 |

Example II Preparation of Antibody Drug Conjugates

General Conjugation Procedure

DTPA (1 mM) and 3.0-5.0 equiv. of TCEP (10 mM) were added to antibody (10 mg/mL) in a PCR tube, and mixer for 1 hour to reduce the disulfide bonds on the antibody. Various amounts of the linker-active agent conjugate were added to the reaction mixtures and shaken overnight using a vortex mixer. All reactions were carried out at room temperature. The resultant products were analyzed by gel electrophoretic (SDS-PAGE) and HIC (Hydrophobic Interaction Chromatography)-HPLC.

The antibody drug conjugate was analyzed by reduced SDS-PAGE: samples mixed with buffer were loaded onto 8%-15% acrylamide gels, and gel photographs were taken with a UVP BioDoc-it imaging system.

The bands (>50 kDa) appeared in lanes 2 and 3, which suggest that thiol-bridge conjugation was effective (H, L). Bands at 75 kDa represent the part composed of a heavy and a light chain which were linked by one pair of bridged thiols (LH). Two heavy chains were linked by one or two pairs of bridged thiols, which formed the bands at 100 kDa (HH). Bands at 125 kDa represent the part in which only one bridge between a heavy and a light chain was not formed (LHH). Lastly, bands at 150 kDa revealed formation of fully bridged antibody (LHHL).

The antibody drug conjugate was analyzed by HIC-HPLC under conditions: HPLC Column: TSK-GEL Butyl-NPR column 4.6*35 mm; Buffer A: 75% sodium phosphate (20 mM, pH 7.0), 25% isopropanol (v/v); Buffer B: sodium phosphate (20 mM, pH 7.0), Ammonium sulfate (1.5 mM); flow rate: 1.0 mL/min.

In Vitro Evaluation of Antibody Drug Conjugates

On the first day, a tumor cell line of human ovarian cancer cell lines, such as OVCAR3, was plated at 5000 cells in 100 μl culture medium on a 96 well culture plate (Cellstar). The cells were incubated in a CO2 incubator with saturated water at 37° C. overnight. On the second day, two covalent thiol conjugated ADCs of MSL-31 and MSL-75, were serially diluted conjugates were added to the 96 well plate containing OVCAR3 cells, 100 μl per well. The initial conjugate was 100000 ng/ml and diluted to 0.001 ng/ml. OVCAR3 cells with added ADC were incubated at 37° C. for 72 hours.

The viability of tumor cell treated covalent thiol conjugated ADC was then measured using a cell viability kit, Cell Counting Kit-8 (DOJINDO, CK04) according to the manufacturer protocol on a plate reader (BIO-RAD iMark SpectraMax L from Molecular device). The IC50 value, 50% inhibition of cell growth was calculated using a curve fitting software, Graphpad.

Example II-1 Preparation of MSL-C31

Figure 2:
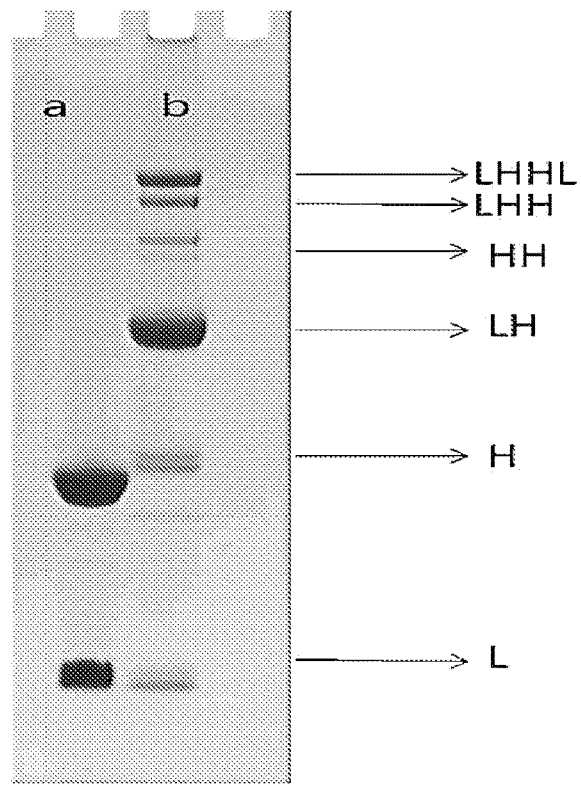
FIG. 2 is an SDS-PAGE image of an exemplary anti-Her-2 ADC comprising an anti-Her-2 monoclonal antibody conjugated with a cytotoxin prepared using Mc-VC-PAB-MMAE.
Figure 3:
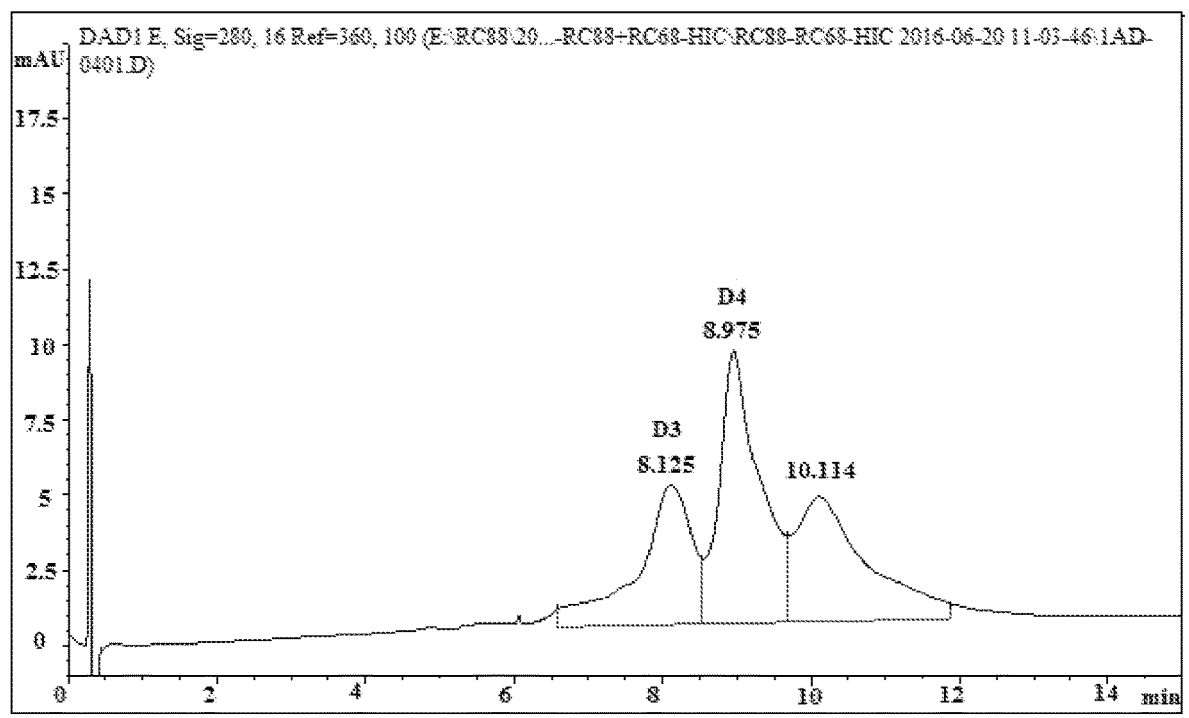
FIG. 3 shows an HIC-HPLC chromatogram of MSL-C31.

DTPA (1 mM) and 5.0 equiv. of TCEP (10 mM) were added to anti-MSL (10 mg/mL) in a PCR tube. The mixture was agitated with a vortex mixer for 1 hour to reduce the disulfide bonds on the antibody. 25% of DMSO was subsequently added to the reaction mixtures. Compound 31 (5.0 equiv., 10 mM) was added to the reaction mixtures and shaken overnight using a vortex mixer. All reactions were carried out at room temperature. After reaction was over, the mixture was loaded into the Millipore 4 mL centrifugal ultrafiltration tube, and washed three times with PBS, then collected the reaction mixtures. FIG. 2 shows that products (the right lane) of covalent conjugation of at least one pair of sulfhydryl group will migrate slower than those of heavy (H) or light chain (L) alone (shown in left lane). The covalent conjugation between the heavy and light chains produced the band of 75 kDa (HL); the covalent conjugation of two heavy chains produced the band of 100 kDa (HH). There are 3 peaks in the HIC-HPLC chromatogram, representing 3, 4, and 5 of DAR, respectively. The DAR of the resultant MSL-C31 was 3.60 based on the results of HIC-HPLC (FIG. 3). FIG. 2 shows the result of reduced SDS-PAGE for, a) naked antibody, b) MSL-C31, the product of the covalent thiol-conjugate.

FIG. 3 shows an HIC-HPLC chromatogram of MSL-C31

Example II-2 Preparation of MSL-C75

DTPA (1 mM) and 5.0 equiv. of TCEP (10 mM) were added to anti-MSL (10 mg/mL) in a PCR tube. The mixture was agitated with a vortex mixer for 1 hour to reduce the disulfide bonds on the antibody. 25% of DMSO was subsequently added to the reaction mixtures. 5.0 equiv. of Compound 75 (5.0 equiv., 10 mM) was added to the reaction mixtures and shaken overnight using a vortex mixer. All reactions were carried out at room temperature. After reaction was over, the mixture was loaded into the Millipore 4 mL centrifugal ultrafiltration tube, and washed three times with PBS, then collected the reaction mixtures. The samples were subjected to analysis by electrophoresis. The results of reduced SDS-PAGE were presented at Figure-4. The left lane was naked antibody and right lane was covalent conjugate of MSL-C75. The DAR of the resultant MSL-C75 was 3.87 based on HIC-HPLC.

Figure 4:
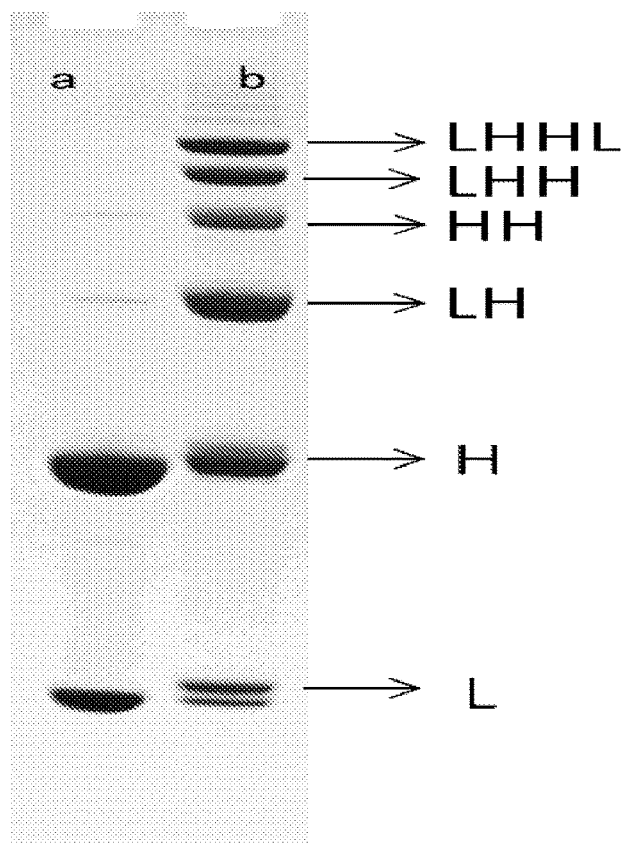
FIG. 4 shows the results of reduced SDS-PAGE of MSL-C75.

FIG. 4 shows the results of reduced SDS-PAGE of MSL-C75

Figure 5:
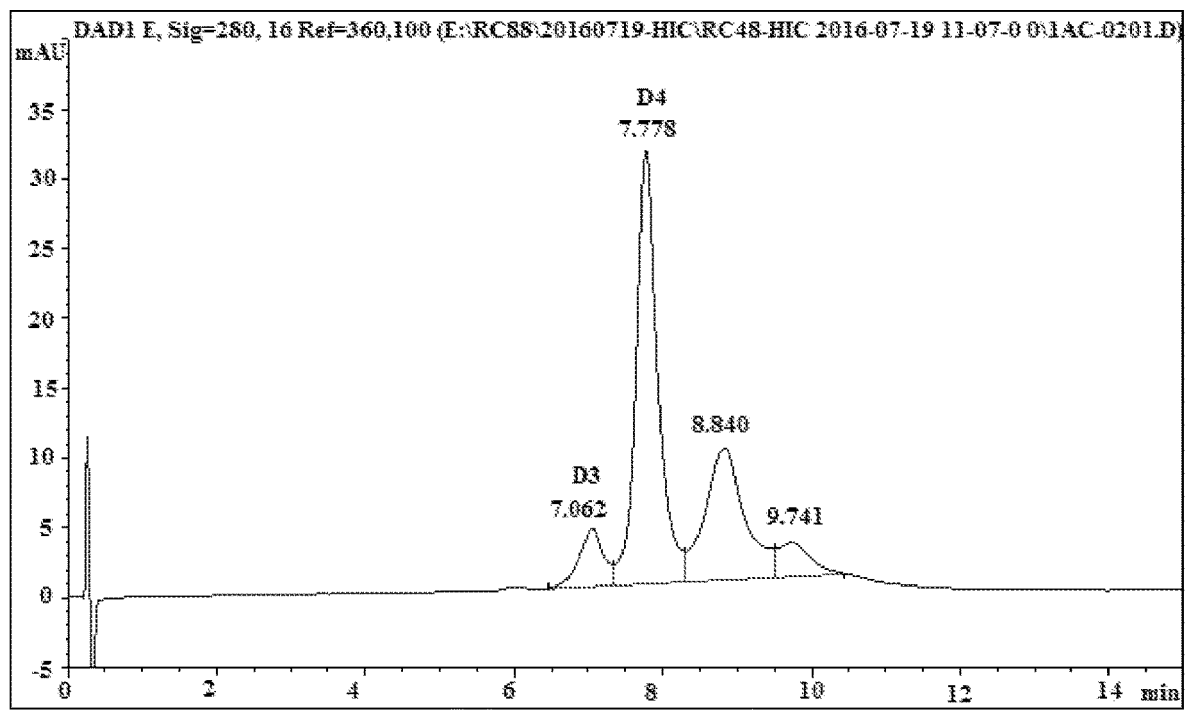
FIG. 5 shows a HIC-HPLC chromatogram of MSL-C75.

FIG. 5 shows a HIC-HPLC chromatogram of MSL-C75

Table-2 shows IC50 values of two sample: ADC-C31 and ADC-C75, tested in human ovarian cancer cells.

| Samples | Cell Type | IC50 (ng/mL) |
|---|---|---|
| MSL-C31 | OVCAR3 (MSL+) | 37.38 |
| MSL-C75 | OVCAR3 (MSL+) | 50.00 |

Example II-3 Preparation of CD59-C78

DTPA (1 mM) and 5.0 equiv. of TCEP (10 mM) were added to anti-CD59 (10 mg/mL) in a PCR tube. The mixture was agitated with a vortex mixer for 1 hour to reduce the disulfide bonds on the antibody. 25% of DMSO was subsequently added to the reaction mixtures. Compound 78 (5.0 equiv., 10 mM) was added to the reaction mixtures and shaken overnight using a vortex mixer. All reactions were carried out at room temperature. After reaction was over, the mixture was loaded into the Millipore 4 mL centrifugal ultrafiltration tube, and washed three times with PBS. The DAR of the resultant CD59-C78 was 3.66 based on HIC-HPLC.

Figure 6:
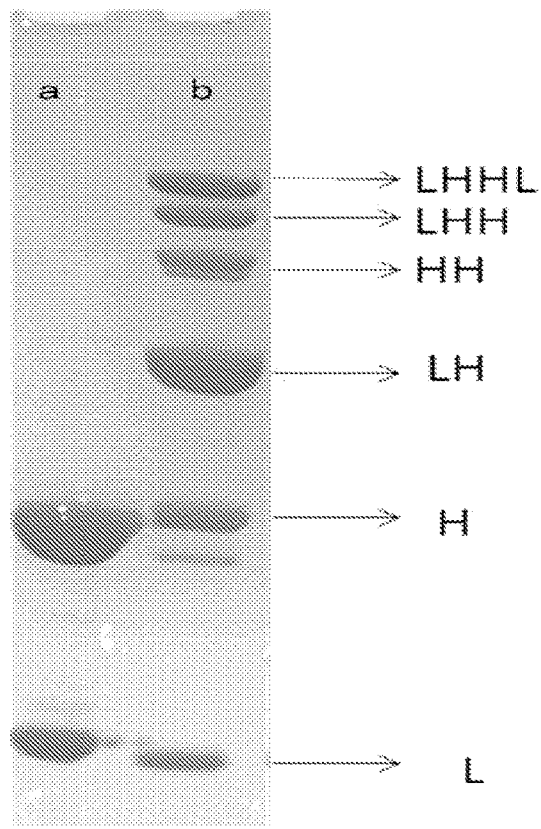
FIG. 6 shows the result of reduced SDS-PAGE for, a) naked antibody, b) CD59-C78.

FIG. 6 shows the result of reduced SDS-PAGE for, a) naked antibody, b) CD59-C78.

Figure 7:
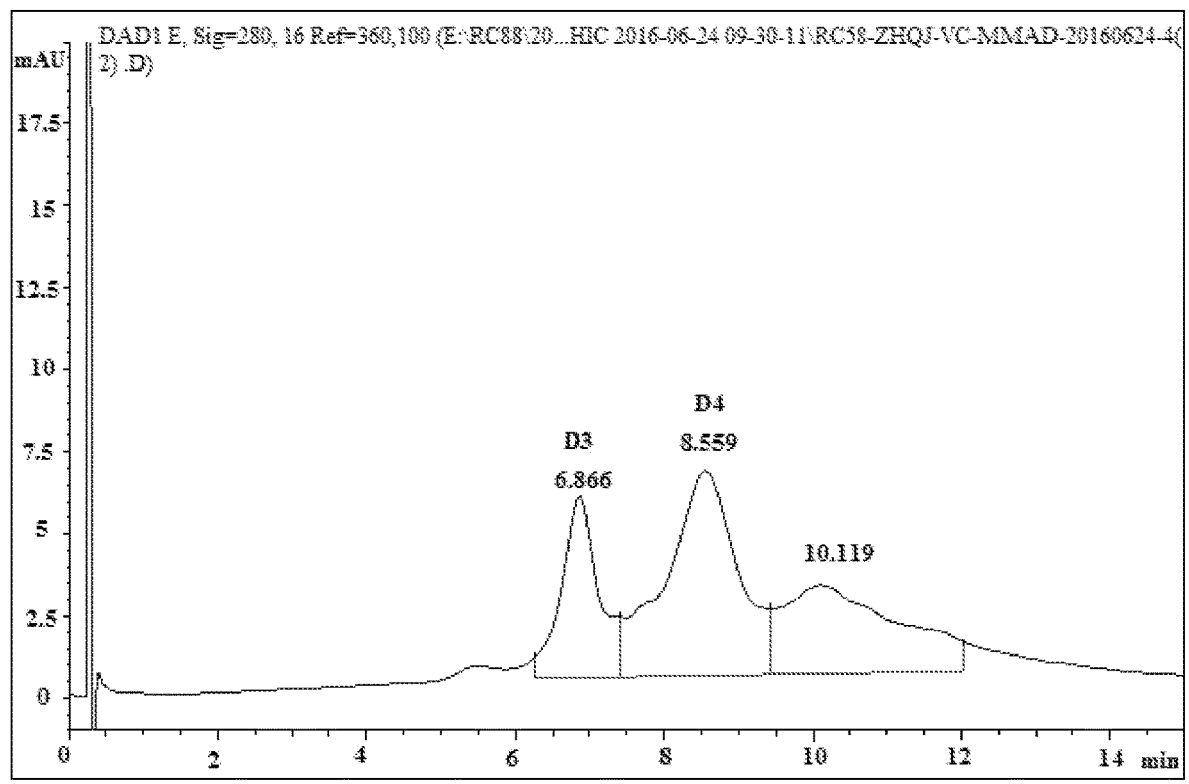
FIG. 7 shows an HIC-HPLC chromatogram of CD59-C78.

FIG. 7 shows an HIC-HPLC chromatogram of CD59-C78.

Example II-4 Preparation of HER2-C78 Conjugate

DTPA (1 mM) and 5.0 equiv. of TCEP (10 mM) were added to anti-Her2 (10 mg/mL) in a PCR tube. The mixture was agitated with a vortex mixer for 1 hour to reduce the disulfide bonds on the antibody. 25% of DMSO was subsequently added to the reaction mixtures. Compound 75 (5.0 equiv., 10 mM) was added to the reaction mixtures and shaken overnight using a vortex mixer. All reactions were carried out at room temperature. After reaction was over, the mixture was loaded into the Millipore 4 mL centrifugal ultrafiltration tube, and washed three times with PBS.

Stability Study of HER2-C78 CONJUGATE

To determine the degradation rates of ADCs of covalent thiol conjugation vs. regular thiol conjugation, three ADC samples prepared by above procedures for the ELISA were used for stability study. ELISA implementation plan as follow: Firstly, Her2-ECD (100 ng) were coated on each well of a 96-well plate; Secondly, human peripheral blood treated with Anti-Her2-Mc-VC-PAB-MMAE (of regular thiol conjugation), Anti-Her2-Di-Mc-VC-PAB-MMAE (bi-maleimide-thiol conjugation) and Anti-Her2-PY-QJ2-ADC (Her2-C78, of covalent-thiol conjugation of this invention) were incubated in the coated well to allow binding to Her-2 ECD. At last, the amount of anti-her2 ADCs bound to Her2-ECD antigen is measured by binding anti-human IgG conjugated with a streptavidin/horseradish peroxidase, which then catalyzes the conversion of the chromogenic substrate o-phenylenediamine (OPD) into a colored product. The results show that during 3 days of incubation with peripheral bloods, the degradation rate of ADC with the regular thiol conjugation was 26.7%, that of 2nd ADC with bi-maleimide-thiol conjugation was 18.9% and that of 3rd ADC of this invention was 5.1%. The degradation rate of ADC with the covalent linker of this invention is the lowest among the three ADCs as shown in Table 3 below.

TABLE 3

Summary of anti-Her2 drug conjugate degradation rates in human blood

| Compounds | Degradation Rate (3 days) |
|---|---|
| Anti-Her2-Mc-VC-PAB-MMAE | 26.7% |
| Anti-Her2-Di-Mc-VC-PAB-MMAE | 18.9% |
| Anti-Her2-PY-QJ2-ADC (Her2-C78) | 5.1% |

Notes:
Anti-Her2-Mc-VC-PAB-MMAE was conventional thiol-conjugation (ref-1) and
Anti-Her2-Di-Mc-VC-PAB-MMAE was of covalent conjugation using the structure and procedure described in the patent publication (Ref-2).
DAR values of both conjugates were comparable to that of Her2-C78.

Example III—Activity of the Antibody Drug Conjugates

The antibody drug conjugates of the subject invention can be used, in one embodiment, to specifically target tumor cells and bind to tumor-associated antigens on the surface of the tumor cells. The complex of ADC-antigen will enter the tumor cell via endocytosis and releases its payload after the endosome of the ADC-antigen complex fuses with lysosomes. The released payloads inhibit the key functions of a tumor cell and/or even kill the tumor cells. If the payloads releases on the cell surface or near the tumor cells, the tumor cell can also be killed via a by-stander manner.

Thus, the invention provides various protein-drug complexes that inhibit the growth of tumor cells and/or their differentiation. These compounds, armed with various kinds of active payloads, can be used to treat neoplasm, autoimmune disorders and inflammation, even the differentiations of a tumor or stem cell.

Example III-1—Activity Against Tumors

In one embodiment, or the subject invention, antibody drug conjugates (ADCs) combine the unique targeting of mAbs with the cancer-killing ability of cytotoxic drugs and allow ADCs to be powerful tumor-killing agents. Furthermore, the use of covalent thiol-conjugation in accordance with the subject invention increases the stability of the ADCs, limiting the decomposition of the ADC in the blood circulation, thereby reducing its toxicity. This example provides data showing treatment of human cancer, using ADCs prepared as described above, in nude mice implanted human breast cancer cells (MDA-MB-231).

To determine biological function of various ADC with covalent or regular conjugates, anti-Her-2 mAb has been thiol-conjugated with regular conjugation or covalent thiol-conjugated with the same linker and cytotoxin. The nude mice were implanted with a human cancer cell line (MDA-MB-231) and the ADCs (0, 2.5, 5.0 and 10 mg/kg) were administered through intraperitoneal injection when the tumor volume reached about 100 cubic millimeters. The tumor volumes were monitored every 3 days and animals were sacrificed at the end of 21 days and the tumors were dissected and weighed.

Table-4 below provides a comparison of efficacy between regular ADC vs. covalent thiol-conjugation ADC administered into nude mice implanted with human breast cancer cells.

TABLE 4

Covalent thiol-conjugated ADC Inhibits human tumor cell growth in nude mice study

| Treatments (10 mg/kg) | Treatment Time (Days) | Tumor volume in cubic mm (% of Vehicle) |
|---|---|---|
| Vehicle | 21 | 1084 (100%) |
| Regular ADC | 21 | 536 (49.5%) |
| Covalent-ADC | 21 | 450 (41.6%) |

REFERENCES

1. Yao Xuejing, Jing Jiang, Xin Wang, Changjiang Huang Dong Li, Kuan Xie, Qiaoyu Xu, Hongwen Li, Zhuanglin Li, Liguang Lou and Jianmin Fang, 2015 "A novel humanized anti-her2 antibody conjugated with MMAE exerts potent anti-tumor activity," Breast Cancer Research & Treatment, 153(1):123-133.
2. An Deqiang et al., 2014 Jul. 23 一种三齿型连接子及其应用 CN103933575A

We claim:

1. An antibody-drug conjugate having the following formula:

(Formula II)

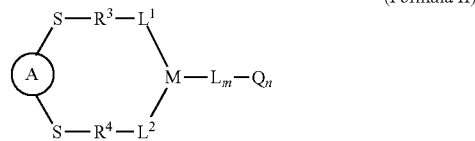

or a pharmaceutically acceptable salt thereof,
wherein:
$L^1$, and $L^2$ each represent a linker independently selected from $C_1$-$C_6$ alkyls, S, C(=O), and combinations thereof, or can be null;
M represents a linking group of

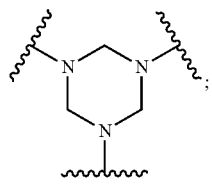 [SMILES: *N1CN(*)CN(*)C1]

Q represents an active agent selected from tubulin binders, DNA alkylators, DNA intercalators, enzyme inhibitors, immune modalators, visualization agents, peptides, and nucleotides;
L represents a linker selected from $C_1$-$C_6$ alkyls, S, C(=O), Val-Cit-PAB,

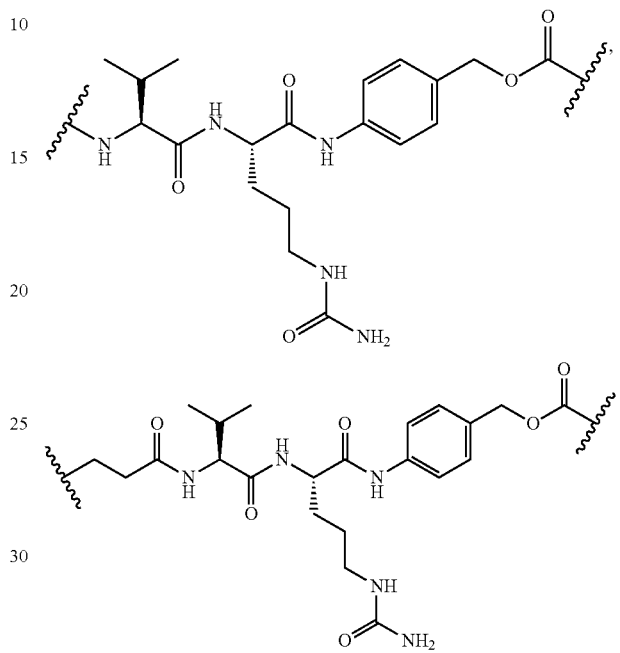

and combinations thereof;
m represents an integer from 0 to 6;
n represents an integer from 0 to 8
A is an antibody or functional fragment thereof
S is a sulfur atom of a thiol group of the targeting moiety; and
each of $R^3$ and $R^4$ is

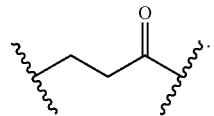 [SMILES: *CCC(*)=O]

2. The antibody-drug conjugate as claimed in claim 1, wherein the structure of Formula II is:

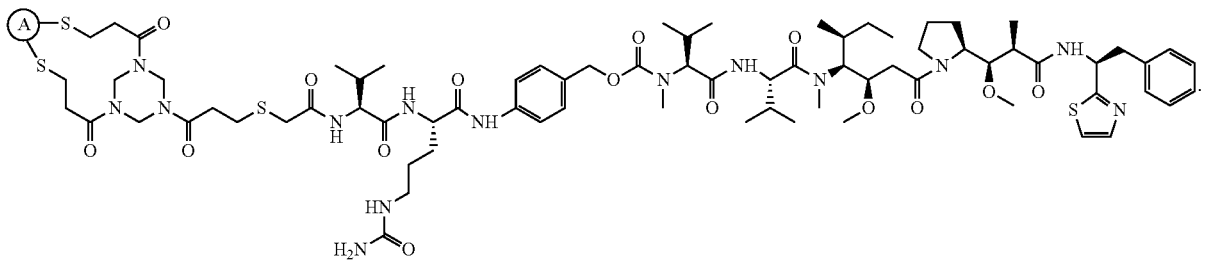

3. The antibody-drug conjugate as claimed in claim 1, wherein the antibody-drug conjugate having the following formula II:

(Formula II)

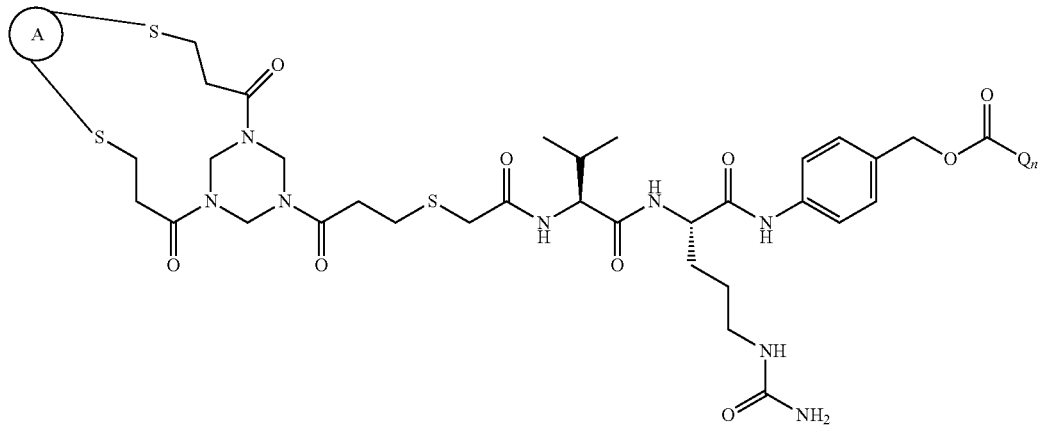

or a pharmaceutically acceptable salt thereof,
Wherein:
A is a targeting moiety;
Q is selected from tubulin binders, DNA alkylators, DNA intercalators, enzyme inhibitors, immune modulators, visualization agents, peptides, and nucleotides;
n represents an integer from 0 to 8.

4. The antibody-drug conjugate as claimed in claim 1, wherein Q is selected from

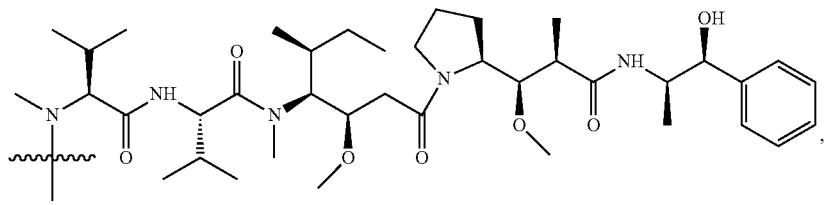

,

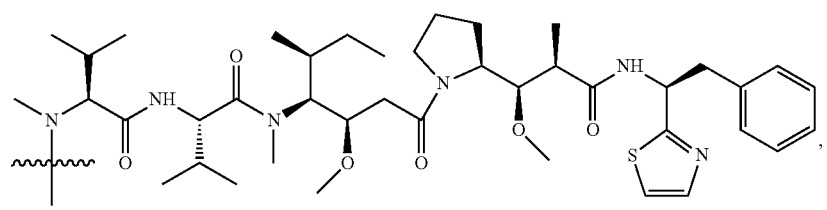

,

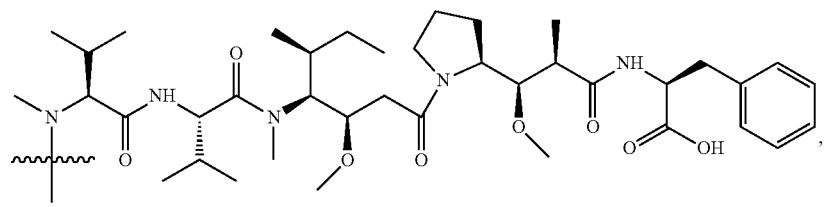

,

-continued
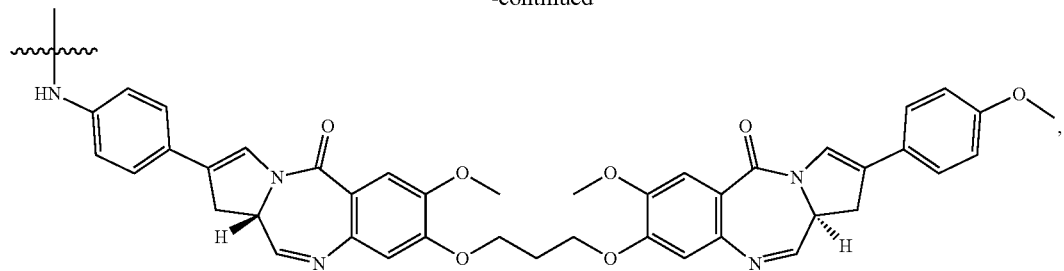
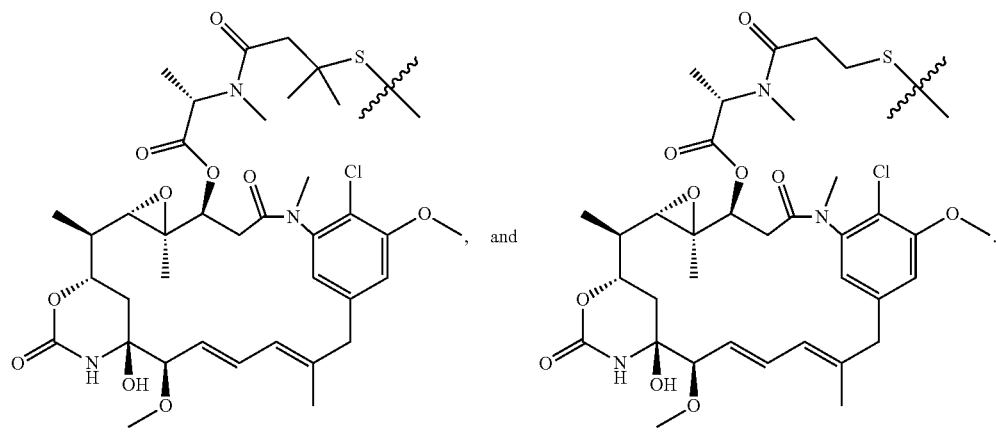
, and
5. The antibody-drug conjugate as claimed in claim 1, wherein the structure of Formula II is:
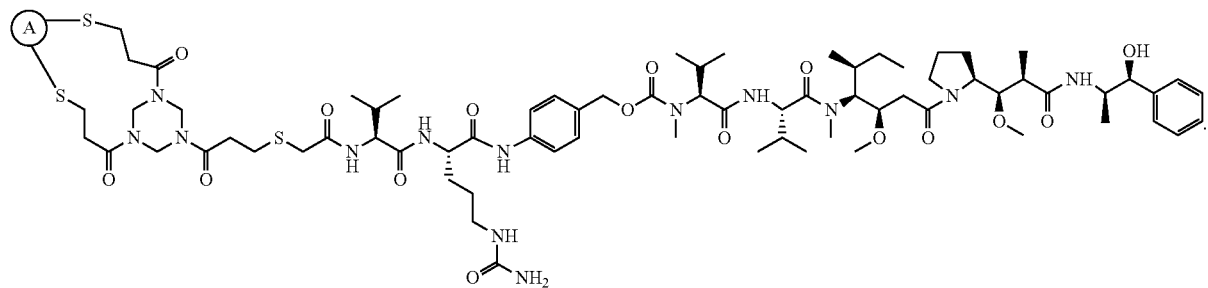
6. The antibody-drug conjugate as claimed in claim 1, wherein the structure of Formula II is:
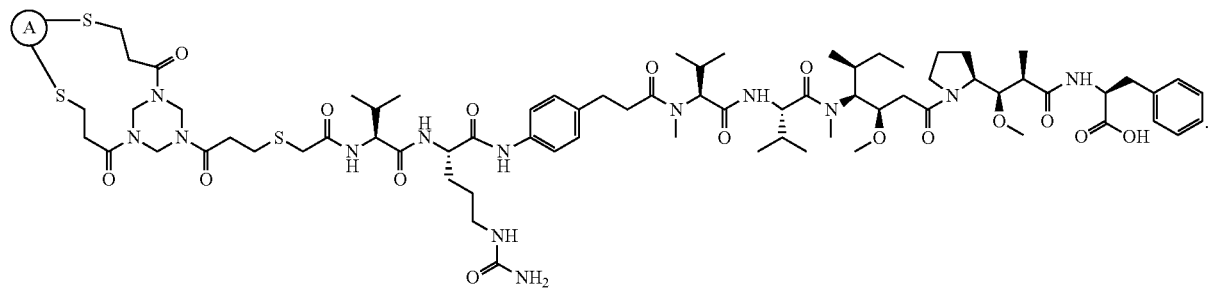

7. The antibody-drug conjugate as claimed in claim 1, wherein the structure of Formula II is:
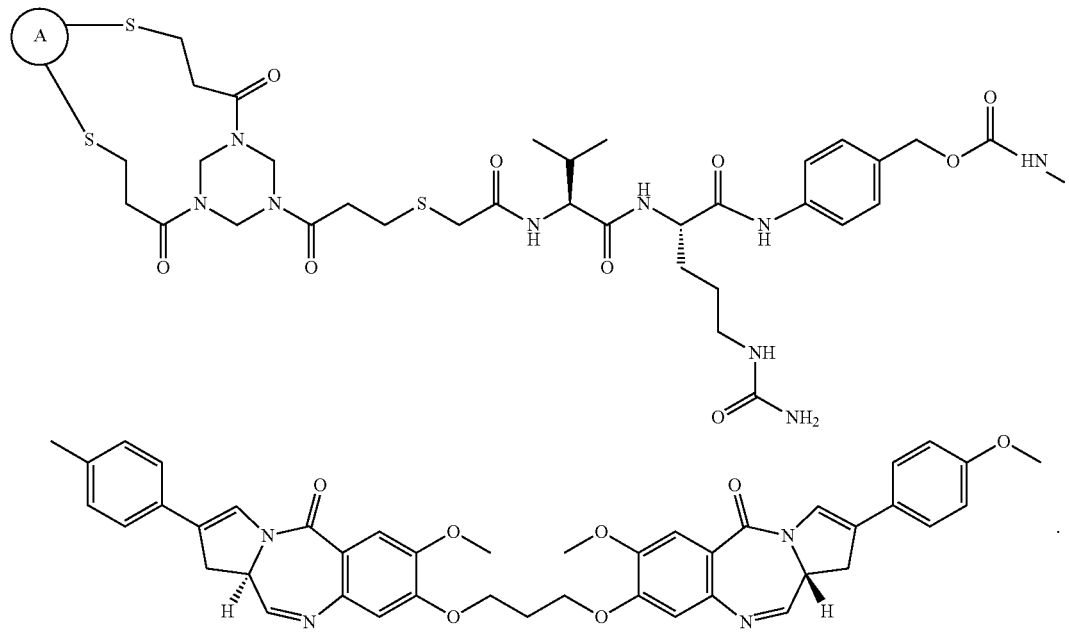
* * * * *

UNITED STATES PATENT AND TRADEMARK OFFICE
CERTIFICATE OF CORRECTION

PATENT NO. : 10,537,644 B2
APPLICATION NO. : 15/524487
DATED : January 21, 2020
INVENTOR(S) : Chang Jiang Huang et al.

Page 1 of 1

It is certified that error appears in the above-identified patent and that said Letters Patent is hereby corrected as shown below:

In the Specification

Column 6,
Line 34, "conjugated z electron" should read -- conjugated π electron --.

Column 12,
Line 14, "$R^1$ and $R^9$" should read -- $R^8$ and $R^9$ --.

Column 27,
Line 43, "$R^3$ and R" should read -- $R^3$ and $R^4$ --.

Column 39,
Line 62, "(DRT, ERK, HekS," should read -- (DRT, ERK, Hek5, --.

Column 79,
Line 47, "oil. LC-MS" should read -- oli.LC-MS --.

Signed and Sealed this
Ninth Day of June, 2020

Andrei Iancu
*Director of the United States Patent and Trademark Office*